US012576155B2

(12) United States Patent
Deng et al.

(10) Patent No.: US 12,576,155 B2
(45) Date of Patent: Mar. 17, 2026

(54) SENOLYTIC AND ANTIINFLAMMATORY PRODRUGS AND METHODS OF USE THEREOF

(71) Applicant: Peking University, Beijing (CN)

(72) Inventors: Hongkui Deng, Beijing (CN); Tuoping Luo, Beijing (CN); Yusheng Cai, Beijing (CN); Huanhuan Zhou, Beijing (CN); Yinhua Zhu, Beijing (CN); Jingjing Zhao, Beijing (CN); Jiebin Dong, Beijing (CN); Honggang Li, Beijing (CN)

(73) Assignee: Peking University, Beijing (CN)

( * ) Notice: Subject to any disclaimer, the term of this patent is extended or adjusted under 35 U.S.C. 154(b) by 1010 days.

(21) Appl. No.: 17/763,127

(22) PCT Filed: Sep. 24, 2020

(86) PCT No.: PCT/CN2020/117386
§ 371 (c)(1),
(2) Date: Mar. 23, 2022

(87) PCT Pub. No.: WO2021/057840
PCT Pub. Date: Apr. 1, 2021

(65) Prior Publication Data

US 2022/0362387 A1 Nov. 17, 2022

(30) Foreign Application Priority Data

Sep. 25, 2019 (WO) ................ PCT/CN2019/107887
Mar. 25, 2020 (WO) ................ PCT/CN2020/081133
May 28, 2020 (WO) ................ PCT/CN2020/092933

(51) Int. Cl.
*A61K 47/54* (2017.01)
*A61K 31/7068* (2006.01)
*A61P 29/00* (2006.01)

(52) U.S. Cl.
CPC ........ *A61K 47/549* (2017.08); *A61K 31/7068* (2013.01); *A61P 29/00* (2018.01)

(58) Field of Classification Search
None
See application file for complete search history.

(56) References Cited

U.S. PATENT DOCUMENTS 5,561,119 A 10/1996 Jacquesy
6,043,367 A * 3/2000 Roffler ................ C07D 491/04 546/48
2018/0094015 A1 4/2018 Mancini

FOREIGN PATENT DOCUMENTS

WO 2009016647 2/2009
WO 2017189553 11/2017

OTHER PUBLICATIONS

Aran, et al., "xCell: digitally portraying the tissue cellular heterogeneity lanscape", Genome Biol., 18:220 (2017).
Auyeung, et al., "The use of corticosteroid as treatment in SARS was associated with adverse outcomes: a retrospective cohort study", J. Infection, 51:98-102 (2005).
Baar, et al., "Targeted Apoptosis of Senescent Cells Restores Tissue Homeostasis in Response to Chemotoxicity and Aging", Cell, 169:132-147 (2017).
Baker, et al., "Clearance of p16Ink4a-positive senescent cells delays ageingassociated disorders", Nature, 479(7372):232-236 (2012).
Baker, et al., "Naturally occurring p16Ink4a-positive cells shorten healthy lifespan", Nature, 530(7589):184-189 (2016).
Bocci, et al., "Antiangiogenic versus cytotoxic therapeutic approaches to human pancreas cancer: an experimental study with a vascular endothelial growth factor receptor-2 tyrosine kinase inhibitor and gemcitabine", European Journal of Pharmacology, 498:9-18 (2004).
Bursuker, et al., ",&Galactosidase—An Indicator of the Maturational Stage of Mouse and Human Mononuclear Phagocytes", J. of Cell Physiology, 112:385-390 (1982).
Cai, et al., "Elimination of senescent cells by beta-galactosidase-targeted prodrug attenuates inflammation and restores physical function in aged mice", Cell Res., 30(7):574-589 (2020).
Chang, et al., "Clearance of senescent cells by ABT263 rejuvenates aged hematopoietic stem cells in mice", Nature Medicine, 22(1):78-83 (2016).
Channappanavar, et al., "Dysregulated Type I Interferon and Inflammatory Monocyte-Macrophage Responses Cause Lethal Pneumonia in SARS-CoV-Infected Mice", Cell Host & Microbe, 19:181-193 (2016).
Channappanavr, et al., "Pathogenic human coronavirus infections: causes and consequences of cytokine storm and immunopathology", Semin. Immunopathol., 39:529-539 (2017).
Childs, et al., "Cellular Identification and Quantification of Senescence-Associated β-Galactosidase Activity In Vivo", Cellular Scenescence: methods in Molecular Biology, 1896:31-38 (2019).
Childs, et al., "Cellular senescence in aging and age-related disease: from mechanisms to therapy", Nat. Med., 21(12):1424-1435 (2015).
Cho, et al., "Aging and Lung Disease", Annu. Rev. Physiol., 82:433-459 (2020).

(Continued)

*Primary Examiner* — Patrick T Lewis
(74) *Attorney, Agent, or Firm* — Pabst Patent Group LLP

(57) ABSTRACT

Senolytic and anti-inflammatory prodrugs are provided, which are designed from a cytotoxic agent, by chemically modifying the cytotoxic agent to incorporate a site cleavable by SA-β-gal following delivery of the prodrug in vivo, to release the active parent drug. The prodrug includes a galactose-based moiety, which is preferably acetylated, and benzyl oxy carboxy group and a cytotoxic agent moiety. The selenolytic prodrug is used to selectively kill one or more senescent cells and/or reduce an acute or chronic inflammatory response in a subject in need thereof, by administering to the subject therapeutically effective amount of the senolytic prodrugs. The disclosed compositions can be used to reduce one or more symptoms associated with a Senescence-associated disease or disorder or an inflammatory disorder, for example, a virus-mediated inflammation, in a subject.

27 Claims, 36 Drawing Sheets

(56) References Cited

OTHER PUBLICATIONS

Coppe, et al., "Senescence-Associated Secretory Phenotypes Reveal Cell-Nonautonomous Functions of Oncogenic RAS and the p53 Tumor Suppressor", PloS Biology, 6(12):e301:2853-2868 (2008).
Coppe, et al., "The Senescence-Associated Secretory Phenotype: The Dark Side of Tumor Suppression", Ann. Rev, Pathol., 5:99-118 (2010).
De Wit, et al., "SARS and MERS: recent insights into emerging coronaviruses", nat. Rev. Microbiol., 14:523-534 (2016).
Deursen, et al., "The role of senescent cells in ageing", Nature, 509(7501):439-446 (2014).
Dimri, et al., "A biomarker that identifies senescent human cells in culture and in aging skin in vivo", PNAS, 92:9363-9367 (1995).
Dinarello, et al., "Interleukin-18 and IL-18 Binding Protein", Front. Immunol., 4:289 (2013).
Frescas, et al., "Murine mesenchymal cells that express elevated levels of the CDK inhibitor p16(Ink4a) in vivo are not necessarily senescent", Cell Cycle, 16(16):1526-1533 (2017).
Fuhrmann-Stroissnigg, et al., "Identification of HSP90 inhibitors as a novel class of senolytics", Natue Commun., 8(422):1-14 (2017).
Ghosh, et al., "A daunorubicin b-galactoside prodrug for use in conjunction with gene-directed enzyme prodrug therapy", Tatrehedron Letters, 41:4871-4874 (2000).
Giamerellos-Bourboulis, et al., "Complex Immune Dysregulation in COVID-19 Patients with Severe Respiratory Failure", Cell Host Microbe, 27:992-1000 (2020).
Golonka, et al., "Harnessing innate immunity to eliminate SARS-Co V-2 and ameliorate COVID-19 disease", Physiol. Genomics, 52:217-221 (2020).
Gralinski, et al., "Complement Activation Contributes to Severe Acute Respiratory Syndrome Coronavirus Pathogenesis", MBIO, 9(5):e01753-18 (2018).
Grasselli, et al., "Baseline Characteristics and Outcomes of 1591 Patients Infected With SARS-CoV-2 Admitted to ICUs of the Lombardy 5 Region, Italy", JAMA, 323(16):1574-1581 (2020).
Grein, et al., "Compassionate Use ofRemdesivir for Patients with Severe Covid-19", Compassionate use of Remdesivir for patients with Sever Covid-19, The New England Journal of Medicine, 382(24):2327-2336 (2020).
Habiro, et al., "Involvement of p38 mitogen-activated protein kinase in gemcitabine-induced apoptosis in human pancreatic cancer cells", Biochem. and biophys. Res. Comm., 316:71-77 (2004).
Hall, et al., "Aging of mice is associated with p16(Ink4a) _ and β_galactosidasepositive macrophage accumulation that can be induced in young mice by senescent cell", Aging, 8(7):1294-1311 (2016).
Hamidzadeh, et al., "Macrophages and the Recovery from Acute and Chronic Inflammation", Annu. Rev. Physiol., 79:567-592 (2017).
Hebert, et al., "Alzheimer Disease in the US population, prevelance Estimates Using the 2000 Census", Arch. Neurol., 60:1119-1122 (2003).
Hernandez-Segura, et al., "Hallmarks of Cellular Senescence", Trends in Cell Biology, 28(6):436-453 (2018).
Huang, et al., "Clinical features of patients infected with 2019 novel coronavirus in Wuhan, China", The Lancet, 395:497-506 (2020).
Humphreys, et al., "Intrinsic Epithelial Cells Repair the Kidney after Injury", Cell Stem Cell, 2:284-291 (2008).
International Search Report for PCT application PCT/CN2020/117386 dated Dec. 21, 2020.
Jaume, et al., "Anti-severe acute respiratory syndrome coronavirus spike antibodies trigger infection of human immune cells via a pH- and 15 cysteine protease-independent FcgammaR pathway", J. Virol., 85:10582-10597 (2011).
Jeon, "Local clearance of senescent cells attenuates the development of post-traumatic osteoarthritis and creats a pro-regenerative environment", Nature Medicine, 23(6):775-781 (2017).
Karampleas, et al., "Gemcitabine Based Peptide Conjugate with Improved Metabolic Properties and Dual Mode of Efficacy", Mol. Pharm., 14:674-685 (2017).
Kirkland, et al., "The Clinical Potential of Senolytic Drugs", J. Am. Geriatr. soc., 65(10):2297-2301 (2017).
Koizumi, et al., "Activation of p38 Mitogen-activated Protein Kinase is Necessary for Gemcitabine-induced Cytotoxicity in Human Pancreatic Cancer Cells", AntiCancer Research, 25:3347-3354 (2005).
Krishnamurthy, et al., "Ink4a/Arf expression is a biomarker of aging", The Journal of Clinical Ivestigation, 114(9):1299-1307 (2004).
Lee, et al., "Senescence-associated β -galactosidase is lysosomal ß-galactosidase", Aging Cell, 5:187-195 (2006).
Lehmann, et al., "Senescent Cells Drive Frailty through Systemic Signals", Trends in Mol. Med., 24(11):917-918 (2018).
Lei, et al., "Longitudinal association between markers of liver injury and mortality in COVID-19 in China", Hepatology, 72(2):389-398 (2020).
Liao, et al., "Single-cell landscape ofbronchoalveolar immune cells in patients with COVID-19", Nat. Med., 26:842-844 (2020).
Liu, et al., "Anti-spike IgG causes severe acute lung injury by skewing macrophage responses during acute SARS-Co V infection", JCI insight 4(4):e123158 (2019).
Lopez-Otin, et al., "The Hallmarks of Aging" Cell, 153:1194-1217 (2013).
Lozano-Torres, et al., "The chemistry of senescence", 3:426-441 (2019).
Luo, et al., "Tocilizumab treatment in COVID-19: A single center experience", J. Med. Virol., 92:814-818 (2020).
Macedo, et al., "Mitotic Dysfunction Associated with Aging Hallmarks", 7:153-188 (2017).
Magro, et al., "Complement associated microvascular injury and thrombosis in the pathogenesis of severe COVID-19 infection: a report of five cases", Transl. Res., 220:1-13 (2020).
McHugh, et al., "Senescence and aging: Causes, consequences, and therapeutic avenues", J. cell biol, 217(1):65-77 (2018).
Mehta, et al., "COVID-19: consider cytokine storm syndromes and immunosuppression", 395(10229):1033-1034 (2020).
Merad, et al., "Pathological inflammation in patients with COVID-19: a key role for monocytes and macrophages", Nat. Rev. Immunol., 20:355-362 (2020).
Minamino, et al., "A crucial role for adipose tissue p53 in the regulation of insulin resistance", Nature Medicine, 15(9):1082-1088 (2009).
Mini, et al., "Cellular pharmacology of gemcitabine", Annals of Oncology, 17(Supplement 5):v17-v12 (2006).
Moeller, et al., "The bleomycin animal model: A useful tool to investigate treatment options for idiopathic pulmonary fibrosis?", The International Journal of Biocehmistry & Cell Biology, 40:362-382 (2008).
Moore, et al., "Cytokine release syndrome in severe COVID-19", Science, 368:473-474 (2020).
Moysan, et al., "A Review of Several Promising Chemical Modifications: Fluorinated lipid nanocapsules as oxygensensor Molecular Pharmaceutics", American Chemical Society, 10(2):430-444 (2013).
Munster, et al., "Respiratory disease in rhesus macaques inoculated with SARS-CoV-2", Nature, 585(7824):268-272 (2020).
Oishi, et al., "Macrophages in age-related chronic inflammatory diseases", npj Aging and Mechanisms of Disease, 16018:1-8 (2016).
Page, et al., "Induction of alternatively activated macrophages enhances pathogenesis during severe acute respiratory syndrome coronavirus infection", J. virol., 86:13334-13349 (2012).
Pepeu, et al., "Mild cognitive impairment: animal models", Dialogues in Clinical Neuroscience, 6(4):369-377 (2004).
Rettig, et al., "Gemcitabine depletes regulatory T-cells in human and mice and enhances triggering of vaccine-specific cytotoxic T-cells". Inter. J. of Cancer, 129:832-838 (2011).
Risitano, et al., "Complement as a target in COVID-19?", Nature reviews. Immunology, 20:343-344 (2020).
Ritchie, et al., "Immunosuppression for hyperinflammation in COVID-19: a double-edged sword?", Lancet, 395(10230):1111 (2020).
Roberts, et al., "Senescence in human intervertebral discs", Eur. Spine J., 15(Suppl.3):S312-S316 (2006).
Russell, et al., "Clinical evidence does not support corticosteroid treatment for 2019-nCoV lung injury", The Lancet, 395:473-475 (2020).

(56) References Cited

OTHER PUBLICATIONS

Sarkar, et al., "Disaccharide uptake and priming in animal cells: Inhibition of sialyl Lewis X by acetylated Gal~I-4GlcNAc~-O-naphthalenemethanol", PNAS, 92(30): 3323-3327 (1995).
Sharma et al. ,"Development of a theranostic prodmg for colon cancer therapy by combining ligand-targeted delivery and enzyme-stimulated activation", Biomaterials, 155:145-151 (2017).
Sharpless, et al., "Forging a signature of in vivo senescence", 15:397-408 (2015).
Tay, et al., "The trinity of COVID-19: immunity, inflammation and intervention", Nature reviews. Immunology, 20:363-374 (2020).
Tchkonia, et al., "Fat tissue, aging, and cellular senescence", Aging Cell, 9:pp. 667-684 (2010).
Torres, et al., "An Off-On Two-Photon Fluorescent Probe for Tracking Cell Senescence in Vivo", J. of the Amer. Chem. Soc., 139(26):8808-8811 (2017).
Wang, et al., "Clinical Characteristics of 138 Hospitalized Patients With 2019 Novel Coronavirus-Infected Pneumonia in Wuhan, China", JAMA , 323:1061 (2020a).
Wang, et al., "DNA damage response and cellular senescence in tissues of aging mice", Aging Cell, 8:311-323 (2009).
Wang, et al., "Remdesivir in adults with severe COVID-19: a randomised, double-blind, 25 placebo-controlled, multicentre trial", The Lancet, 395:1569-1578 (2020b).
Wen, et al., "Immune cell profiling of COVID-19 patients in the recovery stage by single-cell sequencing", Cell Discov., 6:31 (2020).
Xu, et al., "Senolytics Improve Physical Function and Increase Lifespan in Old Age", Nat. Med., 24:1246-1256 (2018).
Yang, et al., "Clinical course and outcomes of critically ill patients with SARS-Co V-2 pneumonia in Wuhan, China: a single-centered, retrospective, observational study", The Lancet Respiratory Medicine, 8:475-481 (2020).
Yip, et al., "Antibody-dependent infection of human macrophages by severe acute respiratory syndrome coronavirus", Virol., J, 11:82 (2014).
Zhang, et al., "Treat 2019 novel coronavirus (COVID-19) with IL-6 inhibitor: Are we already that far?", Drug Discoveries & Therapeutics, 14(2):100-102 (2020).
Zhao, et al., "Antibody responses to SARS-Co V-2 in patients of novel coronavirus disease 2019", Clin. Infect. Dis., 71(16):2027-2034 (2020).
Zhao, et al., "Single-Cell RNA-Seq Reveals Dynamic Early Embryonic-like Programs during Chemical Reprogramming", Cell Stem Cell, 23(1):31-45.e37 (2018).
Zhao, et al., "Two Supporting Factors Greatly Improve the Efficiencyof Human iPSC Generation", Cell Stem Cell, 3:475-479(2008).
Zhou, et al., "Clinical course and risk factors for mortality of adult inpatients with COVID-19 in Wuhan, China: a retrospective cohort study", Lancet, 395:1054-1062 (2020).
Zhu, et al., "The Achilles' heel of senescent cells: from transcriptome to senolytic drugs", Aging Cell, 14:644-658 (2015).
Bivas-Benita, et al., "Non-invasive pulmonary aerosol delivery in mice by the endotracheal route", Eur. J. Pharm. Biopharm., 61(3):214-218 (2005).
Boor, et al., "JAK-inhibitor tofacitinib suppresses interferon alfa production by plasmacytoid dendritic cells and inhibits arthrogenic and antiviral effects of interferon alfa", Trans. Res., 188:67-79 (2017).
Hantho, et al., "An enzyme-directed imidazoquinoline for cancer immunotherapy", Chem. Med. Chem. Communications., 11:2496-2500 (2016).
Kamal, et al. "Development of pyrrolo[2,l-c] [1,4] benzodiazepine ~-galactoside prodrugs for selective therapy of cancer by ADEPT and PMT", ChemMedChem., 3:794-802 (2008).
Plunkett, et al., "Gemcitabine: metabolism, mechanisms of action, and self-potentiation ", Seminars in Oncology, 22:3-10 (1995).
Schuster, et al., "Synthesis of the first spacer containing prodmg of a duocarmycin analogue and determination of its biological activity", Organic & Biomolecular Chemistry., 8:1833-1842 (2010).
English Machine Translation of First Office Action for corresponding CN (China) Application 2020800582631 dated Mar. 23, 2023.

* cited by examiner

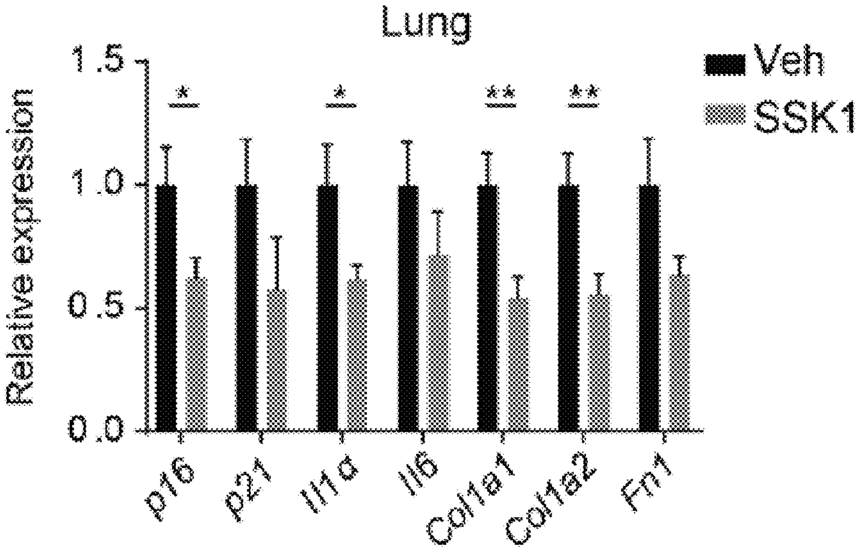
FIG. 2J
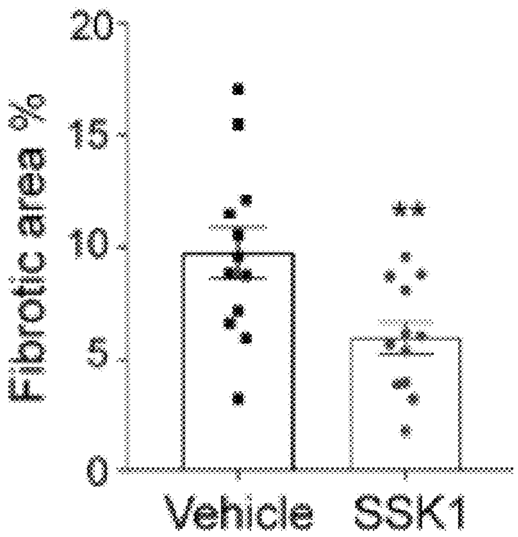
FIG. 2K
FIG. 2L
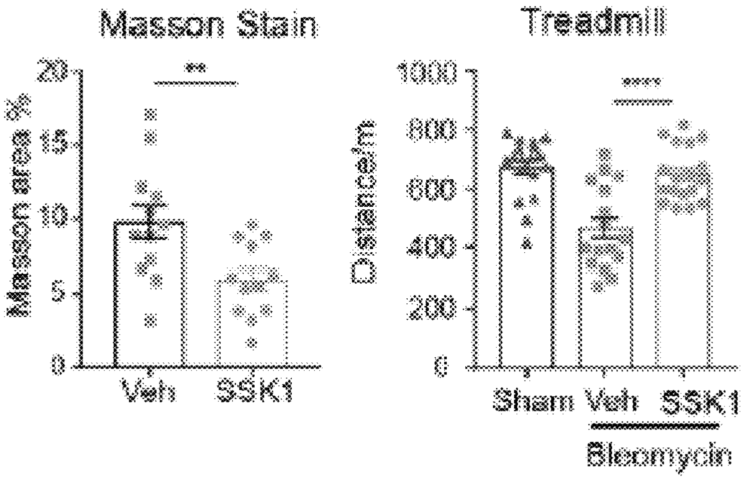

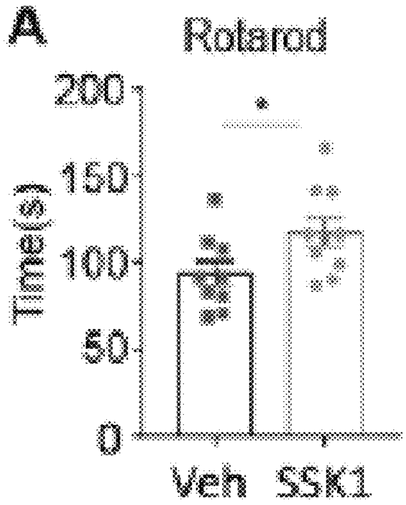
FIG. 4A
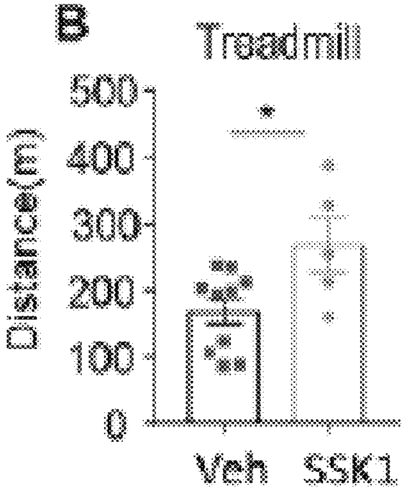
FIG. 4B
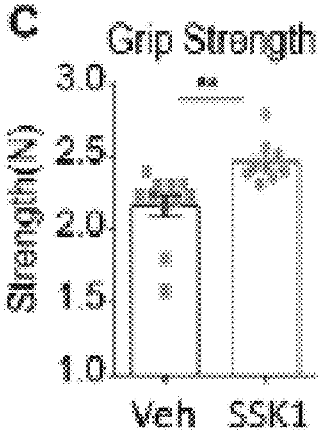
FIG. 4C
FIG. 4D
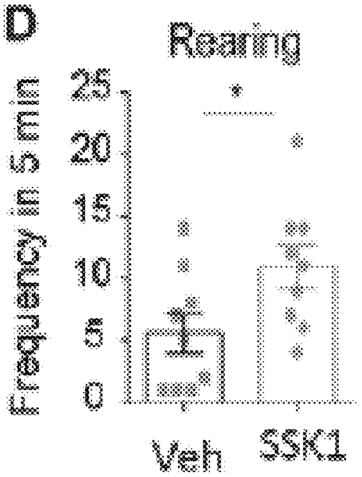
FIG. 4E
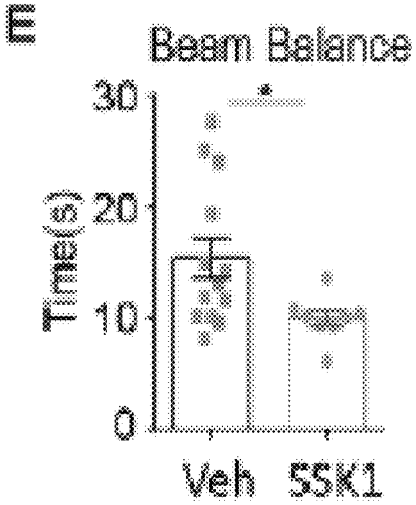

FIG. 6A
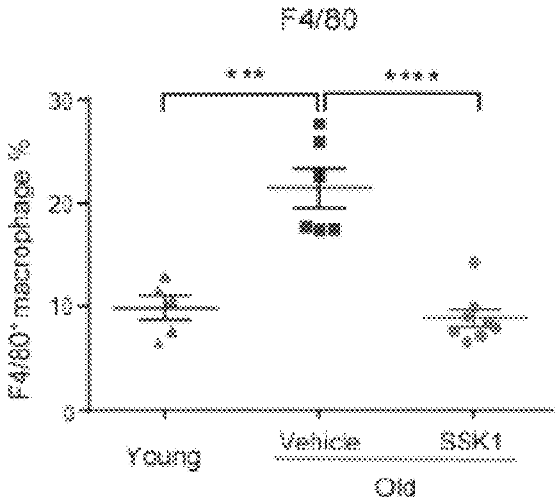
FIG. 6C
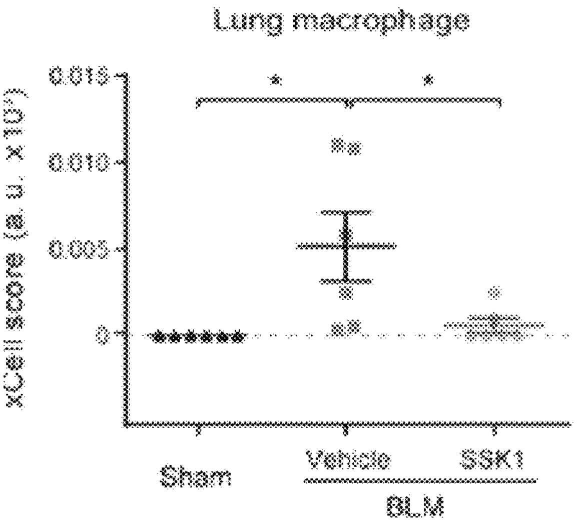
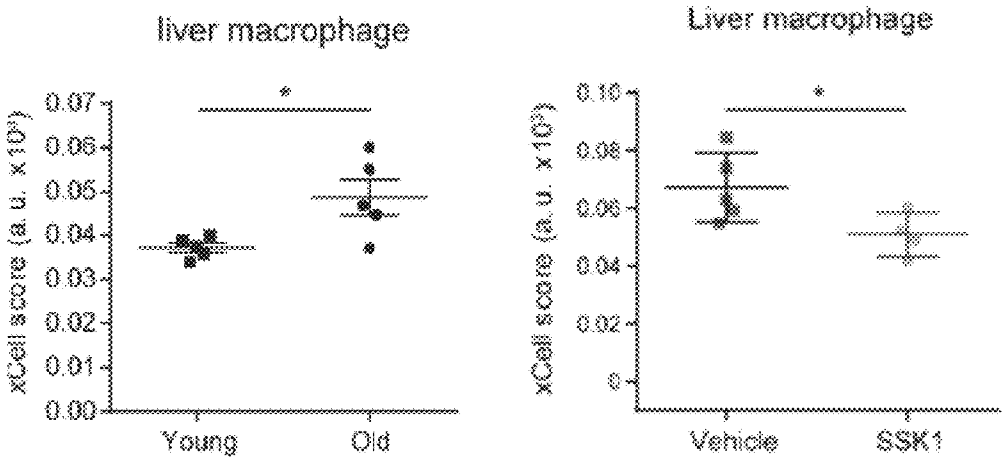
FIG. 6B

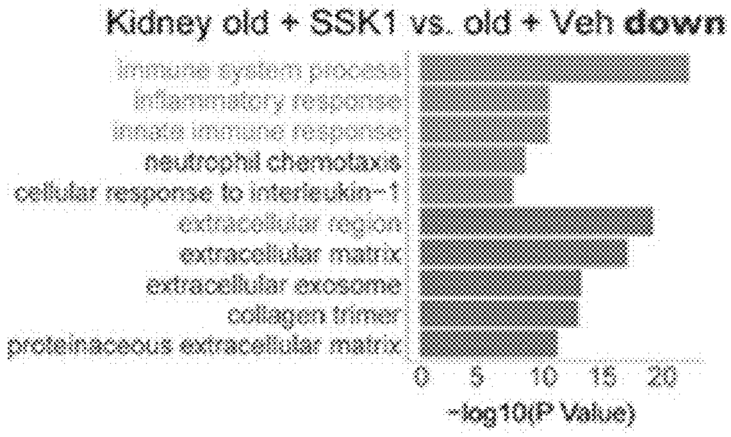
FIG. 6G
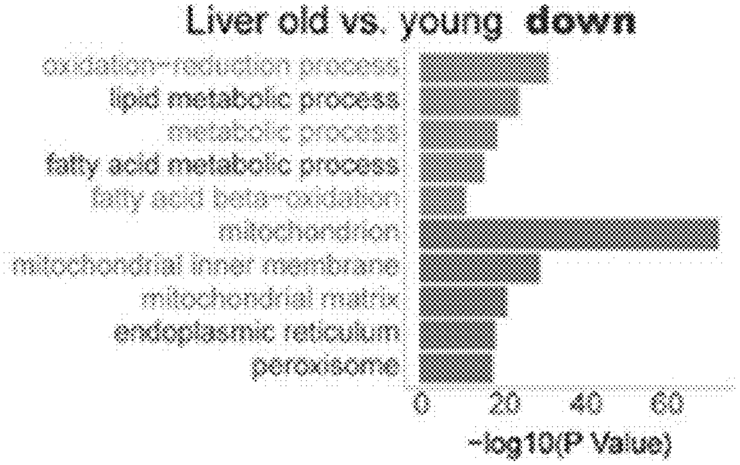
FIG. 6H
FIG. 6J
FIG. 6I
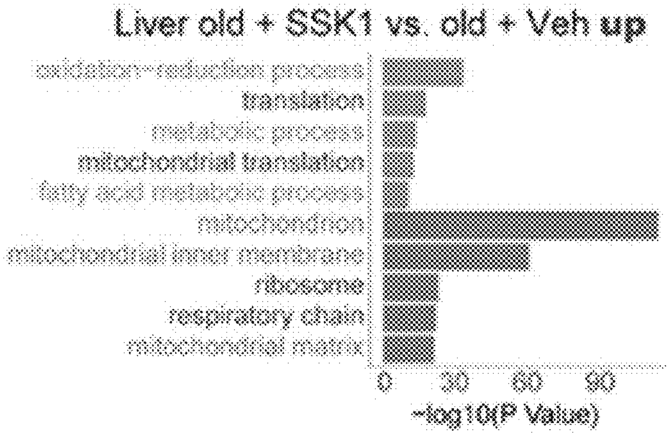
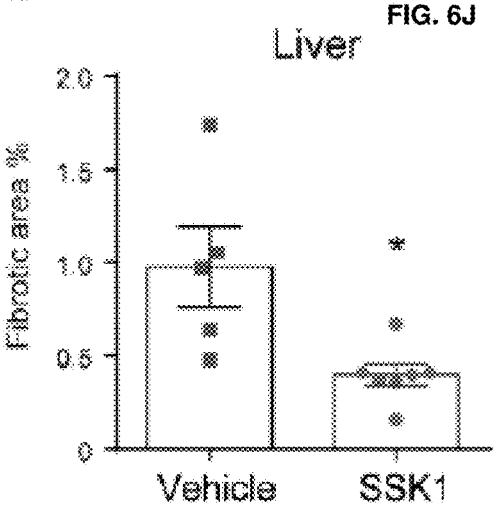

FIG. 8D
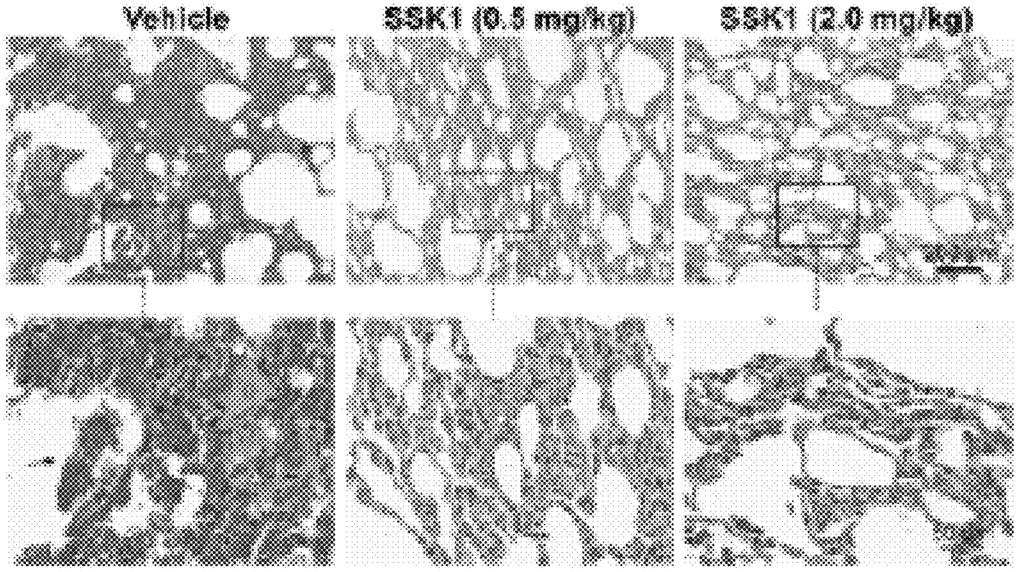
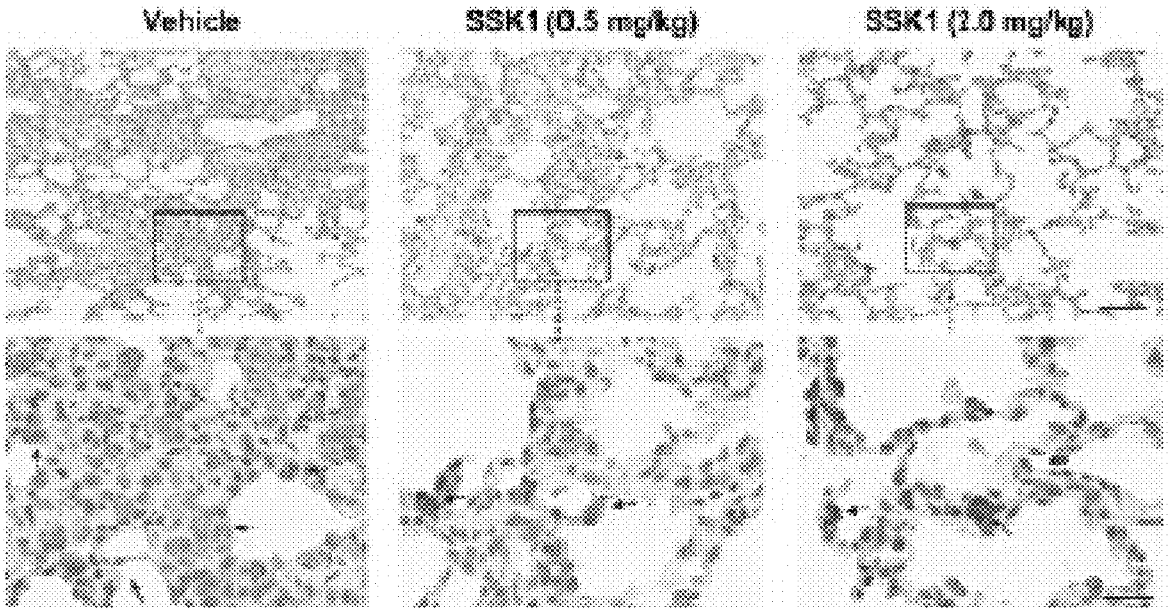
FIG. 9A

FIG. 10A
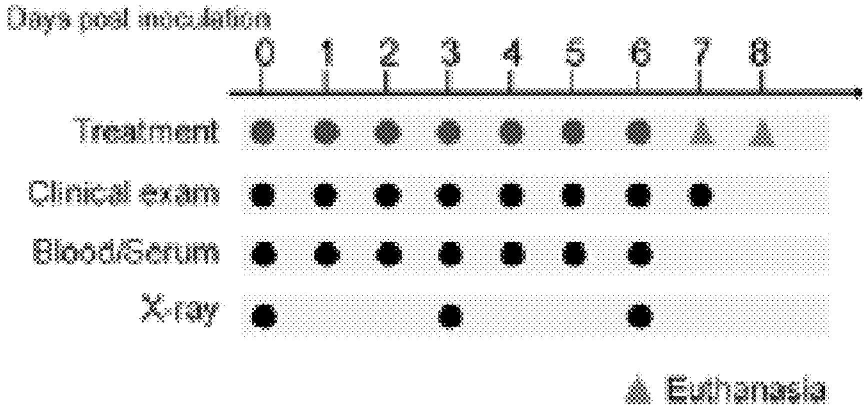
FIG. 10B
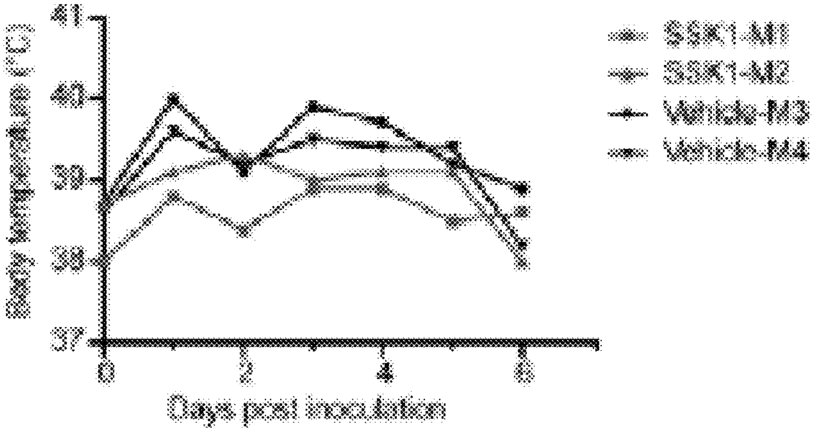
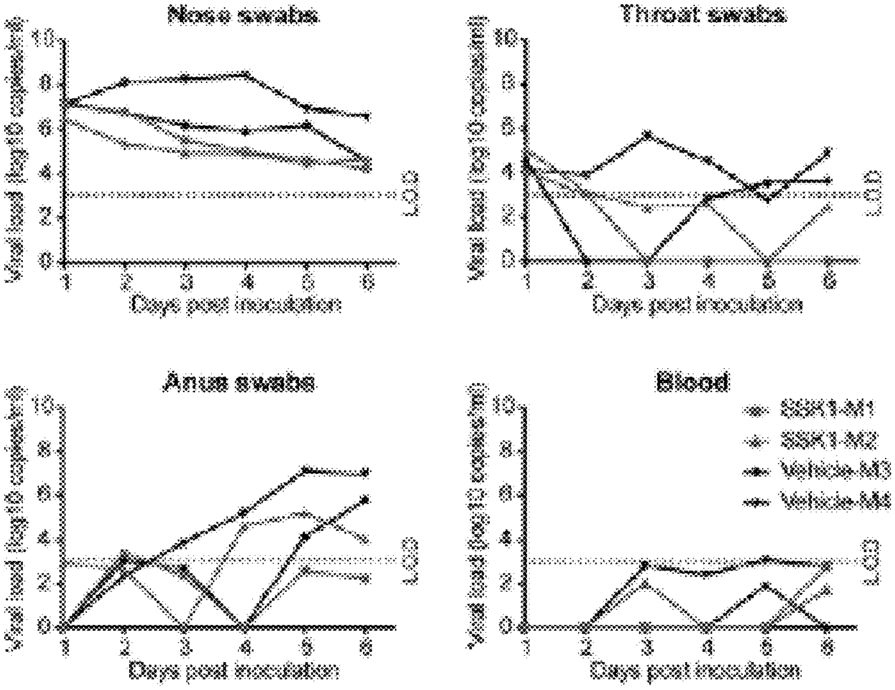
FIG. 10D

FIG. 14A
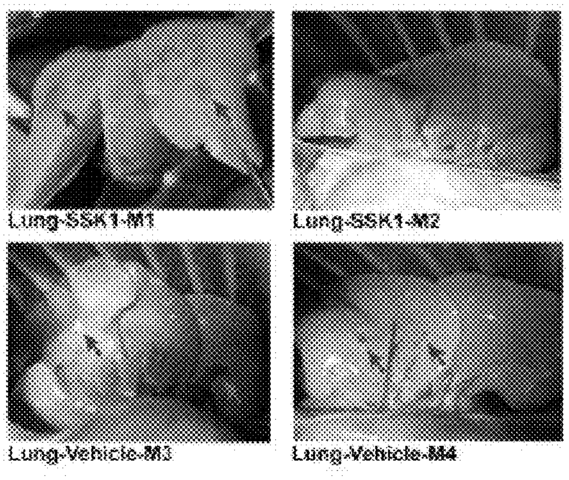
FIG. 14B
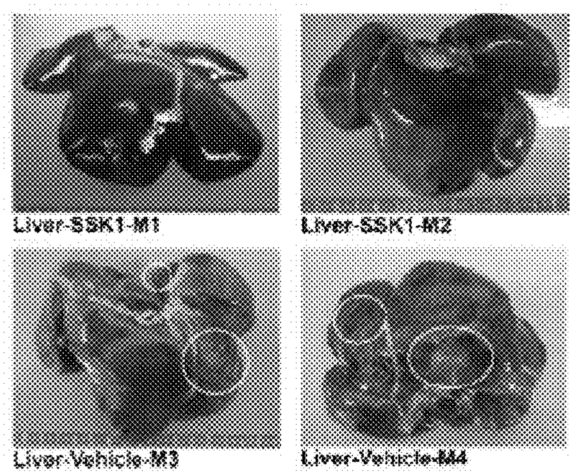
FIG. 14C
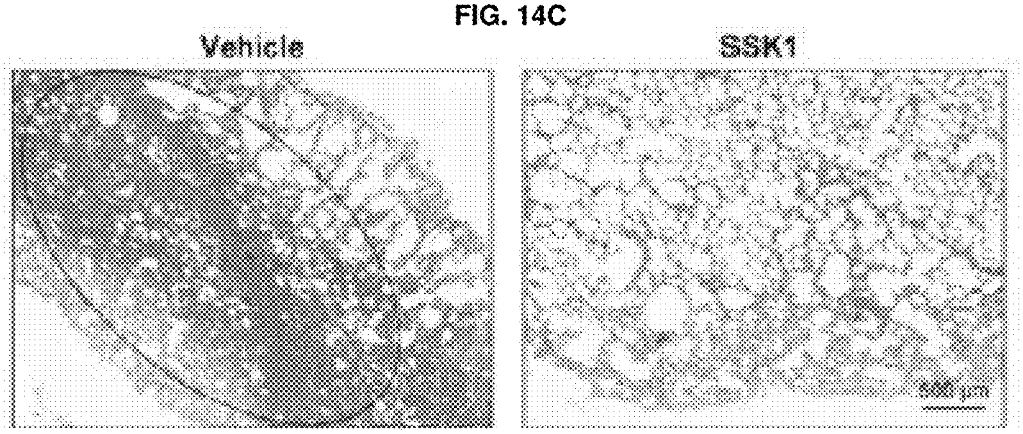
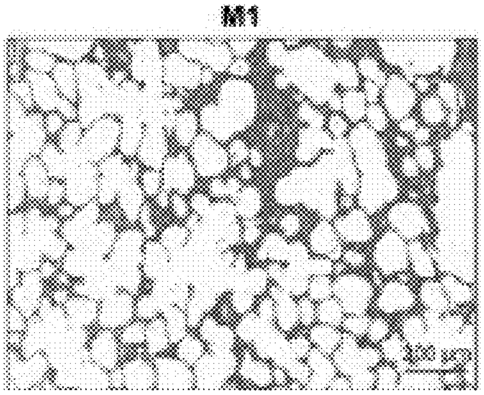
FIG. 14D

SENOLYTIC AND ANTIINFLAMMATORY PRODRUGS AND METHODS OF USE THEREOF

CROSS-REFERENCE TO RELATED APPLICATIONS

This application is a National Phase application under 35 U.S.C. 371 of PCT/CN2020/117386, filed Sep. 24, 2020, which is a continuation-in-part of International Application No. PCT/CN2019/107887, filed Sep. 25, 2019, and which is a continuation-in-part of International Application No. PCT/CN2020/081133, filed Mar. 25, 2020, and which is a continuation-in-part of International Application No. PCT/CN2020/092933, filed May 28, 2020, the disclosures of which are hereby incorporated herein by reference in their entirety.

FIELD OF THE INVENTION

The present invention relates to compounds that are capable of selectively killing senescent cells over non-senescent cells, i.e. senolytic compounds, and methods of use thereof.

BACKGROUND OF THE INVENTION

Aging is the major risk factor for physiological degeneration, increased chronic morbidities, and age-specific mortality (Lopez-Otin, et al., *Cell* 153, 1194-1217 (2013)). During the aging process, senescent cells accumulate in multiple tissues and cause tissue dysfunction (van Deursen, et al., *Nature* 509, 439-446 (2014); McHugh, et al., *J Cell Biol* 217, 65-77 (2018)). Senescent cells also secrete a variety of pro-inflammatory factors, termed the senescence-associated secretory phenotype (SASP), which leads to age-related physical decline (Coppe, et al., *PLoS Biol* 6, 2853-2868 (2008); Coppe, et al., *Annu Rev Pathol* 5, 99-118 (2010)). Elimination of senescent cells has emerged as an attractive potential method to ameliorate age-associated diseases and improve healthspan (Xu et al., *Nat Med* 24, 1246-1256 (2018); Baker et al., *Nature* 479, 232-236 (2011); Baker et al., *Nature* 530, 184-189 (2016).). Compounds that selectively kill senescent cells, known as 'senolytics', have attracted considerable interest and revealed that anti-apoptotic pathways (Zhu et al., *Aging Cell* 14, 644-658 (2015), Chang et al., *Nat Med* 22, 78-83 (2016)), HSP90 (Fuhrmann-Stroissnigg et al., *Nat Commun* 8, 422 (2017)), and FOXO4-p53 complex (Baar et al., *Cell* 169, 132-147 e116 (2017)) could be targeted to achieve this goal. However, due to the complexity and heterogeneity of senescent cells, specific and effective clearance of multiple senescent cell types remains challenging (Kirkland, et al. *J Am Geriatr Soc* 65, 2297-2301 (2017); Lozano-Torres et al., *Nature Reviews Chemistry* 3, 426-441 (2019)). Cellular senescence impairs the ability for tissue regeneration and drives chronic low-grade inflammation, which exacerbates the aging process. There remains a need to develop a new strategy that permits selectively deleting senescent cells in a wide spectrum of cell types or tissues for anti-aging interventions.

It is an object of the present invention to provide compositions for selectively targeting scenescent cells.

It is also an object of the present invention to provide compositions for reducing inflammation in a subject in need thereof.

It is also an object of the present inv invention to provide methods of selectively killing one or more senescent cells in a subject in need thereof.

It is still an object of the present invention to provide methods for ameliorating one or more symptions associated with a senescene-related disorder in a subject in need thereof.

It is also an an object of the present invention to provide methods for ameliorating one or more symptions associated with virus-induced inflammation.

SUMMARY OF THE INVENTION

Prodrugs are provided which are senolytic and antiinflammatory. The prodrugs are designed from a cytotoxic agent (parent cytotoxic agent), by chemically modifying the cytotoxic agent to incorporate a site cleavable by SA-β-gal (to release the active parent cytotoxic drug) following delivery of the prodrug in vivo, for preferentially killing senescent cells. The prodrug includes a galactose-based moiety, which is modified (herein, a modified galactose moiety), preferably by acetylation, a benzyloxycarbonyl group and a cytotoxic moiety (provided by the parent cytotoxic agent). In a preferred embodiment, the cytotoxic parent cytotoxic drug used to make the prodrug lacks a phenol group. A particularly preferred cytotoxic agent lacking a phenolic group is for example, gemcitabine, cytarabine, and 5'-Deoxy-5-fluorocytidine. In an embodiment, the prodrug may be in a crystal form.

A preferred acetylated galactose moiety is a D-galactose tetraacetate moiety, shown below.

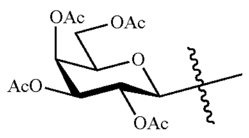

In another embodiment, one or more (e.g., two, three, or four) of the acetyl (Ac) groups may be removed from the galactose based-moiety.

A particularly preferred benzyloxycarbonyl group is shown below.

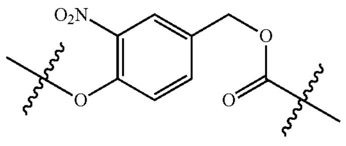 [SMILES: *Oc1ccc(COC(*)=O)cc1[N+](=O)[O-]]

3-nitro-4-oxy-benzyl Carboxy Group

In another embodiment, $NO_2$ may be removed from the above benzyloxycarbonyl group. Also disclosed is a method of selectively killing one or more senescent cells in a subject in need thereof. The method includes administering to the subject a therapeutically effective amount of one or more of the disclosed senolytic prodrugs. In some embodiments, the agent selectively kills cells undergoing oncogene-induced senescence; cells undergoing drug-induced senescence; cells undergoing age-induced senescence; cells disease-associated senescence and/or cells undergoing irradiation-induced senescence.

Methods for reducing inflammation in a subject in need thereof, are also provided. The disclosed compositions can be used to ameliorate symptoms associated with proinflammation, for example, excessive activated macrophage accumulation (and reduction of the associated cytokines). In a particularly preferred embodiment, the disclosed compositions can be administered to a subject in need thereof, to reduce inflammatory responses associated with a viral infection, for example, a coronavirus (CoV) infection, and more particularly, a SARS-CoV or SARS-CoV2 infection. In this embodiment, the composition is administered in an effective amount to reduce one or more macrophages in the subject, preferably, SA-β-gal positive macrophages.

The disclosed compositions can be used to reduce one or more symptoms associated with a Senescence-associated disease or disorder in a subject and/or one or more inflammation-associated disorders in a subject, which contains a long list of other pathologies, including neurological (e.g. brain aneurysm, Alzheimer's and Parkinson), pulmonary (e.g. idiopathic pulmonary fibrosis, chronic obstructive pulmonary disease and cystic fibrosis), ophthalmological (e.g. cataracts, glaucoma, macular degeneration), musculoskeletal (e.g. sarcopenia, disc degeneration, osteoarthritis), cardiovascular (e.g. atherosclerosis, cardiac fibrosis, aorta aneurysm), renal (e.g. chronic kidney disease, transplant complications), osteoarthritis of the knee and others such as diabetes, mucositis, hypertension, liver fibrosis and osteomyelofibrosis (OMF).

BRIEF DESCRIPTION OF THE DRAWINGS

FIG. 1A Metabolism of SSK1 into gemcitabine in SSK1-treated (0.5 μM), replication-induced senescent mouse embryonic fibroblasts (MEFs) and their non-senescent counterparts. FIG. 1B Quantification of viable cells in senescent, non-senescent, and quiescent new born fibroblasts (NBFs) incubated with increasing doses of SSK1 (n=2-4); one-way annova test for (FIG. 1B), *P<0.05, P<0.01, *P<0.001, **P<0.0001.

(FIG. 2A top panels) Representative flow cytometric plots measuring apoptosis in vehicle- or SSK1-treated senescent cells by annexin V and propidium iodide (PI) staining. (FIG. 2A, bottom bar graph) Quantitation of the percentage of viable (Q4: PI− annexin V−) and apoptotic (gate 2 and 3: PI+ annexin V+ and PI− annexin V+) cells in vehicle- or SSK1-treated senescent cell populations (n=2), *P<0.05, unpaired t-tests. (FIG. 2B) Western blot of phos-p38 MAPK and yH2AX in gemcitabine- or SSK1-treated senescent cells. (FIG. 2C) Quantitation of viable cells treated with vehicle, SSK1 (0.5 μM), or the combination of SSK1 and p38 inhibitors (n=3). FIGS. 2H-L show studies on the effect of SSK1 on SA-β-gal-positive senescent cells and lung fibrosis in a bleomycin-induced lung injury model. (FIG. 2H) Experimental design for bleomycin-induced lung injury model. (FIG. 2I) Quantification of SA-β-gal-positive cells obtained from representative images of SA-β-gal staining of lungs from bleomycin-injuried mice treated with vehicle or SSK1 (0.5 mg/kg) (vehicle-treated, n=6; SSK1-treated, n=5). (FIG. 2J) Expression of senescence- and fibrosis-associated genes by RT-qPCR in lungs of bleomycin-injured mice treated with vehicle or SSK1 (0.5 mg/kg) (vehicle-treated, n=11; SSK1-treated, n=12). (FIG. 2K) Quantification of the proportion of fibrosis of lung paraffin sections from bleomycin-injured mice after vehicle or SSK1 (0.5 mg/kg) treatment (Vehicle-treated, n=12; SSK1-treated, n=12). (FIG. 2L) The exhaustion distance (m) from measured by a treadmill test in sham surgery (n=18) and bleomycin-injured mice treated with vehicle (n=16) or SSK1 (0.5 mg/kg) (n=18). Each data point represents an individual mouse. Data are means±s.e.m. P<0.01, ****P<0.0001, unpaired t-test.

(FIG. 3A) Experimental design for SSK1 treatment of aged mice. (FIG. 3B to FIG. 3D) Quantification of SA-β-gal-positive cells in kidney (FIG. 3B), liver (FIG. 3C), and lung (FIG. 3D) (vehicle- and SSK1-treated, n=8). Scale bars, 200 μm, each data point represents an individual mouse. (FIG. 3E and FIG. 3F) Expression of p16, p21, IL1α, TNFα, and other SASP factors analyzed by RT-qPCR in liver (FIG. 3E) (vehicle-treated, n=6; SSK1-treated, n=8) and kidney (FIG. 3F) (vehicle-treated, n=8; SSK1-treated, n=7). (FIG. 3G-J) IL1α (FIG. 3G), IL6 (FIG. 3H), CXCL1 (FIG. 3I), and TNFα (FIG. 3J) protein levels in blood serum from old mice treated with SSK1 (0.5 mg/kg) or vehicle, as measured by ELISA. For (FIG. 3G to FIG. 3H): vehicle-treated, n=5, SSK1-treated, n=6; for (FIG. 3J): vehicle-treated, n=7, SSK1-treated, n=8, each data point represents an individual mouse. Data are means±s.e.m, *P<0.05, P<0.01, **P<0.0001, unpaired t-test.

FIGS. 4A-J show studies on the effect of SSK1 on physical functions of aged mice. FIGS. 4A to E. Quantification of maximal rotarod time (FIG. 4A), treadmill distance (FIG. 4B), grip strength (FIG. 4C), time to cross balance beam (FIG. 4D), and rearing exploration times (FIG. 4E) for old female mice treated with vehicle or SSK1 (0.5 mg/kg). Data are means±s.e.m, n=6-13 mice per group, each data point represents an individual mouse *P<0.05, P<0.01, unpaired t-test. (FIG. 4**F) Left, quantification of maximal rotarod time for old mice before and after treatment with vehicle or SSK1. Right, the maximal rotarod time after treatment minus the maximal time of rotarod before treatment with vehicle (n=10) or SSK1 (0.5 mg/kg, n=5). (FIG. 4G) Left, quantification of treadmill distance for old mice before and after treatment with vehicle or SSK1. Right, treadmill distance after treatment minus the treadmill distance before treatment with vehicle (n=10) or SSK1 (0.5 mg/kg, n=5). Data are means±s.e.m, each data point represents an individual mouse, *P<0.05, **P<0.01, unpaired t-test.

FIG. 4H Body weight of old female mice during vehicle or SSK1 injection. (FIG. 4I) Quantification of maximal rotarod time (left panel), treadmill distance (middle panel), and grip strength (right panel) in old male mice treated with vehicle or SSK1 (0.5 mg/kg). Data are means±s.e.m. Vehicle-treated, n=16; SSK1-treated, n=17, each data point represents an individual mouse. *P<0.05, ***P<0.001, unpaired two-way t-test. (FIG. 4J). Treatment with SSK1 improved the rotarod, treadmill, and grip strength functions when compared to the other senolytic compounds.

FIG. 6A shows quantification of liver F4/80 staining of young mice and aged mice after vehicle or SSK1 (0.5 mg/kg) treatment (young, n=5; Vehicle-treated, n=6; SSK1-treated, n=8). Scale bar, 200 μm. FIG. 6B shows xCell analysis of RNA-seq data to predict changes in macrophage infiltration in the liver young (4 mouth) and aged mice (19 mouth) (young, n=5; aged, n=5) (left) and xCell analysis of RNA-seq data to predict changes in macrophage infiltration of aged mice (22 mouth) after treatment with SSK1 (Vehicle-treated, n=6; SSK1-treated, n=8) (right). FIG. 6C shows xCell analysis of RNA-seq data to predict changes in macrophage infiltration in the lungs of sham surgery (Sham) and bleomycin-induced injury lungs, treated with vehicle, SSK1 (0.5 mg/kg) (sham surgery, n=6; vehicle-treated, n=6; SSK1-treated, n=6). FIGS. 6D-G GO Terms of up-regulated genes in the livers (FIG. D) and kidneys (FIG. F) of old mice compared with young mice; And GO terms for down-regulated genes in the livers (FIG. E) and kidneys (FIG. G) of SSK1-treated old mice relative to vehicle-treated old mice. FIGS. 6H and 6I GO Terms of down-regulated genes in the livers of old mice compared with young mice (FIG. H) and GO terms for up-regulated genes of SSK1-treated old mice relative to vehicle-treated old mice (FIG. I). Terms both in D and E (F and G; H and I) are in deeper gray. FIG. 6J Quantification of the proportion of fibrosis of liver paraffin sections from old mice treated with vehicle or SSK1 (Vehicle-treated, n=5; SSK1-treated, n=7).

FIG. 10. SSK1 Reduces Clinical Signs in SARS-COV-2-infected Rhesus Macaques upon Early-time Administration (A) Scheme of the experimental design of early SSK1 intervention. Black dot, measurement of clinical signs, blood sample and X-ray at the indicated time points. Red dot, treatment days. Brown triangle, sample collections following euthanasia. Virus inoculation was performed at 0 dpi. (B) Body temperature monitoring after infection and during the treatment period. (C) Images of dorsal-ventral radiographs of the chest of animals at 0, 3, and 6 dpi. Red circles mark ground-glass opacification representing pulmonary interstitial infiltrates. R, right side of the animal. (D) Detection of viral RNA in nose, throat, anal swabs and blood samples by RT-qPCR at different time points after infection. L.O.D.: limit of detection. See also FIG. 13.

FIG. 11. Early SSK1 Intervention Reduces Inflammatory Damage to the Lungs Histopathology examination of necropsied lung tissues of rhesus macaques (A) Left column, H&E staining indicates that SSK1 treatment recovers the thickened alveolar septum caused by SARS-CoV-2. Right column, high magnification images of the boxed area in the left column. Scale bar, left: 200 μm; right: 50 μm. (B) AB-PAS staining shows that SSK1 treatment recovers mucinous secretions in bronchioles. Scale bar, 100 μm. (C) Concentration of inflammatory cytokines in the lungs of rhesus macaques. Lung homogenates were harvested from the upper, middle and lower lobes of half necropsied lung tissues, and the levels of 23 inflammatory-related cytokines and chemokines were tested quantitatively. There were no significant differences in the concentrations of other cytokines and chemokines tested (data not shown). Unpaired two-tailed Student's t test, ns, not significant, $^{}P<0.01$. (D) Concentration measurement for IL-18 in serum samples during SSK1 treatment. See also FIG. 14**.

Figure 12:
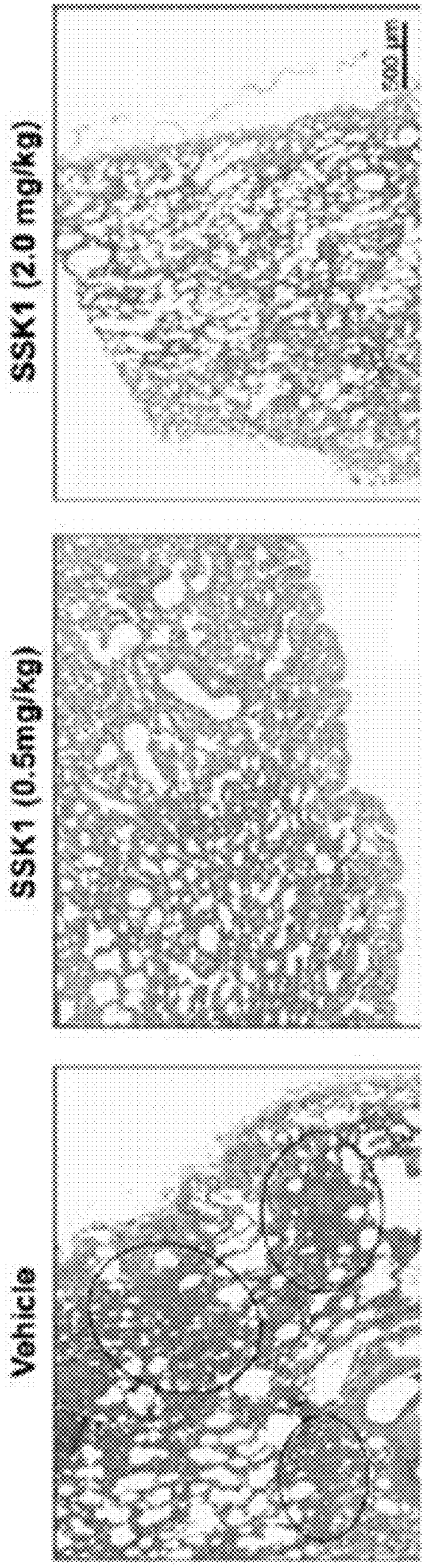

FIG. 12. (Related to FIG. 8) Low magnification images of H&E staining shows that SSK1 treatment improved the pneumonia of monkeys infected with SARS-CoV-2. Circle shows the area of interstitial pneumonia. Scale bar, 500 μm.

FIG. 13. (Related to FIG. 10) (A) Body weight changes of SARS-CoV-2-infected monkeys with vehicle and SSK1 between 0 and 7 dpi. (B) Hematological changes in SARS-CoV-2-infected rhesus macaques. M1 showed an abnormal high level of white blood cell (WBC), lymphocyte and monocyte counts in the blood. (C) Viral loads in tissues of SARS-CoV-2-infected rhesus macaques collected at the time of necropsy. L.O.D.: limit of detection.(D) Viral load (top) and virus titer (bottom) were determined in BALF collected from SARS-CoV-2 infected rhesus macaques.

FIG. 14. (Related to FIG. 11) (A and B) Gross pathology of the lungs and livers of SARS-CoV-2-infected rhesus macaques treated with SSK1. The arrows and circles represent gross lesions in the necropsied lungs or livers. (C) H&E staining shows that SSK1 treatment improved the pneumonia of monkeys infected with SARS-CoV-2. Circle shows the area of interstitial pneumonia. Scale bar, 500 μm. (D) H&E staining shows that M1 had local pulmonary hemorrhages. Scale bar, 200 μm.

Figure 15A:
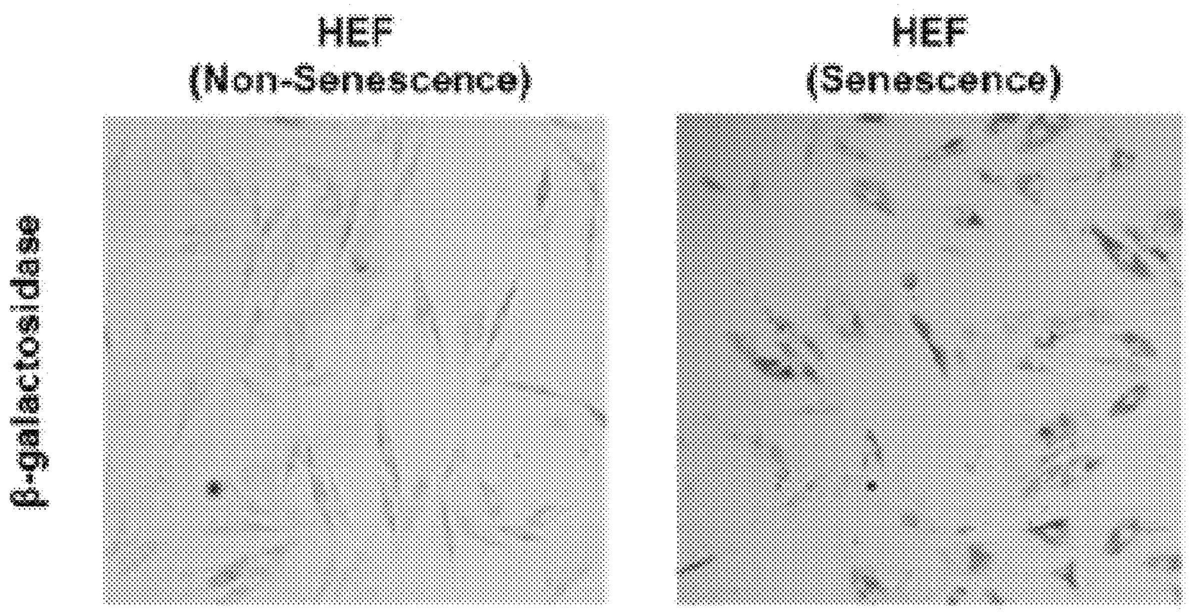
Figure 15B:
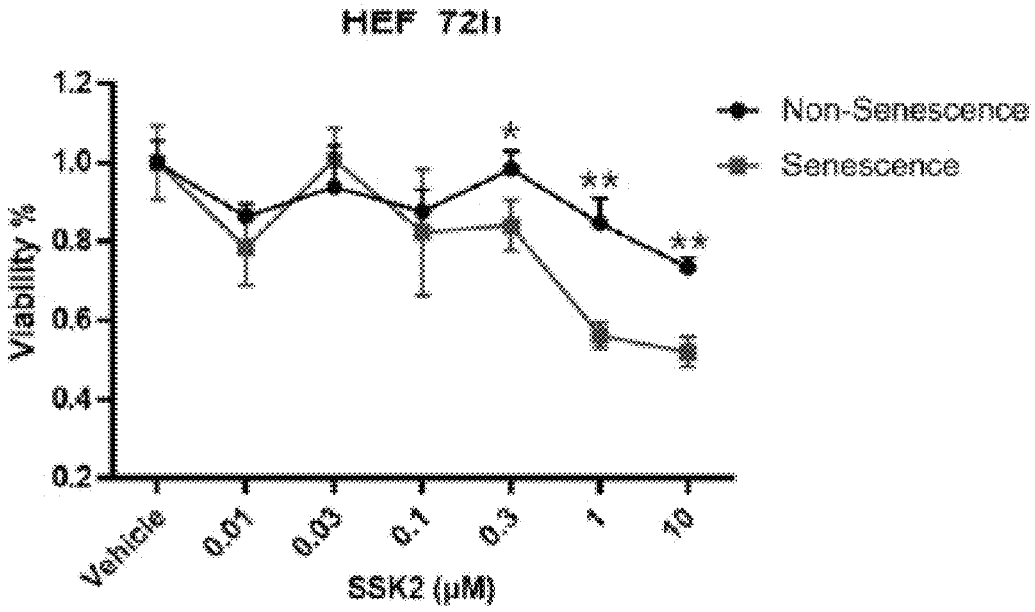

FIG. 15. SSK2 selectively eliminates senescent cells in human embryonic fibroblast in a dose-dependent manner after treatment for 72 h. A) β-galactosidase staining of non-senescence and etoposide-induced senescent HEFs. B) Quantification of viable cells in etoposide-induced senescent HEFs incubated with increasing doses of SSK2; Data were shown as mean±SD. N=3 per group. $^{*}P<0.05$, $^{**}P<0.01$.

Figure 16A:
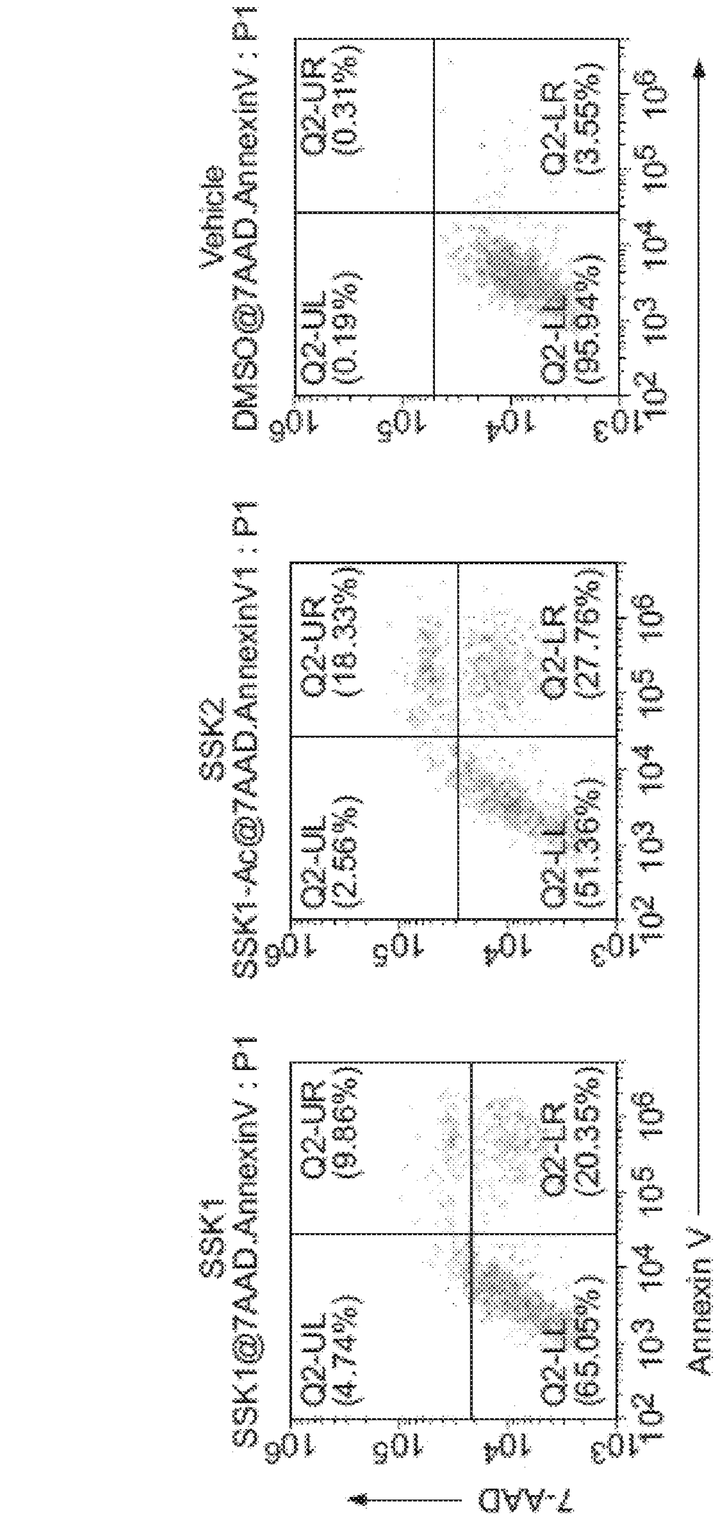
Figure 16B:
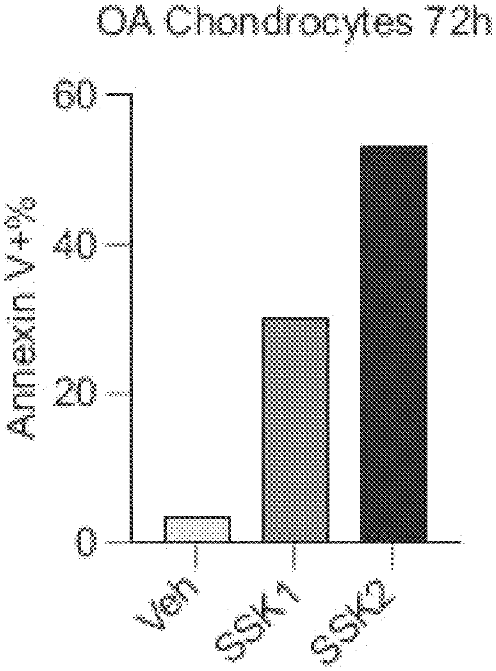
Figure 16C:
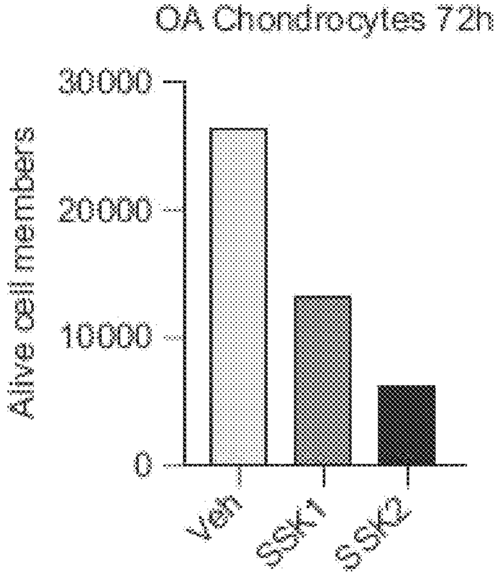

FIG. 16. The effect of SSK1 or SSK2 on the viability of primary human chondrocytes isolated from Osteoarthritis patient. A) Apoptosis analysis of chondrocytes from human OA tissue by flow cytometry after treated with 10 μM SSK1, SSK2, or Vehicle for 72 h. B-C) Quantification of Annexin V positive B) and alive C) human OA chondrocytes after treated with 10 μM SSK1, SSK2, or Vehicle for 72 h.

Figure 17:
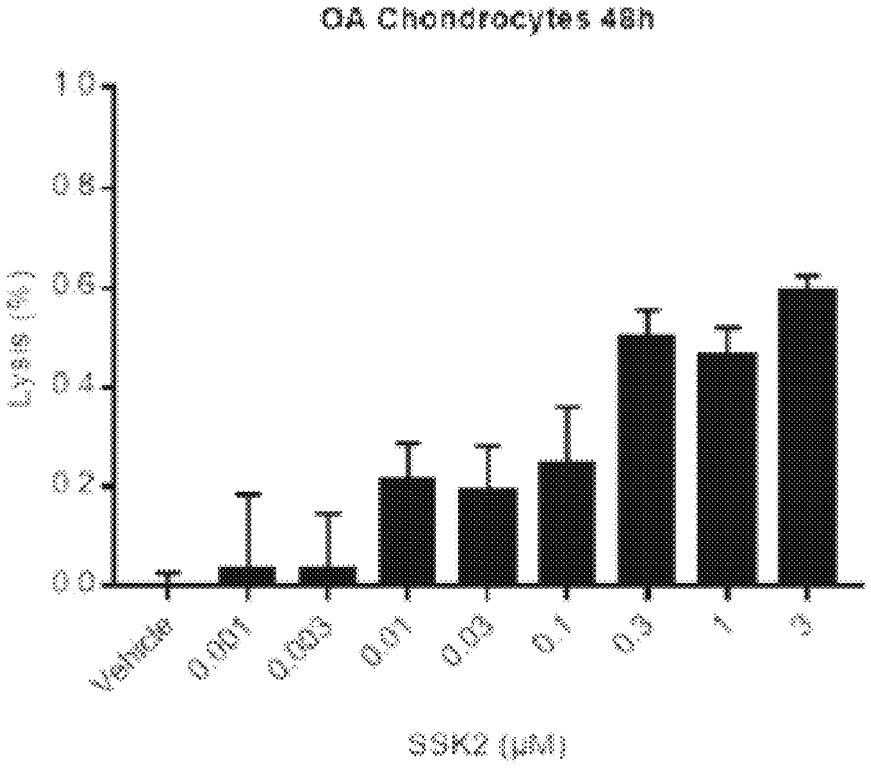

FIG. 17. Dose-dependent elimination of senescent cells in OA chondrocytes isolated from human OA tissue after SSK2 treatment for 48 h. Quantification of viable human OA chondrocytes after treatment with increasing concentrations of SSK2 for 72 h. Data were shown as mean±SD.

DETAILED DESCRIPTION OF THE INVENTION

SA-β-gal is a major characteristic of senescence and a widely used senescent marker (Dimri, et al., PNAS, 92: 9363-9367 (1995); Lee et al., *Aging Cell* 5, 187-195 (2006)), whose activity is exploited herein to selectively metabolize small molecules in senescent cells (Lozano-Torres et al., *J Am Chem Soc* 139, 8808-8811 (2017)). The compositions and methods disclosed herein are based on the development of a prodrug strategy based on SA-β-gal to release the active parent drug for preferentially killing senescent cells. The disclosed compositions can be used to ameliorate symptoms associated with proinflammation, for example, excessive accumulation of activated macrophages in response to an infection, for example, a viral infectrion.

I. Definitions

"Cytotoxic moiety" as used herein refers to the portion of the senolytic prodrug provided by the parent cytotoxic agent.

"Cytotoxic agent" as used herein refers to a chemical or drug used to kill cells.

"Parenteral administration", as used herein, means administration by any method other than through the digestive tract or non-invasive topical or regional routes.

"Patient" or "subject" to be treated as used herein refers to either a human or non-human animal.

"Parenteral administration", as used herein, means administration by any method other than through the digestive tract or non-invasive topical or regional routes.

"Patient" or "subject" to be treated as used herein refers to either a human or non-human animal.

"Senolytic" as used herein selectively killing one or more senescent cells over non-senescent cells.

"Therapeutically effective" or "effective amount" as used herein means that the amount of the composition used is of sufficient quantity to ameliorate one or more causes or symptoms of a disease or disorder. Such amelioration only requires a reduction or alteration, not necessarily elimination. As used herein, the terms "therapeutically effective amount" "therapeutic amount" and "pharmaceutically effective amount" are synonymous. One of skill in the art can readily determine the proper therapeutic amount.

The term "treating" as used herein includes abrogating, substantially inhibiting, slowing or reversing the progression of a disease or disorder, substantially ameliorating clinical symptoms of a disease or disorder or substantially preventing the appearance of clinical symptoms of a disease or disorder.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

Except where specifically and expressly provided to the contrary, the term "substituted" refers to a structure, e.g., a chemical compound or a moiety on a larger chemical compound, regardless of how the structure was formed. The structure is not limited to a structure made by any specific method.

"Aryl," as used herein, refers to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups that may include from zero to four heteroatoms, for example, benzene, naphthalene, anthracene, phenanthrene, chrysene, pyrene, corannulene, coronene, etc.

"Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, $—CH_2—CF_3$, $—CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl bydefinition. Examples of heterocycles include, but are not limited to piperazinyl, piperidinyl, piperidonyl, 4-piperidonyl, dihydrofuro[2,3-b] tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl."

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, $—CH_2—CF_3$, $—CCl_3$), —CN, aryl, heteroaryl, and combinations thereof.

"Alkyl," as used herein, refers to the radical of saturated aliphatic groups, including straight-chain alkyl, branched-chain alkyl, cycloalkyl (alicyclic), alkyl substituted cycloalkyl groups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfoxide, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; $—NO_2$; —COOH; carboxylate; —COR, —COOR, or $—CON(R)_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as $—CF_3$, $—CH_2—CF_3$, $—CCl_3$); —CN; $—NCOCOCH_2CH_2$, —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl, sulfoxide and sulfonate), and silyl groups, as well as ethers, alkylthios, carbonyls (including ketones, aldehydes, carboxylates, and esters), haloalkyls, —CN and the like. Cycloalkyls can be substituted in the same manner.

The terms "alkenyl" and "alkynyl" refer to unsaturated aliphatic groups analogous in length and possible substitution to the alkyls described above, but that contain at least one double or triple bond respectively.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Amino" and "Amine," as used herein, are art-recognized and refer to both substituted and unsubstituted amines, e.g., a moiety that can be represented by the general formula:

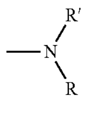 or 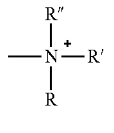

wherein, R, R', and R" each independently represent a hydrogen, substituted or unsubstituted alkyl, substituted or unsubstituted alkenyl, substituted or unsubstituted alkynyl, substituted or unsubstituted carbonyl, $—(CH_2)_m—R'''$, or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or $—(CH_2)_m—R'''$. Thus, the term 'alkylamine' as used herein refers to an amine group, as defined above, having a substituted or unsubstituted alkyl attached thereto (i.e. at least one of R, R', or R" is an alkyl group).

"Carbonyl," as used herein, is art-recognized and includes such moieties as can be represented by the general formula:

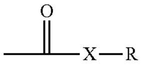 or 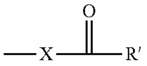

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $—(CH_2)_m—R''$, or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or $—(CH_2)_m—R''$; R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defined as above, the moiety is also referred to as a carboxyl group. When X is oxygen and R is hydrogen, the formula represents a 'carboxylic acid.' Where X is oxygen and R' is hydrogen, the formula represents a 'formate.' Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

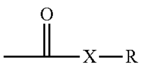 or 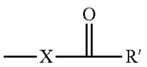

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "carboxyl" is as defined above for the formula

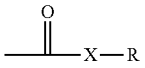 or 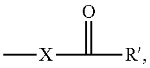, and is defined more specifically by the formula $—R^{iv}COOH$, wherein $R^{iv}$ is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in $R^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

The terms "alkoxyl" or "alkoxy," "aroxy" or "aryloxy," generally describe compounds represented by the formula $—OR^v$, wherein $R^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylalkyl," as used herein, refers to an alkyl group that is substituted with a substituted or unsubstituted aryl or heteroaryl group.

"Alkylaryl," as used herein, refers to an aryl group (e.g., an aromatic or hetero aromatic group), substituted with a substituted or unsubstituted alkyl group.

The terms "amide" or "amido" are used interchangeably, refer to both "unsubstituted amido" and "substituted amido" and are represented by the general formula:

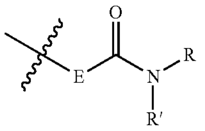

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' each independently represent a hydrogen atom, substituted or unsubstituted alkyl, a substituted or unsubstituted alkenyl, or $-(CH_2)_m-R'''$. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

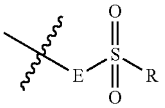

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of E and R can be substituted or unsubstituted amine, to form a "sulfonamide" or "sulfonamido." The substituted or unsubstituted amine is as defined above.

The term "substituted sulfonyl" represents a sulfonyl in which E and R are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $—(CH_2)_m—R'''$, R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

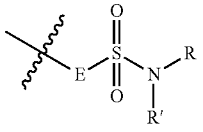

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $—(CH_2)_m—R'''$, or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide.

The term "sulfoxide" is represented by the formula

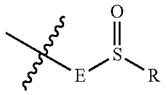

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $—(CH_2)_m—R'''$, or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "phosphonyl" is represented by the formula

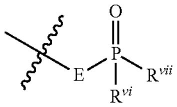

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, $R^{vi}$ and $R^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $—(CH_2)_m—R'''$, or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, $R^{vi}$ and $R^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phosphoryl" defines a phoshonyl in which E is absent, oxygen, alkoxy, aroxy, substituted alkoxy or substituted aroxy, as defined above, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

II. Compositions

A. Senolytic Prodrug Compounds

Senolytic prodrugs disclosed herein are based on a selective design of cytotoxic agents to introduce a site cleavable by SA-β-gal following delivery of the prodrug in vivo, to release the active parent cytotoxic agent for preferentially killing senescent cells.

In a preferred embodiment, the cytotoxic agent lacks a phenol group. A particularly preferred cytotoxic agent is gemcitabine.

Accordingly, the prodrug compounds disclosed therein include, a cytotoxic agent, exemplified herein with gemcitabine modified for cleavage by SA-β-gal. The cytotoxic agent is modified to include a galactose-based moiety, which is preferably acetylated and a benzyloxycarbonyl group as exemplified below for SSK1. Thus, in preferred embodiments, the prodrug does not include free hydroxyl groups (—OH) on the galactose-based moiety. In some embodiments, the prodrug may include modification(s) (e.g., removal of nitro group(s) (such as —$NO_2$) on the aryl or heteroaryl (e.g., phenyl) of the benzyloxycarbonyl moiety or addition of other functional group(s) thereon) to reduce its potential immunogenicity. In some embodiments, the prodrug may include nitro group(s) (such as —$NO_2$) on the aryl or heteroaryl (e.g., phenyl) of the benzyloxycarbonyl moiety, which may, e.g., affect efficiency of the prodrug to produce the cytotoxic agent after activation by β-galactosidase. In some embodiments, the prodrug may include further modification(s) (e.g., removal of one or more of the protecting groups (e.g., acetyl (Ac) groups) from the galactose based-moiety) to increase its water solubility, which may, e.g., facilitate formation of a stable crystal form, simplify the metabolic pathway in vivo, and/or obtain better drug-like properties.

In some forms, the benzyloxycarbonyl moiety has the structure shown below:

Formula I

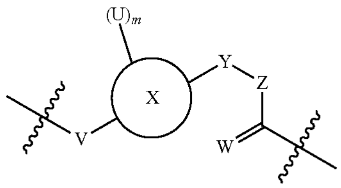

wherein:

X is aryl or heteroaryl, preferably $C_6$ aryl, such as phenyl,

V is O, S, or $NR_1'$, wherein $R_1'$ is hydrogen, substituted $C_1$-$C_5$ alkyl, unsubstituted $C_1$-$C_5$ alkyl, substituted $C_6$-$C_{10}$ aryl, or unsubstituted $C_6$-$C_{10}$ aryl, wherein preferably, V is O, Y is substituted $C_1$-$C_5$ alkylene, unsubstituted $C_1$-$C_5$ alkylene, unsubstituted $C_1$ alkylene, substituted $C_1$ alkylene, unsubstituted $C_2$ alkylene, substituted $C_2$ alkylene, unsubstituted $C_3$ alkylene, substituted $C_3$ alkylene, unsubstituted $C_4$ alkylene, substituted $C_4$ alkylene, unsubstituted $C_1$ alkylene, substituted $C_5$ alkylene, wherein preferably, Y is methylene, Z is O, S, or $NR_2'$, wherein $R_2'$ is hydrogen, substituted $C_1$-$C_5$ alkyl, unsubstituted $C_1$-$C_5$ alkyl, substituted $C_6$-$C_{10}$ aryl, or unsubstituted $C_6$-$C_{10}$ aryl, wherein preferably, Z is O, W is O, S, or $NR_3'$, wherein $R_3'$ is hydrogen, substituted $C_1$-$C_5$ alkyl, unsubstituted $C_1$-$C_5$ alkyl, substituted $C_6$-$C_{10}$ aryl, or unsubstituted $C_6$-$C_{10}$ aryl, wherein preferably, W is O, each U is independently nitro- (such as —$NO_2$), cyano (such as —CN), amino (such as —$NH_2$), hydroxy (—OH), thiol (—SH), halogen (e.g. F, Cl, I, Br), alkoxy, alkylamino, dialkylamino, substituted alkoxy, carboxyl, carbonyl, substituted carbonyl, amido, sulfonyl, sulfonic acid, phosphoryl, phosphonyl, phosphonyl, hydrogen, alkyl, substituted alkyl, wherein preferably, U is —$NO_2$ or hydrogen, and m is an integer between 0 and 10, inclusive, such as 0, 1, 2, 3, 4, 5, 6, 7, 8, 9, and 10, as valency permits.

In some forms of Formula I, X is $C_6$ aryl. In some forms, U is —$NO_2$. In some forms, U is hydrogen. In some forms, V is O. In some forms of Formula I, W is O. In some forms, Y is substituted $C_1$ alkylene. In some forms of Formula I, Y is substituted $C_1$ alkylene. In some forms, Z is O.

In some forms of Formula I, X is $C_6$ aryl, Y is substituted $C_1$ alkylene or substituted $C_1$ alkylene. In some forms of Formula I, X is $C_6$ aryl, Y is substituted $C_1$ alkylene or substituted $C_1$ alkylene, V and W are O.

In some forms of Formula I, X is $C_6$ aryl, Y is substituted $C_1$ alkylene or substituted $C_1$ alkylene, V, Z, and W are O.

In some forms of Formula I, the benzyloxycarbonyl is Formula II, shown below:

Formula II

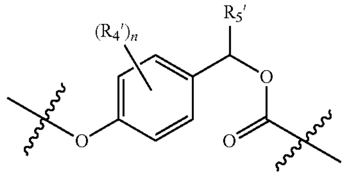

wherein:

each $R_4'$ is independently nitro- (such as —$NO_2$), cyano (such as —CN), amino (such as —$NH_2$), hydroxy (—OH), thiol (—SH), halogen (e.g. F, Cl, I, Br), alkoxy, alkylamino, dialkylamino, substituted alkoxy, carboxyl, carbonyl, substituted carbonyl, amido, sulfonyl, sulfonic acid, phosphoryl, phosphonyl, phosphonyl, hydrogen, alkyl, substituted alkyl, wherein preferably, $R_4'$ is —$NO_2$ or hydrogen, $R_5'$ is hydrogen, nitro- (such as —$NO_2$), cyano (such as —CN), isocyano (such as), amino (such as —$NH_2$), hydroxy (—OH), thiol (—SH), halogen (e.g. F, Cl, I, Br), alkoxy, alkylamino, dialkylamino, substituted alkoxy, carboxyl, carbonyl, substituted carbonyl, amido, sulfonyl, sulfonic acid, phosphoryl, phosphonyl, phosphonyl, hydrogen, alkyl, substituted alkyl, wherein preferably, $R_5'$ is hydrogen, and n is an integer between 0 and 4, inclusive, such as 0, 1, 2, 3, and 4, as valency permits.

In some forms of Formula II, at least one $R_4'$ is nitro- (such as —$NO_2$), cyano (such as —CN), amino (such as —$NH_2$), hydroxy (—OH), thiol (—SH), halogen (e.g. F, Cl, I, Br), alkoxy, alkylamino, dialkylamino, substituted alkoxy, carboxyl, carbonyl, substituted carbonyl, amido, sulfonyl, sulfonic acid, phosphoryl, phosphonyl, or phosphonyl. In some forms of Formula II, at least one $R_4'$ is nitro- (such as —$NO_2$), cyano (such as —CN), isocyano (such as), amino (such as —$NH_2$), hydroxy (—OH), thiol (—SH), hydrogen, or halogen (e.g. F, Cl, I, Br). In some forms of Formula II, at least one $R_4'$ is nitro- (such as —$NO_2$). In some forms of Formula II, at least one $R_4'$ is nitro- (such as —$NO_2$), which may e.g., increase efficiency to produce a cytotoxic agent after activation. In some forms of Formula II, at least one $R_4'$ is hydrogen (instead of a nitro group (such as —$NO_2$)), which may e.g., reduce potential immunogenicity.

In some forms of Formula II, $R_5'$ is hydrogen, alkyl, or substituted alkyl. In some forms of Formula II, $R_5'$ is hydrogen.

In some forms the compound includes a galactose based-moiety of the structure shown below.

Formula III

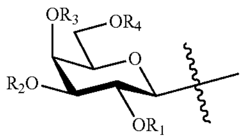

$R_1$, $R_2$, $R_3$, and $R_4$ could each/independently be H or any substituent that could be hydrolyzed inside the cell. Preferably in some forms, $R_1$, $R_2$, $R_3$, and $R_4$ are each hydrogen or substituents such that —$OR_1$, —$OR_2$, —$OR_3$, and/or —$OR_4$ can be hydrolyzed inside a cell. In some forms, $R_1$, $R_2$, $R_3$, and $R_4$ are independently H, $R_5C(O)$—, $R_6OC(O)$—, $R_7R_8NC(O)$—, or $R_9PO_3^-$—, such that —$OR_x$ is independently an ester, a carbonate, a carbamate, or a phosphodiester group, respectively, where x is 1, 2, 3, or 4. In some forms, $R_1$, $R_2$, $R_3$, and $R_4$ are independently $R_5C(O)$—, $R_6OC(O)$—, $R_7R_8NC(O)$—. In these forms, $R_5$, $R_6$, $R_7$, $R_8$, and $R_9$ are independently hydrogen, substituted alkyl, unsubstituted alkyl, substituted aryl, unsubstituted aryl, substituted heteroaryl, unsubstituted heteroaryl, substituted $C_3$-$C_{10}$ cyclyl, unsubstituted $C_3$-$C_{10}$ cyclyl, substituted $C_3$-$C_{10}$ heterocyclyl, unsubstituted $C_3$-$C_{10}$ heterocyclyl. In these forms, $R_5$, $R_6$, $R_7$, $R_8$, and $R_9$ are independently hydrogen, substituted $C_1$-$C_5$ alkyl, unsubstituted $C_1$-$C_5$ alkyl, substituted $C_6$-$C_{10}$ aryl, unsubstituted $C_6$-$C_{10}$ aryl, substituted $C_6$-$C_{10}$ heteroaryl, unsubstituted $C_6$-$C_{10}$ heteroaryl, substituted $C_3$-$C_{10}$ cyclyl, unsubstituted $C_3$-$C_{10}$ cyclyl, or substituted $C_3$-$C_{10}$ heterocyclyl, unsubstituted $C_3$-$C_{10}$ heterocyclyl. In these forms, $R_5$, $R_6$, $R_7$, $R_8$, and $R_9$ are independently hydrogen, substituted $C_1$-$C_3$ alkyl, unsubstituted $C_1$-$C_3$ alkyl, substituted $C_6$ aryl, unsubstituted $C_6$ aryl, substituted $C_6$ heteroaryl, unsubstituted $C_6$ heteroaryl, substituted $C_6$ cyclyl, unsubstituted $C_6$ cyclyl, or substituted $C_6$ heterocyclyl, unsubstituted $C_6$ heterocyclyl. In some forms, one or more (or all) of $R_1$, $R_2$, $R_3$, and $R_4$ could be H, which may, e.g., increase water solubility, facilitate formation of a stable crystal form, simplify the metabolic pathway in vivo, and/or obtain better drug-like properties. In some forms, e.g., when the prodrug is in a crystal form, one or more (or all) of $R_1$, $R_2$, $R_3$, and $R_4$ are H.

In some forms, $R_1$, $R_2$, $R_3$, and $R_4$ are $R_5C(O)$—. In these forms, $R_5$ is independently substituted $C_1$-$C_3$ alkyl or unsubstituted $C_1$-$C_3$ alkyl. In these forms, $R_5$ is, preferably, methyl.

A preferred galactose-based moiety is a D-galactose tetraacetate moiety, shown below.

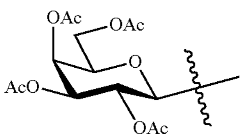

In some forms, one or more (e.g., two, three, or four) of the protecting groups (e.g., acetyl (Ac) groups) may be removed from the galactose based-moiety. In some embodiments, removal of one or more (e.g., two, three, or four) of the protecting groups may increase water solubility, facilitate formation of a stable crystal form, simplify the metabolic pathway in vivo, and/or obtain better drug-like properties. In some embodiments, the prodrug may be in a crystal form, which may, e.g., do not contain protecting groups (e.g., acetyl (Ac) groups) or comprises a reduced number of protecting groups (e.g., acetyl (Ac) groups) on the galactose based-moiety. In some forms, e.g., when the prodrug is in a crystal form, one or more (or all) of $R_1$, $R_2$, $R_3$, and $R_4$ are H.

In some forms, the agent is represented by

Formula IV

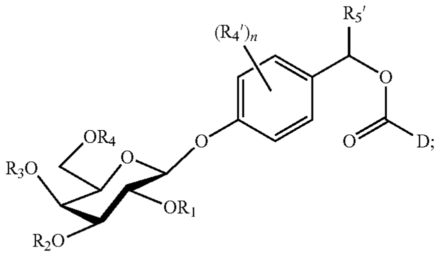

Where D comprises a cytotoxic agent. In some forms, one or more (e.g., two, three, or four) of the protecting groups (e.g., acetyl (Ac) groups) may be removed from the galactose based-moiety. In some forms, e.g., when the prodrug is in a crystal form, one or more (or all) of $R_1$, $R_2$, $R_3$, and $R_4$ are H. In some forms, $R_4$' may be nitro- (such as —$NO_2$). In some forms, $R_4$' may be hydrogen (instead of e.g., a nitro group (such as —$NO_2$)). Preferred cytotoxic agents are chemotherapeutic agents/drugs which are known in the art. Examples of chemotherapeutic agents include, but are not limited to gemcitabine, cytarabine, 5'-Deoxy-5-fluorocytidine, mercaptopurine, Sapacitabine, nelarabine, clofarabine, decitabine, and azacitidine, methotrexate, vinblastine, doxorubicin, ifosfamide, pemetrexed, cisplatin, carboplatin, and paclitaxel. Chemotherapeutic agents with short plasma circulation times such as gemcitabine, are preferred. Thus, derivatives of parent pharmaceuticals which have been modified to prolong their plasma circulation time are not preferred, for example, pegylated derivatives. Particularly preferred are chemotherapeutic agents lacking a phenolic group. Examples of cytotoxic agents that can be used to make the senolytic prodrugs disclosed herein include, but are not limited to gemcitabine, cytarabine, and 5'-Deoxy-5-fluorocytidine, mercaptopurine, Sapacitabine, nelarabine, clofarabine, decitabine, and azacitidine. In some preferred embodiments, the xytotoxic agent is not quercetin or panobinostat.

$R_1$, $R_2$, $R_3$, and $R_4$ are as described above for Formula III, and $R_4$' and $R_5$' are as described above for Formula II.

A particularly preferred benzyloxycarbonyl group is shown below.

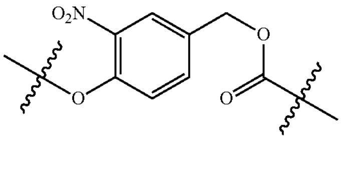 [SMILES: *Oc1ccc(COC(*)=O)cc1[N+](=O)[O-]]

3-nitro-4-oxy-benzyl Carboxy Group

In some forms, $NO_2$ may be removed from the above group.

A particularly preferred compound is shown below.

SSK1

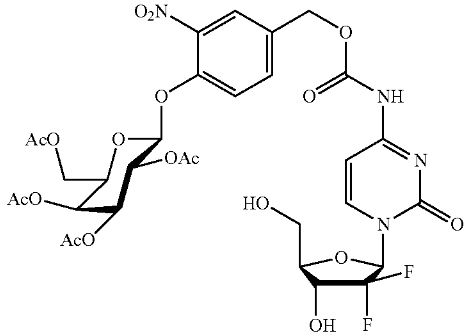

In some forms, one or more (e.g., two, three, or four) of the protecting groups (e.g., acetyl (Ac) groups) may be removed from the galactose based-moiety. Accordingly, another preferred compound is shown below.

SSK2

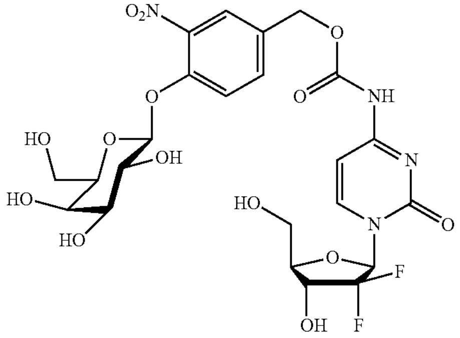

In some forms, $NO_2$ may be removed and another preferred compound is shown below.

SSK3

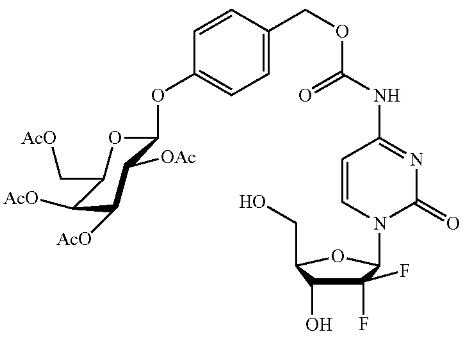

In some forms, both $NO_2$ and one or more (e.g., two, three, or four) of the protecting groups (e.g., acetyl (Ac) groups) may be removed and another preferred compound is shown below.

SSK4

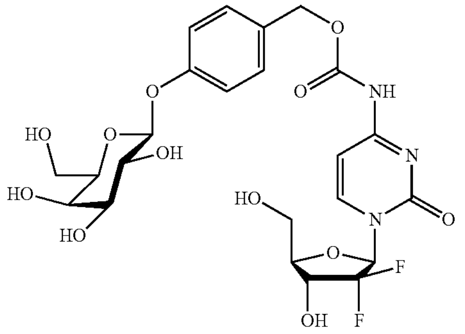

Unlike galactose-modified duorcarmycins which have a phenolic or hydroxyl group for direct conjugation of a galactose moiety to the duocarmycin compound, cytotoxic agents such as gemcitabine, cytarabine, and 5'-Deoxy-5-fluorocytidine which lack the phenolic or hydroxyl functional group are not amenable to direct modification with a galactose modification for at least the reason that direct attachment of a galactose moiety to amine groups for example may result either in an unstable compound or a prodrug that is not cleaved or is poorly cleaved by SA-β-gal. Thus, in one preferred the prodrugs disclosed herein do not include a direct conjugation of a galactose moiety to any group on the cytotoxic agent.

Thus the disclosed prodrug compounds are based on a selective and specific design of preferably, non-phenolic cytotoxic agents for (i) increased cellular permeability and (ii) improved cleavage by SA-β-gal. A proposed scheme is release of the active agent from the prodrug is exemplified below for SSK1.

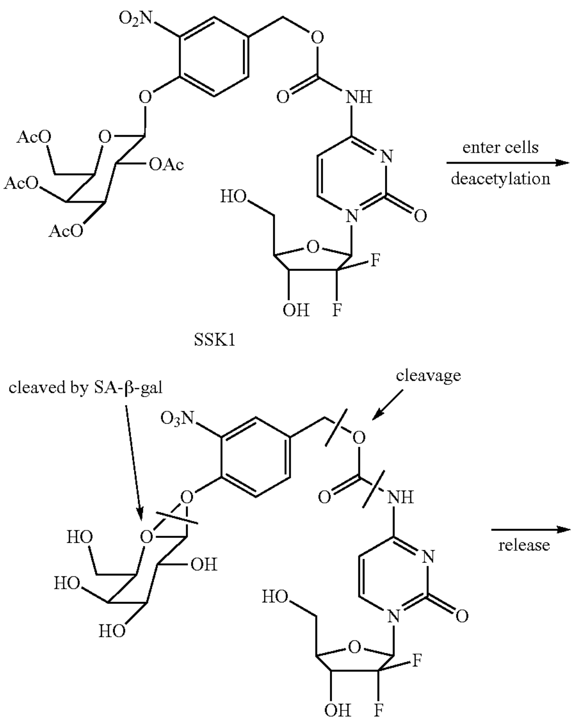

-continued

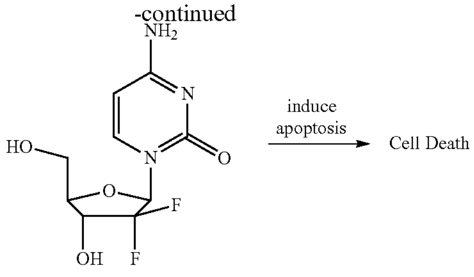

gemcitabine

B. Formulations

The compounds described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

The compounds are included in the formulations in a therapeutically effect amount. A therapeutically effective amount can be estimated initially from cell culture assays. For example, a dose can be formulated in animal models to achieve a circulating concentration range that includes the IC50 or the IC10o as determined in cell culture. Such information can be used to more accurately determine useful doses in humans. Initial dosages can also be estimated from in vivo data. Using these initial guidelines one of ordinary skill in the art could determine an effective dosage in humans.

1. Parenteral Formulations

The compounds described herein can be formulated for parenteral administration.

For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

(a). Controlled Release Formulations

The parenteral formulations described herein can be formulated for controlled release including immediate release, delayed release, extended release, pulsatile release, and combinations thereof.

1. Nano- and Microparticles

For parenteral administration, the one or more compounds, and optional one or more additional active agents, can be incorporated into microparticles, nanoparticles, or combinations thereof that provide controlled release of the compounds and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, can also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents can be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethyl-cellulose) alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

2. Method of making Nano- and Microparticles

Encapsulation or incorporation of drug into carrier materials to produce drug-containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug-containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

(b). Injectable/Implantable Formulations

The compounds described herein can be incorporated into injectable/implantable solid or semi-solid implants, such as polymeric implants. In one embodiment, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

2. Enteral Formulations

Suitable oral dosage forms include tablets, capsules, solutions, suspensions, syrups, and lozenges. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

"Diluents", also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

"Binders" are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

"Lubricants" are used to facilitate tablet manufacture. Examples of suitable lubricants include, but are not limited to, magnesium stearate, calcium stearate, stearic acid, glycerol behenate, polyethylene glycol, talc, and mineral oil.

"Disintegrants" are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

"Stabilizers" are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

(a) Controlled Release Enteral Formulations

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

(i) Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename EUDRAGIT t®. In further preferred embodiments, the acrylic polymer comprises a mixture of two acrylic resin lacquers commercially available from Rohm Pharma under the tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT® RL, 50% EUDRAGIT® RL and 50% EUDRAGIT t® RS, and 10% EUDRAGIT® RL and 90% EUDRAGIT® RS. One skilled in the art will recognize that other acrylic polymers may also be used, such as, for example, EUDRAGIT® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

(ii). Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

3. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The compounds can also be formulated for intranasal delivery, pulmonary delivery, or inhalation. The compositions may further contain one or more chemical penetration enhancers, membrane permeability agents, membrane transport agents, emollients, surfactants, stabilizers, buffers, and combination thereof.

In certain embodiments, it may be desirable to provide continuous delivery of one or more compounds to a patient in need thereof. For topical applications, repeated application can be done or a patch can be used to provide continuous administration of the compounds over an extended period of time "Buffers" are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

"Penetration enhancers" are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

"Preservatives" can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

(a). Emulsions

An emulsion is a preparation of one liquid distributed in small globules throughout the body of a second liquid. In particular embodiments, the non-miscible components of the emulsion include a lipophilic component and an aqueous component. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

(b). Lotions

A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

(c). Creams

Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments, as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

(d). Ointments

Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

(e). Gels

Gels are semisolid systems containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

(f). Foams

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227). The propellants preferably are not hydrocarbon propellant gases, which can produce flammable or explosive vapors during spraying. Furthermore, the compositions preferably contain no volatile alcohols, which can produce flammable or explosive vapors during use.

III. Methods of Making and Using

Thus the disclosed compositions can be used to treat senescence-associated disorders and disorders associated with aberrant inflammation, in a subject in need thereof. Preferably, the subject is a mammal, more preferably a human. As used herein, senescence-associated disorders or diseases include disorders or diseases associated with, or caused by cellular senescence, including age-related diseases and disorders. A senescence-associated disease or disorder may also be called a senescent cell-associated disease or disorder.

Senescence is a cellular response characterized by a stable growth arrest and other phenotypic alterations that include a proinflammatory secretome. Senescence plays roles in normal development, maintains tissue homeostasis, and limits tumor progression. However, senescence has also been implicated as a major cause of age-related disease. Senescent cells accumulate during age and are associated with many diseases, including cancer, fibrosis and many age-related pathologies. Recent evidence suggests that senescent cells are detrimental in multiple pathologies and their elimination confers many advantages, ameliorating multiple pathologies and increasing healthspan and lifespan.

Senescent cells are present in many pre-neoplastic lesions, fibrotic tissues (e.g. in the liver, kidney, heart, pancreas) and old tissues.

While SA-β-gal is widely used as a marker of cellular senescence (Childs et al., *Nat Med,* 21(12), 1424-1435 (2015); Hernandez-Segura et al., *Trends Cell Biol,* 28(6), 436-453(2018); Sharpless & Sherr, *Nat Rev Cancer,* 15(7), 397-408(2015)), its elevated activity can be found in some non-senescent cells such as activated macrophages (Bursuker, Rhodes, & Goldman, J Cell Physiol 112, 385-390 (1982); Frescas et al., Cell Cycle 16, 1526-1533(2017)). These SA-β-gal positive macrophages can be harmful and have been found to accumulate in injured and aged tissues contributing to chronic inflammation (Hall et al., Aging (Albany NY) 8, 1294-1315(2016); Oishi & Manabe, NPJ Aging Mech Dis 2, 16018(2016)). Importantly, the data in this application shows that SSK1 decreases the number of SA-β-gal positive macrophages in injured lungs and aged livers, which is consistent with the observation of reduced secretion of chronic inflammation-related cytokines. Therefore, eliminating macrophage accumulation by modulating SSK1 might reduce chronic inflammation and benefit aged organisms. In addition, activated macrophages have crucial roles in acute inflammation and cytokine storm (Hamidzadeh et al., Annu Rev Physiol 79, 567-592(2017)), especially those induced by virus infection. During virus-induced acute inflammation, macrophages produce pro-inflammatory factors and trigger initiation of cytokine storms (Hamidzadeh et al., Annu Rev Physiol 79, 567-592(2017)). The depletion of macrophages could protect mice from coronavirus-induced lethal infection (Channappanavar et al., Cell Host Microbe 19, 181-193(2016)). Accordingly, activated macrophages can be targeted using the compounds and formulatons disclosed herein, to treating acute inflammation and cytokine storms via SSK1. In these embodiments, the compositions are administered in an effective reduce the amount of macrophages in the subject, particularly, SA-β-gal positive macrophages.

Viral Disorders

The disclosed compositions can be used to ameliorate the symptoms associated with abberrant cytokine production, as a result of virus-induced inflammation. Exemplary viral infections during which a subject can benefit from administration of effective amounts of the formulations disclosed herein include coronaviruses, for example, coronaviruses, for example, Severe Acute Respiratory Syndrome (SARS) coronaviruses (CoV), SARS-CoV-2 (which causes COVID-19 (Coronavirus Disease 2019)), and a Middle East respiratory syndrome (MERS)-CoV. The SARS-CoV-2 virus is a betacoronavirus, like MERS-CoV and SARS-CoV. These highly pathogenic human respiratory coronaviruses cause acute lethal disease characterized by inflammatory responses and lung damage. Robust replication opf SARS-CoV accompanied by delayed type I interferon (IFN-I) signaling orchestrates inflammatory responses and lung immunopathology with diminished survival. IFN-I remains detectable until after virus titers peak but early IFN-I administration ameliorates immunopathology. This delayed IFN-I signaling promotes the accumulation of pathogenic inflammatory monocyte-macrophages (IMMs), resulting in elevated lung cytokine/chemokine levels, vascular leakage and impaired virus-specific T cell responses. Accumulating evidence suggests that a subgroup of patients with severe coronavirus disease 2019 (COVID-19) might have a cytokine storm syndrome (Mehta, et al., DOI:https://doi.org/10.1016/S0140-6736(20)30628-0).

The compositions are administered in an effective amount to reduce the levels of one or more macrophages in the subject. In a particularly preferred embodiment, the disclosed compositions are administered to a subject infected with a coronavirus, preferably, SARS-CoV or SARS Coronavirus 2 (Sars-CoV-2).

Cancer and Cancer Therapeutic Applications

Studies have shown through the SASP (senescence-associated secretory phenotype), aged tissues provide a supportive niche for cancer. Senescent cells can contribute to tumor progression by enhancing the proliferative potential of cancer cells or contributing to epithelial to mesenchymal transition. Therefore, the increased numbers of senescent cells present in aged tissues could contribute to the increased incidence of cancer with age. Supporting this, a delayed onset in tumor formation is observed when senescent cells are eliminated. Senolytic therapy also reduces the incidence of metastasis, the leading cause of cancer-related deaths. (Reviewed in McHugh, et al., J. Cell Biol., 217(1):65-77 (2018).

In some embodiments, the compositions disclosed herein can be used in combination with cancer therapeutics. Thus, in some preferred embodiments, the subject being treated has been diagnosed with cancer. Non-limiting examples of cancers which may be treated according to this aspect of the invention include: adenocarcinoma, adrenal gland tumor, ameloblastoma, anaplastic, anaplastic carcinoma of the thyroid, angiofibroma, angioma, angiosarcoma, apudoma, argentaffmoma, arrhenoblastoma, ascites tumor cell, ascitic tumor, astroblastoma, astrocytoma, ataxia-telangiectasia, atrial myxoma, a basal cell carcinoma cell, bone cancer, brainstem glioma, brain tumor, breast cancer, Burkitt's lymphoma, cerebellar astrocytoma, cervical cancer, cherry angioma, cholangiocarcinoma, cholangioma, chondroblastoma, chondroma, chondrosarcoma, chorioblastoma, choriocarcinoma, colon cancer, common acute lymphoblastic leukemia, craniopharyngioma, cystocarcinoma, cystofbroma, cystoma, ductal carcinoma in situ, ductal papilloma, dysgerminoma, encephaloma, endometrial carcinoma, endothelioma, ependymoma, epithelioma, erythroleukemia, Ewing's sarcoma, extra nodal lymphoma, feline sarcoma, fibro adenoma, fibro sarcoma, follicular cancer of the thyroid, ganglioglioma, gastrinoma cell, glioblastoma multiform, glioma, gonadoblastoma, haemangioblastoma, haemangioendothelioblastoma, haemangioendothelioma, haemangiopericytoma, haematolymphangioma, haemocytoblastoma, haemocytoma, hairy cell leukemia, hamartoma, hepatocarcinoma, hepatocellular carcinoma, hepatoma, histoma, Hodgkin's disease, hypernephroma, infiltrating cancer, infiltrating ductal cell carcinoma, insulinoma, juvenile angioforoma, Kaposi sarcoma, kidney tumor, large cell lymphoma, leukemia, a leukemia, acute leukemia, lipoma, liver cancer, liver metastases, Lucke carcinoma, lymphadenoma, lymphangioma, lymphocytic leukemia, lymphocytic lymphoma, lymphoeytoma, lymphoedema, lymphoma, lung cancer, malignant mesothelioma, malignant teratoma, mastocytoma, medulloblastome, melanoma, meningioma, mesothelioma, Morton's neuroma, multiple myeloma, myeloblastoma, myeloid leukemia, myelolipoma, myeloma, myoblastoma, myxoma, nasopharyngeal carcinoma, neoplastic, nephroblastoma, neuroblastoma, neurofibroma, neurofibromatosis, neuroglioma, neuroma, non-Hodgkin's lymphoma, oligodendroglioma, optic glioma, osteochondroma, osteogenic sarcoma, osteosarcoma, ovarian cancer, Paget's disease of the nipple, pancoast tumor, pancreatic cancer, phaeochromocytoma, pheoehromocytoma, plasmacytoma, primary brain tumor, progonoma, prolactinoma, renal cell carcinoma, retinoblastoma, rhabdomyosarcoma, rhabdo sarcoma, a solid tumor, sarcoma, a secondary tumor, seminoma, skin cancer, small cell carcinoma, squamous eel! carcinoma, strawberry haemangioma, T-cell lymphoma, teratoma, testicular cancer, thymoma, trophoblastic tumor, Wilm's tumor.

In one preferred embodiment, the disclosed senolytic prodrugs are used in conjunction with other treatments for cancer that induce senescence, such as irradiation or chemotherapy (for example, treatment with Palbociclib, ribociclib or abemaciclib, or other chemotherapeutic agents). Thus, by treating at the same time, or after the other treatment, the agent can: (a) eliminate cancer cells that have been pushed to senescence; and/or eliminate or reduce certain side effects produced by senescent cells such as inflammation, promotion of cancer growth, promotion of metastasis and other side effects of chemotherapy or radiotherapy; and/or (b) reduce or eliminate precancerous lesions; and/or (c) eliminate or reduce cells that Undergo senescence by treatment with CDK4/6 inhibitors. The disclosed agents can reduce or eliminate precancerous (or preneoplastic) lesions. Senescent cells exist in premalignant tumors. In this regard, it is understood that a substantial number of cells in premalignant tumors undergo oncogene-induced senescence. Thus, the disclosed agents can be used to reduce or eliminate precancerous (or pre-neoplastic) lesions.

In another preferred embodiment, the disclosed senolytic prodrugs are administered to eliminate or reduce chemotherapy-induced senescence, for example, before, during or after treatment with a chemotherapeutic agent. Thus, in one preferred embodiment, the agent can be used in combination treatment with a chemotherapeutic agent, where the agent is administered separately, sequentially or concomitantly with the chemotherapeutic agent. Exemplary chemotherapeutic agents include, but are not limited to, anthracyclines, doxorubicin, etoposide, daunorubicin, taxols, paclitaxel, gemcitabine, pomaiidomide, and lenaiidomide. The disclosed senolytic prodrugs can eliminate or reduce senescence induced by treatment with a CDK inhibitor, for example, a CDK4 or CDK6 inhibitor. Thus, in one preferred embodiment, the disclosed senolytic prodrugs can be used in combination treatment with a CDK4 or CDK6 inhibitor, where the agent is administered separately, sequentially or concomitantly with the CDK4 or CDK6 inhibitor. The disclosed senolytic prodrugs can eliminate or reduce Palbociclib-induced senescence. In the context of eliminating or reducing Palbociclib-induced senescence, administration of the agent can potentially prevent cancer remission as cells reenter the cell cycle. In another preferred embodiment, the agent can eliminate cancer cells that have been pushed to senescence. In one preferred embodiment, the agent delays tumorigenesis.

In another preferred embodiment, the disclosed senolytic prodrugs can reduce certain side effects produced by senescent cells such as inflammation, promotion of cancer growth, promotion of metastasis and other side effects of chemotherapy or radiotherapy.

Chemotherapy-induced side effects or radiotherapy-induced side effects include, but art not limited to, weight loss, endocrine changes, hormone imbalance, changes in hormone signaling, changes is cardiotoxicity, body composition, reduced ability to be physically active, gastrointestinal toxicity, nausea, vomiting, constipation, anorexia, diarrhea, peripheral neuropathy, fatigue, malaise, low physical activity, hematological toxicity, anemia, hepatotoxicity, alopecia, pain, infection, mucositis, fluid retention, dermatological toxicity, rashes, dermatitis, hyperpigmentation, urticaria, photosensitivity, nail changes, mouth, gum or throat problems, and any toxic side effect caused by a chemotherapy or radiotherapy. Thus, in one preferred embodiment, the agent can be used in combination treatment with a chemotherapeutic agent, where the agent is administered separately, sequentially or concomitantly with the chemotherapeutic agent. Likewise, the agent can be used in combination treatment with radiotherapy, where the agent is administered before, during or after radiotherapy. Another embodiment of the invention relates to an agent as described herein for use in reducing or alleviating one or more chemotherapy-induced or radiotherapy-induced side effects.

In some embodiments, methods for treating or reducing the likelihood of metastasis comprising administering an agent described herein during an off-chemotherapy or off-radiotherapy time interval or after the chemotherapy or radiotherapy treatment regimen has been completed, are provided. Another embodiment of the invention relates to an agent as described herein for use in treating or reducing the likelihood of metastasis.

In one preferred embodiment, the disclosed senolytic prodrugs can be used in the treatment of chronic or long-term chemotherapy-induced or radiotherapy-induced side effects. Certain toxic effects can appear long after treatment and can result from damage to an organ or system by the therapy. Organ dysfunction, for example, neurological, pulmonary, cardiovascular, and endocrine dysfunction, can be observed in subjects who were treated for cancers during childhood. Chronic or late toxic side effects that occur in subjects who received chemotherapy or radiation therapy include, for example, cardiomyopathy, congestive heart disease, inflammation, early menopause, osteoporosis, infertility, impaired cognitive function, peripheral neuropathy, secondary cancers, cataracts and other vision problems, hearing loss, chronic fatigue, reduced lung capacity, and lung disease.

Non-Cancer/Cancer Therapeutic Applications

In other preferred embodiments, the subject has not been diagnosed with cancer and is not being treated for cancer. In these embodiments, the disclosed compositions are administered to decrease the senescent cell population in a subject in need thereof.

Senescent cells are associated with a long list of other pathologies, including neurological (e.g. brain aneurysm, Alzheimer's and Parkinson), pulmonary (e.g. idiopathic pulmonary fibrosis, chronic obstructive pulmonary disease and cystic fibrosis), ophthalmological (e.g. cataracts, glaucoma, macular degeneration), musculoskeletal (e.g. sarcopenia, disc degeneration, osteoarthritis), cardiovascular (e.g. atherosclerosis, cardiac fibrosis, aorta aneurysm), renal (e.g. chronic kidney disease, transplant complications), osteoarthritis of the knee and others such as diabetes, mucositis, hypertension, liver fibrosis and osteomyelofibrosis (OMF).

A prominent feature of aging is a gradual loss of function, or degeneration that occurs at the molecular, cellular, tissue, and organismal levels. Age-related degeneration gives rise to well-recognized pathologies such as sarcopenia, atherosclerosis and heart failure, osteoporosis, pulmonary insufficiency, renal failure, neurodegeneration (including macular degeneration, Alzheimer's disease, and Parkinson's disease), and many others. Senescence-associated diseases and disorders include, but are not limited to, cardiovascular diseases and disorders, inflammatory diseases and disorders, autoimmune diseases and disorders, pulmonary diseases and disorders, eye diseases and disorders, metabolic diseases and disorders, neurological diseases and disorders (e.g., neurodegenerative diseases and disorders); age-related diseases and disorders induced by senescence; skin conditions; age-related diseases; dermatological diseases and disorders; and transplant related diseases and disorders.

Diseases Associated with Elevated β-Galactosidase Activity

In another embodiment, the agent can be used in the treatment of a disease or disorder which correlates, or is associated with, elevated β-galactosidase activity. In a preferred embodiment, the elevated β-galactosidase activity is a result of elevated expression of β-galactosidase or over-expression of β-galactosidase activity relative to baseline levels which can be determined by standard methods. Expression of β-galactosidase can be detected in cells by histochemical or immunohistochemcal methods. For example, the senescence marker SA-beta galactosidase (SAβ-Gal) can be detected by known methods (Dimri et al, *Proc. Natl. Acad. Sci. U.S.A.* 92: 9363-9367 (1995)).

In a more preferred embodiment of the invention, the disease is selected from the Wiedemann-Rautenstrauch syndrome of neonatal progeria, the Werner syndrome of adult progeria, Hutchinson-Gilford syndrome, Rothmund Thompson syndrome, Mulviii-Smith syndrome, Cockayne syndrome, Dyskeratosis Congenita, idiopathic pulmonary fibrosis, aplastic anaemia, emphysema, type 2 diabetes, and degeneration of cartilage.

Hutchinson-Gilford Progeria Syndrome ("Progeria", or "HGPS") a rare, fatal genetic condition characterized by an appearance of accelerated aging in children. Although they are born looking healthy, children with Progeria begin to display many characteristics of accelerated aging within the first two years of life. Progeria signs include growth failure, loss of body fat and hair, aged-looking skin, stiffness of joints, hip dislocation, generalized atherosclerosis, cardiovascular (heart) disease and stroke. Other progeroid syndromes include Werner's syndrome, also known as "adult progeria" which does not have an onset until the late teen years. There is no cure for progeria, but occupational and physical therapy can help the child keep moving if their joints are stiff. The disclosed compositions and methods can ameliorate the accelerated ageing symptoms associated with Progeria Syndrome. The examples below demonstrate that show that depletion of L1 RNA in cells obtained from HGPS mouse model (LAKI) using antisense oligonucleotides (AON) restored the levels of epigenetic marks and reduced the expression of senescent-associated genes, and increased life span.

Cardiovascular Disease

In one preferred embodiment of the invention, the senescence-associated disease or disorder is a cardiovascular disease. Examples include, but are not limited to, atherosclerosis, angina, arrhythmia, cardiomyopathy, congestive heart failure, coronary artery disease, carotid artery disease, endocarditis, coronary thrombosis, myocardial infarction, hypertension, aortic aneurysm, cardiac diastolic dysfunction, hypercholesterolemia, hyperiipidemia, mitral valve prolapsed, peripheral vascular disease, cardiac stress resistance, cardiac fibrosis, brain aneurysm and stroke. In one preferred embodiment, the senescence-associated disease or disorder is associated with or caused by atherosclerosis (i.e. hardening of the arteries).

Atherosclerosis is characterized by patchy intimal plaques (atheromas) that encroach on the lumen of medium-sized and large arteries. Administration of an agent according to the invention can reduce the lipid content of an atherosclerotic plaque in a blood vessel of the subject and/or increase the fibrous cap thickness.

Inflammatory and Autoimmune Diseases and Disorders

In one preferred embodiment of the invention, the senescence-associated disease or disorder is an inflammatory or autoimmune disease or disorder. Non-limiting examples of autoimmune diseases include osteoporosis, osteoarthritis, psoriasis, oral mucositis, rheumatoid arthritis, inflammatory bowel disease, eczema, kyphosis (curvature of the spinal column), herniated intervertebral disc, and the pulmonary diseases, COPD and idiopathic pulmonary fibrosis. In one preferred embodiment, the senescence-associated disease or disorder is chronic inflammation.

Chronic inflammation is thought to be the main age-related factor associated with osteoarthritis. In combination with aging, joint overuse and obesity appear to promote osteoarthritis. By selectively killing senescent cell, the agents of the invention can reduce or inhibit loss or erosion of proteoglycan layers in a joint, reduce inflammation in the affected joint, and promote production of collagen. Removal of senescent cells causes a reduction in the amount of inflammatory cytokines, such as IL-6, produced in a joint and inflammation is reduced.

Thus, the senescence-associated disease or disorder can in some embodiments be rheumatoid arthritis. Rheumatoid arthritis is a chronic inflammatory disorder that typically affects the joints in hands and feet.

In other embodiments, the senescence-associated disease or disorder is osteoporosis. Osteoporosis is a progressive bone disease that is characterized by a decrease in bone mass and density that may lead to an increased risk of fracture. Bone mineral density (BMD) is reduced, bone microarchitecture deteriorates, and the amount and variety of proteins in bone are altered. In other embodiments of the invention, the disclosed agents are used in treating herniated intervertebral discs. Subjects with herniated discs exhibit elevated presence of cell senescence in the blood and in vessel walls (Roberts et al. (2006) *Eur. Spine* J. 15 Suppl 3: S312-316).

Neurological Disease or Disorder

In one preferred embodiment of the invention, the senescence-associated disease or disorder is a neurological disease or disorder selected from Alzheimer's disease (and other dementias), Parkinson's disease, Huntington's disease, dementia, mild cognitive impairment (MCI), macular degeneration and motor neuron dysfunction (MND), and diseases and disorders of the eyes, such as age-related macular degeneration.

Parkinson's disease (PD) is a disabling condition of the brain characterized by slowness of movement (bradykinesia), shaking, stiffness, postural instability and loss of balance. Many of these symptoms are due to the loss of certain nerves in the brain, which results in a lack of dopamine. Senescence of dopamine-producing neurons is thought to contribute to the observed ceil death in PD through the production of reactive oxygen species.

Alzheimer's disease (AD) is a neurodegenerative disease that shows a slow progressive mental deterioration with failure of memory, disorientation, and confusion, leading to profound dementia. As the disease progresses, impaired judgment, confusion, behavioral changes, disorientation, and difficulty in walking and swallowing occur. Age is the single greatest predisposing risk factor for developing AD, which is the leading cause of dementia in the elderly (Hebert, et al., *Arch. Neurol.* 60:1 19-1122 (2003)). Early clinical symptoms show remarkable similarity to mild cognitive impairment.

Mild Cognitive Impairment (MCI) is a brain-function syndrome involving the onset and evolution of cognitive impairments beyond those expected based on age and education of the individual, but which are not significant enough to interfere with the individual's daily activities. MCI is an aspect of cognitive aging that is considered to be a transitional state between normal aging and the dementia into which it may convert (Pepeu, *Dialogues in Clinical Neuroscience,* 6:369-377, 2004). MCI that primarily affects memory is known as "amnestic MCI", which is frequently seen as prodromal stage of Alzheimer's disease. MCI that affects thinking skills other than memory is known as "non-amnestic MCI."

MND is a group of progressive neurological disorders that destroy motor neurons, the cells that control voluntary muscle activities such as speaking, walking, breathing and swallowing. Examples of MNDs include Amyotrophic Lateral Sclerosis (ALS), also known as Lou Gehrig's Disease, progressive bulbar palsy, pseudobulbar palsy, primary lateral sclerosis, progressive muscular atrophy, lower motor neuron disease, and spinal muscular atrophy (SMA) (e.g., SMA1 (also known as Werdnig-Hoffmann Disease), Kugelberg-Welander syndrome, and Kennedy's disease, post-polio syndrome, and hereditary spastic paraplegia.

Ophthalmic Diseases and Disorders

In one preferred embodiment of the invention, the senescence-associated disease or disorder is an ocular disease, disorder, or condition. Examples include, but are not limited to, presbyopia, macular degeneration, cataracts and glaucoma. Macular degeneration is a neurodegenerative disease that causes the loss of photoreceptor cells in the central part of retina, called the macula.

Metabolic Disease

In one preferred embodiment of the invention, the senescence-associated disease or disorder is a metabolic disease selected from diabetes, diabetic ulcer, metabolic syndrome, and obesity.

Senescent cells are understood to play a role in metabolic diseases, such as obesity and type 2 diabetes. Studies have shown that fat tissue from obese mice showed induction of the senescence markers SA-p-Gal, p53, and p21 (Tchkonia et al, *Aging Cell* 9:667-684 (2010); Minamino et al, *Nat. Med.* 15: 1082-087 (2009)). Induction of senescent cells in obesity has potential clinical implications because pro-inflammatory SASP components are also believed to contribute to type 2 diabetes. A similar pattern of up-regulation of senescence markers and SASP components are associated with diabetes, both in mice and in humans. Accordingly, the agents described herein have potential applications in treating or preventing type 2 diabetes, obesity and metabolic syndrome.

Pulmonary Disease or Disorder

In one preferred embodiment of the invention, the senescence-associated disease or disorder is a pulmonary disease. Examples include, but are not limited to, pulmonary fibrosis, chronic obstructive pulmonary disease (COPD), asthma, cystic fibrosis, emphysema, bronchiectasis, and age-related loss of pulmonary function.

COPD is a lung disease defined by persistently poor airflow resulting from the breakdown of lung tissue (emphysema) and the dysfunction of the small airways (obstructive bronchiolitis). Pulmonary fibrosis is a chronic and progressive lung disease characterized by stiffening and scarring of the lung, which may lead to respiratory failure, lung cancer, and heart failure. The agents of the invention can also be used for treating a subject who is aging and has loss (or degeneration) of pulmonary function (i.e., declining or impaired pulmonary function compared with a younger subject) and/or degeneration of pulmonary tissue.

Other Age-Related Disorders

In some embodiments, the senescence-associated disease or disorder being treated is an age-related disorder selected from renal disease, renal failure, frailty, hearing loss, muscle fatigue, skin conditions, skin wound healing, Liver fibrosis, pancreatic fibrosis, oral submucosa fibrosis, and sarcopenia.

Dermatological Diseases or Disorders

In one preferred embodiment of the invention, the senescence-associated disease or disorder is a dermatological disease or disorder, Examples include, but are not limited to, eczema, psoriasis, hyperpigmentation, nevi, rashes, atopic dermatitis (a form of eczema and associated with inflammation), urticaria, diseases and disorders related to photosensitivity or photoaging, rhytides (wrinkles due to aging); pruritis (linked to diabetes and aging); dysesthesia (chemotherapy side effect linked to diabetes and multiple sclerosis); eczematous eruptions (often observed in aging patients and linked to side effects of certain drugs); eosinophilic dermatosis (linked to certain kinds of hemotologic cancers); reactive neutrophilic dermatosis (associated with underlying diseases such as inflammatory bowel syndrome); pemphigus; pemphigoid; immunobullous dermatosis (autoimmune blistering of skin); fibrohistocytic proliferations of skin; cutaneous lymphomas; and cutaneous lupus. Late onset lupus may be linked to decreased (i.e., reduced) function of T-cell and B-cells and cytokines (immunosenescence) associated with aging.

Lifespan and Age Related Diseases or Conditions

In one preferred embodiment, the agent described herein can be used to extend the lifespan of a subject by selectively killing senescent cells over non-senescent cells. In some embodiments, extending the lifespan of the subject comprises delaying onset or progression of an age-related disease or condition. In some embodiments, the age-related disease or condition is selected from atherosclerosis, cardiovascular disease, cancer, arthritis, dementia, cataract, osteoporosis, diabetes, hypertension, age-related fat loss, lipodystrophy, and kidney disease. In some embodiments, the age-related disease or condition is geriatric anxiety disorder. In some embodiments, the age-related disease or condition is age-related inactivity. In some embodiments, the age-related disease or condition is reduction of spontaneous activity. In some embodiments, the age-related disease or condition is reduction of exploratory behavior.

EXAMPLES

Example 1

Materials and Methods

Synthesis of SSK1 and SSK2

Unless otherwise mentioned, all reactions were carried out under a nitrogen atmosphere with dry solvents under anhydrous conditions. Reagents were purchased at the highest commercial quality and used without further purification, unless otherwise stated. Yields were measured chromatographically.

Reactions were monitored by thin-layer chromatography on plates (GF254) supplied by Yantai Chemicals (China) using UV light as the visualizing agent and an ethanolic solution of phosphomolybdic acid and cerium sulfate and heat as the developing agents. Unless otherwise specified, flash column chromatography used silica gel (200-300 mesh) supplied by Tsingtao Haiyang Chemicals (China).

NMR spectra were recorded on a Bruker Advance 600 ($^{13}C$ 150 MHz, $^{19}F$ 565 MHz) and a Bruker Advance 400 ($^{1}H$ 400 MHz) spectrometers, which were calibrated using residual undeuterated solvent ($CD_3OD$ at 3.31 ppm $^1H$ NMR, 49.0 ppm $^{13}C$ NMR). The following abbreviations were used to explain the multiplicities: s=singlet, d=doublet, t=triplet, dd=doublet of doublets, m=multiplet.

Mass spectrometric data were obtained using a Bruker Apex IV FTMS using ESI (electrospray ionization).

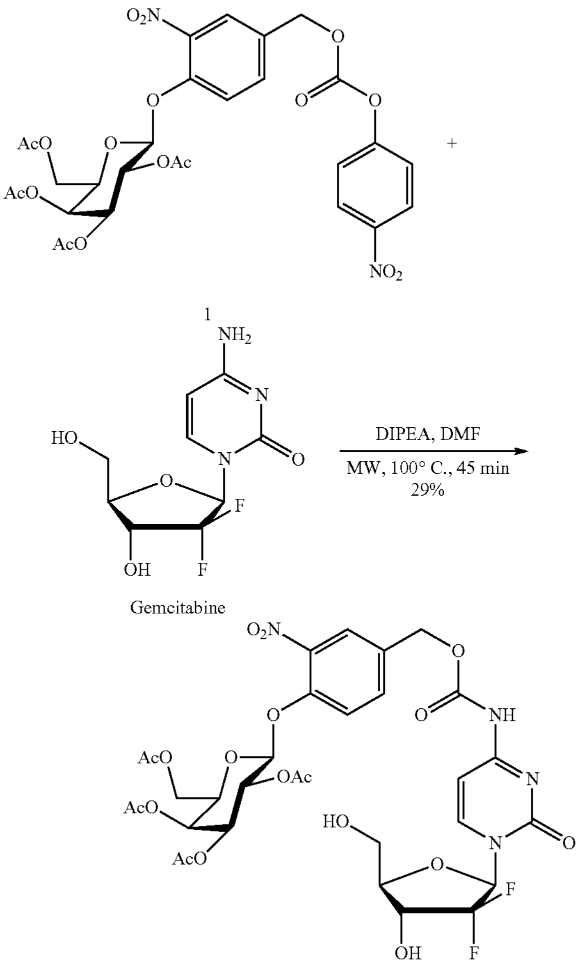

1

Gemcitabine

SSK1

Gemcitabine (2.0 equiv, 0.340 mmol, 89.5 mg) and DIPEA (N,N-diisopropylethylamine) (2.5 equiv, 0.424 mmol, 70 μL) were dissolved in 4 mL of DMF (dimethylformamide). The mixture was stirred for 20 min in a microwave reaction vessel before addition of 1 ((2R,3S,4S,5R,6S)-2-(acetoxymethyl)-6-(2-nitro-4-((((4-nitrophenoxy)carbonyl)oxy)methyl)phenoxy)tetrahydro-2H-pyran-3,4,5-triyl triacetate (1 equiv, 0.170 mmol, 113 mg) (21). The reaction was placed in a CEM Discover microwave reactor (100° C.) and irradiated for 45 min. Then, DMF was removed in vacuo, and the residue was purified by flash column chromatography to give the desired product SSK1 (39.5 mg, 29% yield) as a white solid.

$R_f$=0.3 (dichloromethane:acetone=2:1); $^1H$ NMR (400 MHz, $CD_3OD$): δ 8.31 (d, J=7.6 Hz, 1H), 7.90 (s, 1H), 7.69 (d, J=8.6 Hz, 1H), 7.47 (d, J=8.6 Hz, 1H), 7.31 (d, J=7.6 Hz, 1H), 6.24 (t, J=7.2 Hz, 1H), 5.47 (d, J=3.4 Hz, 1H), 5.39 (d, J=3.3 Hz, 1H), 5.38 (s, 1H), 5.27-5.24 (m, 3H), 4.35 (t, J=6.5 Hz, 1H), 4.32-4.26 (m, 1H), 4.21 (d, J=6.4 Hz, 2H), 3.99-3.94 (m, 2H), 3.81 (dd, J=12.9, 3.2 Hz, 1H), 2.18 (s, 3H), 2.08 (s, 3H), 2.04 (s, 3H), 1.97 (s, 3H); $^{13}C$ NMR (150 MHz, $CD_3OD$) δ 172.01, 171.93, 171.41, 171.26, 165.22, 157.29, 154.18, 150.26, 145.72, 142.22, 134.66, 132.87, 125.72, 123.89 (t, J=258.9 Hz), 119.81, 101.03, 97.02, 86.34 (t, J=32.0 Hz), 82.76 (t, J=3.8 Hz), 72.58, 71.96, 70.14 (t, J=23.0 Hz), 69.50, 68.56, 66.90, 62.60, 60.25, 20.69, 20.65, 20.50, 20.49; $^{19}F$ NMR (565 MHz, $CD_3OD$) δ-119.06 (dd, J=239.7, 9.8 Hz, 1F), −119.91 (d, J=241.7 Hz, 1F); HRMS-ESI (m/z): calc'd for $C_{31}H_{35}F_2N_4O_{18}$ [M+H$^+$] 789.1909, found 789.1907.

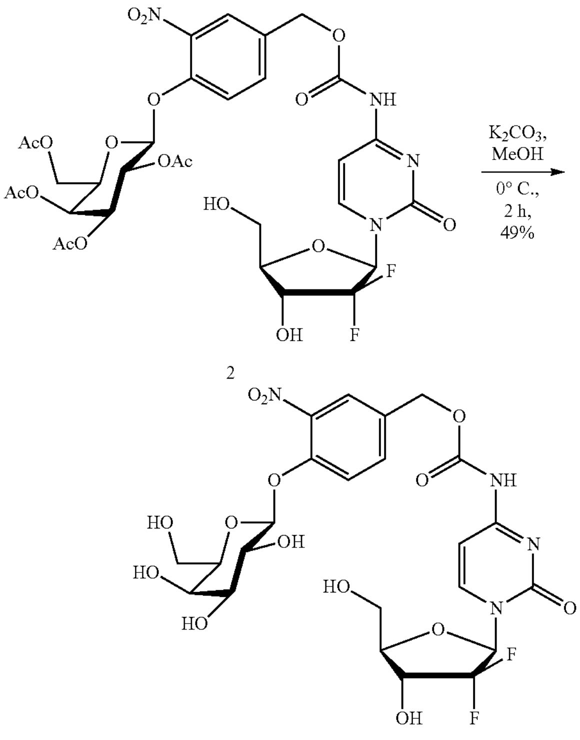

2

3

To a solution of 2 (1.0 eq., 22.8 μmol, 18.0 mg) in MeOH (4 mL) was added $K_2CO_3$ (1.0 eq., 22.8 μmol, 3.2 mg) at 0° C. The resulting solution was stirred at 0° C. After the starting material 2 was completely consumed (about 2 h, monitored by TLC), the solution was neutralized to pH 7 with HCl (1 M), filtered and concentrated. The residue was purified by flash column chromatography to give the desired product 3 (SSK2, 7.0 mg, 49% yield) as a white solid.

$R_f$=0.3 (ethyl acetate:methanol=3:1); $^1H$ NMR (400 MHz, $CD_3OD$): δ 8.31 (d, J=7.7 Hz, 1H), 7.90 (d, J=2.2 Hz, 1H), 7.66 (dd, J=8.8, 2.3 Hz, 1H), 7.47 (d, J=8.8 Hz, 1H), 7.32 (d, J=7.7 Hz, 1H), 6.24 (t, J=7.3 Hz, 1H), 5.22 (s, 2H), 5.05 (d, J=7.7 Hz, 1H), 4.33-4.25 (m, 1H), 3.98-3.93 (m, 2H), 3.89 (d, J=3.4 Hz, 1H), 3.85-3.71 (m, 5H), 3.58 (dd, J=9.7, 3.4 Hz, 1H); HRMS-ESI (m/z): calc'd for $C_{23}H_{27}F_2N_4O_{14}$ [M+H$^+$] 621.1486, found 621.1475.

Cells Culture and Treatments

Mouse Primary Cells Isolation

Mouse embryonic fibroblasts (MEFs) were isolated from E13.5 embryos as described previously (Zhao et al., Cell Stem Cell 23, 31-45 e37(2008)). Newborn mouse skin fibroblasts (NBFs) were isolated from the skin of day 1-3 newborn mice. Adult mouse lung fibroblasts were isolated from 2-month-old and 23-month-old mice. Briefly, mouse embryonic tissues, skin and lung were obtained from described donor mice. Then, these tissues were minced with forceps and incubated in 2 mg/ml collagenase IV (Gibco) for 2-4 hours at 37° C. After enzyme treatment, cells were collected by centrifugation and resuspended in high-glucose DMEM (Gibco) supplemented with 10% fetal bovine serum (FBS) and 1% penicillin-streptomycin (Gibco). The three types of mouse primary cells were all cultured in a humidified incubator at 37° C. and 5% $CO_2$.

Human Primary Cells Isolation

This study was approved by the Institute of Review Board in Peking University (IRB 00001052-15087) and conducted according to the approved protocol. Samples were collected from consenting donors according to ethically approved procedures at China-Japanese Friendship Hospital.

Human embryonic skin fibroblasts (HEFs) were obtained as previously described. Briefly, human embryonic skin tissues, obtained from aborted tissue with informed patient consent, were minced with forceps and incubated in 1 mg/ml collagenase IV for 1-2 hours at 37° C. After enzyme treatment, cells were collected by centrifugation and resuspended in HEF medium (Dulbecco's modified Eagle's medium (DMEM, Gibco) containing 10% fetal bovine serum (FBS, Ausbian), 1% GlutaMAX (Gibco), 1% Non-Essential Amino Acids (NEAA, Gibco) and 1% penicillin/streptomycin (Gibco). Cells were plated on 10 cm tissue culture dishes and grown in 10% FBS DMEM.

Cellular Quiescence and Senescence Induction

To avoid replication-induced senescent cells, low-passage proliferative NBFs (<3 passages), MEFs (<3 passages), mouse lung fibroblasts (<3 passages), HEFs (<10 passages), and HUVECs (<6 passages) were used as normal controls. To induce cell quiescence, MEFs were cultured in DMEM without FBS for 2 days.

For replication-induced senescence, cells were passaged until they lost the ability to proliferate and became senescent. NBFs were used as senescent cells after approximately 8-9 passages or 12 population doublings. HEFs were used after approximately 35 passages or 50 population doublings. HUVECs were senescent after approximately 18 passages or 24 population doublings.

For ionizing radiation-induced senescence, MEFs and HEFs were exposed to 10 Gy of ionizing irradiation in an RS 2000 X-ray Biological Irradiator (Rad Source Technologies, Inc.) at a dose rate of 1.205 Gy/min. The day after irradiation, MEFs or HEFs were passaged at a 1:3 dilution and cultured for another three days. Then these cells were plated to carry out further experiments.

For oncogene-induced senescence by ectopic expression of KRas, cells were transfected with lentivirus containing pLenti-PGK-KRAS or control vector (Addgene, 35633). One day after viral infection, the medium was exchanged, and transfected cells were cultured for another 3 days and passaged at a 1:3 dilution. After another 3 days of culture, the cells became senescent enough for further analysis.

For etoposide-induced senescence, MEFs were treated with 2 μM etoposide for 20 hours, and HEFs were treated with 10 μM etoposide for 12-18 hours. Three days after treatment, cells were sub-cultured at a 1:3 ratio for 72 hours in a fresh medium before further analysis.

For peroxide hydrogen ($H_2O_2$)-induced senescence, cells were incubated in medium with 200 μM $H_2O_2$ for 4 hours or 100 μM for 12 h and culture in fresh medium for several days until they lost the capacity of proliferation.

Plasmid Construction and Lentivirus Production

Plasmids used to interfere the expression of GLB1 with short hairpin RNAs (shRNAs) were obtained from Sigma MISSION shRNA. Genetic knockdown was performed according to the manufacturer's protocol. The shRNA sequences are listed in Table 1.

TABLE 1

Sequence of shRNAs

| shRNA | Sequences (5' to 3') |
|---|---|
| shGLB1-1 | CCGGGAGAAGTCATTCAGATGTTTACTCGAGTAAACATCTGAATGACTTCTCTTTTTTG (SEQ ID NO: 1) |
| shGLB1-2 | CCGGGTGCTAGAATGGAAGCTACATCTCGAGATGTAGCTTCCATTCTAGCACTTTTTTG (SEQ ID NO: 2) |
| shControl | CCGGCAACAAGATGAAGAGCACCAACTCGAGTTGGTGCTCTTCATCTTGTTGTTTTTG (SEQ ID NO: 3) |

Lentivirus production, collection, and infection were as described (Zhao et al., Cell Stem Cell 3, 475-479(2008)).

SSK1 Metabolism Analysis

To detect the release of gemcitabine from SSK1 in senescent and non-senescent cells, the metabolism analysis was performed as previous reported (Karampelas et al., Mol Pharmaceut 14, 674-685(2017)). Briefly, the senescent and non-senescent cells were incubated with 0.5 μM SSK1 in DMEM medium containing 10% FBS and 1% penicillin-streptomycin for the indicated time. Then the cells slightly washed with water for twice and then harvested. Cold methanol used to extract the compounds and samples were prepared after centrifugation. The concentration of gemcitabine was determined by LC-MS/MS analysis.

Flow Cytometry Analysis

Fibroblasts were digested into single cell suspensions by incubation with 0.25% trypsin-EDTA (Invitrogen) at 37° C. for 3-5 min or with accutase at 37° C. for 10 min. Cells were then stained with FITC annexin V and propidium iodide (PI) according to the manufacturer's protocol (FITC Annexin V Apoptosis Detection Kit I, BD Pharmingen™). For chondrocytes Annexin V/7-AAD analysis, the trypsinized live chondrocytes and floating cells were collected, centrifuged and washed with PBS. Cells were stained with the Annexin V Apoptosis Detection Kit (Biolegend, 640934) according to the manufacturer's instruction. Before the flow cytometric analysis, the precision count beads (Biolegend, 424902) were added to count the absolute live cell numbers. Flow cytometry was performed within one hour on an Aria III (BD Biosciences) or FACSVerse (BD Biosciences). Data were analyzed using FlowJo software (FlowJo LLC).

Western Blotting

Senescent NBF cells were plated and incubated overnight at 37° C. The cells were treated with 0.05 μM gemcitabine or 0.5 μM SSK1 prodrug for the indicated time. Before harvest, cells were washed twice with pre-cooled PBS buffer. Total protein was extracted with lysis buffer (50 mM Tris-HCl (pH 7.5), 137 mM sodium chloride, 1 mM EDTA, 1% Nonidet P-40, 10% glycerol, 0.1 mM sodium orthovanadate, 10 mM sodium pyrophosphate, 20 mM β-glycerophosphate, 50 mM sodium fluoride, 1 mM phenylmethylsulfonyl fluoride), and the protein concentrations were normalized using the BCA Protein Assay Kit (Pierce). Protein samples were mixed with protein loading buffer and incubated at 95° C. for 5 min. Western blotting was performed by using the following antibodies: phospho-specific p38 MAPK (Thr180/Tyr182) (Cell Signaling Technology, CST, catalog number 4511) and p38 (CST, catalog number 8690); phospho-histone H2A.X (Ser139) (CST, catalog number 9718) and histone H2A.X (CST, catalog number 7631). The β-tubulin protein level was also determined as the loading control by using the β-tubulin antibody (CST, catalog number 2128). All the antibodies used in western blotting are listed in Table 2.

TABLE 2

Antibodies for western blotting, Immunohistochemical and Immunofluorescence staining

| Gene | Antibody | Catalog Number |
|---|---|---|
| p38 | Rabbit mAb | 4511 (CST) |
| p38 | Rabbit mAb | 8690 (CST) |
| H2A.X | Rabbit mAb | 9718 ( CST ) |
| H2A.X | Rabbit mAb | 7631 ( CST ) |
| β-tubulin | Rabbit mAb | 2128 ( CST ) |
| F4/80 | Rat mAb | 6640 ( Abcam ) |
| p21 | Rabbit mAb | 188224 ( Abcam ) |

Mice

All animal experiments were performed according to the Animal Protection Guidelines of Peking University, China. C57BL/6 (C57) mice were obtained from Beijing Vital River Laboratory Animal Technology Co, Ltd. and maintained under specific pathogen-free facility (SPF) conditions with a 12 light/12 dark cycle and free access to food and water. Old male mice were caged individually, and female mice and young male littermates were maintained with no more than five mice per cage.

Drug Treatments

All drugs were mixed in 90% PBS, 5% Tween-80 (P1754, Sigma), and 5% polyethylene glycol (PEG) (81172, Sigma) and administered to mice by intraperitoneal (i.p.) injection. For treating bleomycin-injured young mice, SSK1 (0.5 mg/kg) or vehicle were given consecutive two days every week for five weeks. For old mice (20-month-old), SSK1 (0.5 mg/kg), gemcitabine (0.5 mg/kg) or vehicle were administrated for continued 3 days every two weeks. Gemcitabine was purchased from MCE.

Bleomycin-Induced Lung Fibrosis and Senescence

Bleomycin was purchased from Selleck. To induce lung senescence and fibrosis, young male and female mice (3-month-old) were subjected to transtracheal injection of bleomycin (1 mg/kg) as previously reported (Bivas-Benita et al., Eur J Pharm Biopharm 61, 214-218(2005))

β-Galactosidase Staining of Cultured Cells and Frozen Sections

Cultured cells were washed once with PBS and fixed in β-galactosidase staining fix solution for 15 min at room temperature. Cells were then washed three times with PBS and incubated with β-galactosidase staining solution (Beyotime Biotechnology) for 16-20 hours at 37° C. For 12-well plates, 1 ml of β-galactosidase staining solution was added to each well. The plate was sealed with Parafilm to prevent evaporation of the staining medium. After the overnight incubation, cells were washed with PBS and observed under a bright field microscope. For β-galactosidase staining of frozen sections, the frozen sections were dried at 37° C. for 20-30 min and then fixed in β-galactosidase staining fix solution for 15 min at room temperature. The frozen sections were washed three times with PBS and incubated with β-galactosidase staining solution overnight at 37° C. After completion of β-galactosidase staining, the sections were stained with eosin for 1-2 min, rinsed under running water for 1 min, differentiated in 1% acid alcohol for 10-20 sec, and washed again under running water for 1 min. Sections were dehydrated in increasing concentrations of alcohols and cleared in xylene. Excess xylene was drained and a coverslip was placed over the section. After drying, the sample was observed under a microscope.

Quantification of SA-β-Gal Tissue Staining

Lung, liver, and kidney frozen sections stained with SA-β-Gal were quantified by ImageJ software (NIH) to measure the SA-β-Gal positive area. The total area was quantified by eosin positive area with ImageJ software (NIH). The relative positive SA-β-Gal positive cells were calculated with the SA-β-Gal positive area divided by the total area. Each mouse was measured with 3-5 regions.

Immunohistochemical Staining

For detecting the p21 expression in lungs, we conducted the immunohistochemical staining experiment for p21 with an immunohistochemical staining kit (SP-9000, ZSGB-BIO). Freshly isolated tissues were fixed by 10% formalin for one day and then transferred in 20% formalin for another day. The tissue blocks were then dehydrated and embedded in paraffin. The embedded tissues were cut and affixed on slides. Before immunohistochemical staining, the slides were deparaffinized, rehydrated, and performed antigen retrieve by high pressure and high temperature in Tris/EDTA pH 8.0 buffer solution. Immunohistochemical staining was conducted according to the manufacturers' instructions. Primary antibody of p21 (Abcam, ab188224) was diluted 1:150 and listed in table 2.

Immunofluorescence Staining

Mouse liver tissues were fixed in 4% paraformaldehyde (DingGuo, AR-0211) for 24 h at room temperature and dehydrated with graded sucrose solution (20% and 30% respectively 24 h) before embedded in OCT compound (Sakura) for cryosection. The embedded tissues were cut and affixed on slides. Before immunohistochemical staining, the sections were fixed in 4% paraformaldehyde (DingGuo, AR-0211) at room temperature for 15 min and blocked with PBS containing 0.25% Triton X-100 (Sigma-Aldrich, T8787) and 2% normal donkey serum (Jackson ImmunoResearch Laboratories, 017-000-121) at room temperature for 1 h. Samples for immunofluorescence staining were incubated with primary antibody: anti-F4/80 antibody (Abcam, ab6640) at 4° C. overnight, washed three times with PBS and then incubated with appropriate secondary antibodies: Alexa Fluor® 488 AffiniPure Donkey Anti-Rat IgG (H+L) (Jackson ImmunoResearch Laboratories, 712-545-150) for 1.5 h at 37° C. Nuclei were stained with Hoechst 33342 (Sigma-Aldrich, B2261).

For quantification of F4/80 positive cells, images were randomly taken at 20× magnification at the same exposure using confocal laser endomicroscopy (LSM 710 NLO &DuoScan System) and then analyzed by ImageJ. Each mouse was measured with at least 6-10 regions.

RT-qPCR

Total RNA was isolated using the Direct-zol RNA MiniPrep Kit (Zymo Research, R2072). RNA was treated with DNase and converted to cDNA using TransScript First-Strand cDNA Synthesis SuperMix (TransGen Biotech, AT311-03). qPCR was performed using Kapa SYBR® FAST qPCR Kit Master Mix (Kapa Biosystems, KM4101) on a CFX Connect™ Real-Time System or CFX96™ Real-Time System (Bio-Rad). Data were analyzed using the $2^{(-\Delta\Delta Ct)}$ method. Gapdh was used as a control to normalize the expression of target genes. The primers for RT-qPCR are listed in Table 3.

TABLE 3

| Gene | Primers used for RT-qPCR |
| --- | --- |
| | Forward Primer (5' to 3') |
| p16 | GCCCAACGCCCCGAACTCTTTC (SEQ ID NO: 4) |
| p21 | CCTGGTGATGTCCGACCTG (SEQ ID NO: 6) |
| p19 | GCCGCACCGGAATCCT (SEQ ID NO: 8) |
| IL1α | AAGTCTCCAGGGCAGAGAGG (SEQ ID NO: 10) |
| IL1β | AAAAGCCTCGTGCTGTCG (SEQ ID NO: 12) |
| IL6 | GTTCTCTGGGAAATCGTGGA (SEQ ID NO: 14) |
| CXCL1 | ACCGAAGTCATAGCCACACTC (SEQ ID NO: 16) |
| TNFα | GCCTCTTCTCATTCCTGCTT (SEQ ID NO: 18) |
| GLB1 | GGATGGACAGCCATTCCGAT (SEQ ID NO: 20) |
| GAPDH | CTTTGTCAAGCTCATTTCCTGG (SEQ ID NO: 22) |
| Fibronectin | CCACCCCCATAAGGCATAGG (SEQ ID NO: 24) |
| Collagen 1 | TGCCGTGACCTCAAGATGTG (SEQ ID NO: 26) |
| Collagen III | GCGGAATTCCTGGACCAAAAGGTGATGCTG (SEQ ID NO: 28) |
| | Reverse Primer (5' to 3') |
| p16 | GCGACGTTCCCAGCGGTACACA (SEQ ID NO: 5) |
| p21 | CCATGAGCGCATCGCAATC (SEQ ID NO: 7) |
| p19 | TTGAGCAGAAGAGCTGCTACGT (SEQ ID NO: 9) |
| IL1α | CTGATTCAGAGAGAGATGGTCAA (SEQ ID NO: 11) |
| IL1β | AGGCCACAGGTATTTTGTCG (SEQ ID NO: 13) |
| IL6 | GGTACTCCAGAAGACCAGAGGA (SEQ ID NO: 15) |
| CXCL1 | CTCCGTTACTTGGGGACACC (SEQ ID NO: 17) |
| TNFα | CTCCTCCACTTGGTGGTTTG (SEQ ID NO: 19) |
| GLB1 | CAGGGCACGTACATCTGGATA (SEQ ID NO: 21) |
| GAPDH | TCTTGCTCAGTGTCCTTGC (SEQ ID NO: 23) |
| Fibronectin | GTAGGGGTCAAAGCACGAGTCATC (SEQ ID NO: 25) |
| Collagen 1 | CACAAGCGTGCTGTAGGTGA (SEQ ID NO: 27) |
| Collagen III | GCGGGATCCGAGGACCACGTTCCCCATTATG (SEQ ID NO: 29) |

Cell Viability Testing

To test the viability of senescent and non-senescent cells treated with SSK1, cells were stained with a mixture of Hoechst 33342 and propidium iodide (PI) (CA1120, Solarbio) to distinguish living and dead cells. After treatment with the small molecules, the cell culture medium was removed, and the cells were washed once with PBS. Then, the cells were stained according to the manufacturer's protocol, where the final concentrations of Hoechst 33342 and PI were 5 μg/ml and 2 μg/ml in PBS buffer. The plate was incubated at 4° C. for 30 min and observed on a fluorescence microscope or automatic cell imaging system. Viable cells were quantified using a MD Image Xpress Micro XL (Molecular Devices).

Cell Counting Kit-8 (CCK-8) analysis was also used to assess cell viability. Senescent and non-senescent cells or chondrocytes were inoculated into 96-well plates and cultured overnight. Then cells were treated with vehicle (0.05% DMSO) or different concentrations of SSK2. After 48 h or 72 h, CCK-8 solution (C0041, Beyotime) was added to each well as 1:10 ratio and inoculated for another 2 h. The absorbance was measured at 450 nm wavelength.

ELISA Analysis

Mouse blood samples were collected, stewed 2 hours at room temperature or overnight at 4° C., and then centrifuged (3000 rpm, 10 min) to gain serum. Secretion of mouse IL1α, IL6, and TNFα was measured using the Mouse Interleukin 1α (IL1α) ELISA Kit (CSB-E04621m, CUSABIO), the Mouse Tumor Necrosis Factor α (TNFα) ELISA Kit (CSB-E04741m, CUSABIO), and the IL-6 (Interleukin-6) Mouse ELISA Kit (ab100712, Abcam) according to the manufacturers' instructions.

Physical Function Measurements

All functional assays were conducted at least 5 days after the last dose of drug was administered.

Rotarod Test

The rotarod test was used to evaluate motor coordination and balance with an accelerating RotaRod system (SANS Bio Instrument, China, SA102). Mice were placed in separate lanes on the rod rotating at an initial speed of 4 rpm/min. The apparatus was set to accelerate from 4 to 44 rpm/min in 300 s. A timer was used to record when each mouse fell or clung to the rod and completed a full passive rotation. Mice were trained at least two times on days 1 and 2 and tested on days 3, 4, and 5. Results were the averaged over 3 trials.

Treadmill Exhaustion Test

Treadmill exhaustion tests were used to evaluate exercise capacity and endurance. A motorized treadmill was used at an incline of 5° with 0.5 mA electrical stimulation (SANS Bio Instrument, China, SA102). Mice were trained for three days, starting at an initial speed at 5 m/min for 2 min and accelerating to 7 m/min for 2 min and then 9 m/min for 1 min. After three training sessions and one day of rest, mice were tested on the fifth day at an initial speed of 5 m/min, which increased by 2 m/min every 2 min until mice were unable to return to the treadmill. The distance (m) traveled before exhaustion was recorded for each mouse.

Whole-Limb Grip Strength Assay

Mice were placed on the top of a grid (Grip strength meter, Columbus Instruments) so they grasped the grid with all four paws. The meter was set to the Peak Tension (T-PK) mode and recorded the grip strength over seven trials. The grip strength (N) was averaged, with the maximum and minimum data points excluded.

Beam Balance

Mice were placed on a 1-m long, 6-mm wide beam resting 60 cm above the floor. A black box full of nesting material from the home cage was placed at the end of the beam apparatus as the end point. At the first day, mice were trained three times on the first day to walk across the beam to the safe box successfully without hesitation or observation. On the test day, the time (s) to cross the center 80 cm mark was measured by two motion detectors: one at 0 cm that starts a timer and one at 80 cm that stops the timer Rearing Behavior Test Mice were taken from the housing room into the testing room and allowed to acclimate to the new environment for a minimum of 30 min before the test. Mice were carefully placed in a 14-cm high and 11-cm diameter transparent cylinder and recorded for 5 min by video camera. The resulting video was analyzed to measure the rearing frequency (when mice stand only on hind legs, raise forelimbs off the ground, and stand upright for over 1 sec).

RNA Sequencing

Total RNA was isolated using Direct-zol RNA MiniPrep Kit (Zymo Research). RNA sequencing libraries were constructed using the NEBNext Ultra RNA Library Prep Kit for Illumina (NEB England BioLabs). Fragmented and randomly primed 2×150 bp paired-end libraries were sequenced using Illumina HiSeq X Ten. RNA sequencing and raw data quality control were performed by Novogene Co., Ltd.

The sequencing data quality were checked by FastQC (version 0.11.8, http://www.bioinformatics.babraham.ac.uk/projects/fastqc/). Sequencing data were aligned to the mm10 genome reference by TopHat2 (version 2.1.1, https://ccb.jhu.edu/software/tophat/index.shtml). Fragments per kilobase per million mapped fragments (FPKM) were computed by Cufflinks (version 2.2.1). For differential gene expression analysis, reads count of each gene were obtained HTSeq (version 0.11.1, https://htseq.readthedocs.io/en/release0.11.1/). The leading log-fold-changes of different conditions which was calculated by R package edgeR (version 0.38.0, https://bioconductor.org/packages/release/bioc/html/edgeR.html) was used as input for gene set enrichment analysis. The gene sets of mouse molecular signature were obtained by msigdbr (version 7.0.1, https://cran.r-project.org/web/packages/msigdbr/index.html). In this package, the original human gene of Molecular Signatures Database (MSigDB v7.0, http://software.broadinstitute.org/gsea/msigdb/index.jsp) were converted to non-human model organism homologous genes. Gene set enrichment analysis was performed by clusterProfiler(version 3.14.0) (https://bioconductor.org/packages/release/bioc/html/clusterProfiler.html). R (version 3.6.0, https://cran.r-project.org/) were used for gene expression analysis.

Gene ontology (GO) term enrichment analyses were performed using DAVID 6.8 functional annotation tool. The gene lists were selected by comparing gene expression between old and young mice or SSK1 treated and vehicle treated old mice with t-test statistics: fold changes >2 and P-values<0.05.

xCell was used to perform cell type enrichment analysis from expression data (Aran et al., Genome Biol 18, 220 (2017)). xCell can decompose tissue expression profile into 64 immune and stroma cell types enrichment score by using gene signatures learned from thousands of pure cell types from various source. Each mouse gene symbols were converted human homologous gene symbols according to the “Human and Mouse Homology Classes with Sequence information” table from MGI database (http://www.informatics.jax.org/downloads/reports/HOM_MouseHumanSequence.rpt). Converted gene symbols with highest expression levels were selected for duplicate gene symbols. log 2(FPKM+1) values were used as expression levels. The homology converted expression matrix was uploaded to xCell online version (https://xcell.ucsf.edu/) to compute cell type enrichment score.

Blood Analysis

For blood routine examination, 50 μl fresh blood was collected from each mouse and mixed with EDTA immediately. The blood samples were analyzed by Celltac Alpha MEK-6400 series hematology analyzers (Nihon Kohden, MEK-6400). For serum biochemical analysis, blood samples were collected, clotted for 2 hours at room temperature or overnight at 4° C., and then centrifuged (1000 g, 10 min) to gain serum. 200 μl serum was aliquot and analyzed of Alanine transaminase (ALT), aspartate transaminase (AST), uric acid (UA) and creatinine (CREA) by Chemistry Analyzer (Mindray, BS-350E).

Statistical Analyses

For statistical analysis, P values were calculated by t-test (when comparing only two groups) or one-way ANOVA (when comparing more than two groups) in Excel or GraphPad Prism 8 with default parameters. All results are expressed as the mean±s.e.m., and n indicates the number of the number of mice. P values are as follows: *P<0.05; P<0.01; *P<0.001; ****P<0.0001.

Results and Discussion

To design a SA-β-gal-responsive prodrug, a panel of FDA-approved drugs were tested to select a compound with potent cytotoxicity for senescent cells. The tests indicated that gemcitabine (shown below) could be a suitable candidate for use in designing a senolytic drug, because 1) it killed both mouse and human senescent cells effectively and potently (FIG. 1A) it exhibited reduced systemic toxicity due to its short plasma circulation time (Mini, et al. *Ann Oncol* 17 Suppl 5, v7-12 (2006), Plunkett et al., *Seminars in Oncology* 22, 3-10 (1995).).

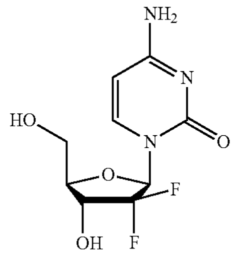

gemcitabine

Additionally, gemcitabine has a 4-amino group which is suitable site for prodrug development (Moysan, et al. *Molecular Pharmaceutics* 10, 430-444 (2013)). Gemcitabine was used to synthesize senescence specific killing compound 1 (SSK1, shown below) by introducing an SA-β-gal-responsive moiety into its backbone (Ghosh, et al. *Tetrahedron Letters* 41, 4871-4874 (2000)), which included acetyl groups, for improved the compound's cellular permeability (Sarkar, et al. *Proceedings of the National Academy of Sciences of the United States of America* 92, 3323-3327 (1995)).

SSK1

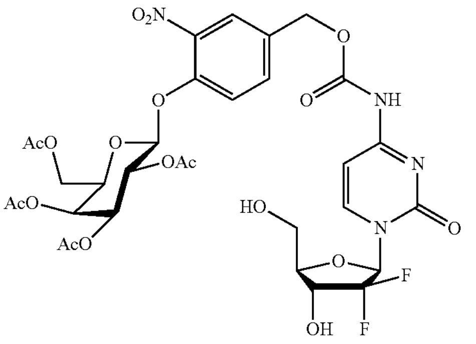

Figure 1A:
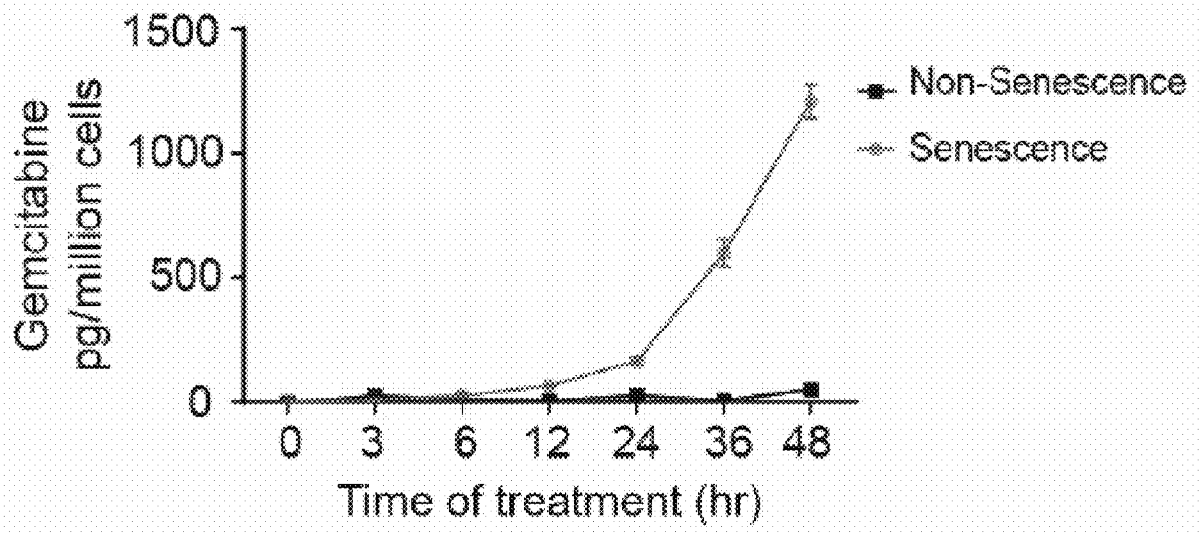
FIG. 1A-B are graphs showing validation of its ability to selectively kill senescent cells.
Figure 1B:
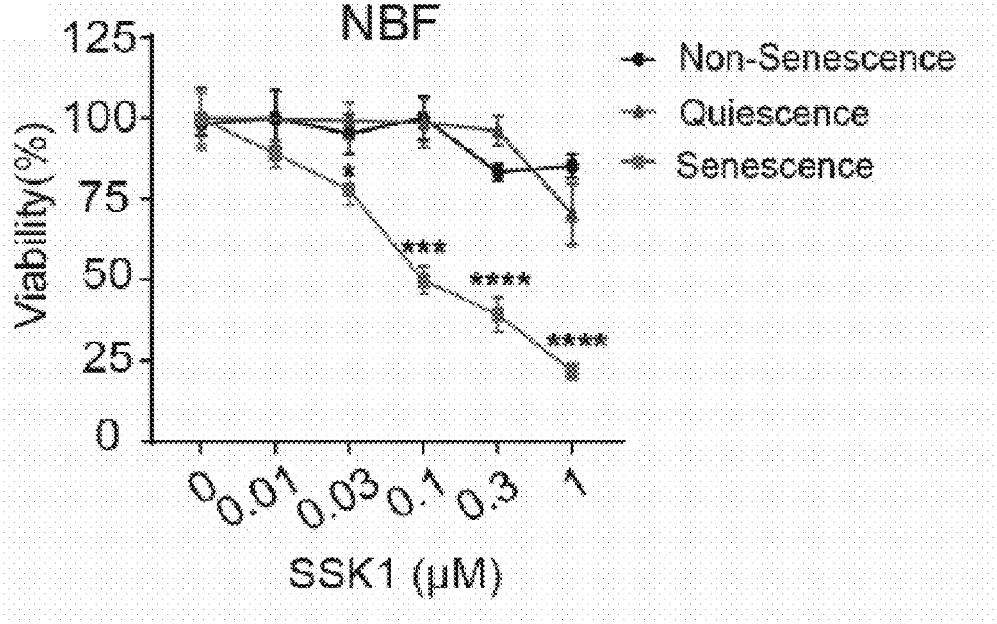

Experiments were conducted to determine the metabolism of SSK1 into gemcitabine in senescent cells when compared to non-senescent cells, by administering SSK1 to replication-induced senescent mouse embryonic fibroblasts and their non-senescent counterparts, and monitoring the release of gemcitabine in the cells as a function of time. SSK1 was specifically cleaved to release cytotoxic gemcitabine in senescent cells but not in non-senescent cells (FIG. 1A). This result suggested that SSK1 could be lethal to senescent cells but safe for non-senescent cells.

Figure 1C:
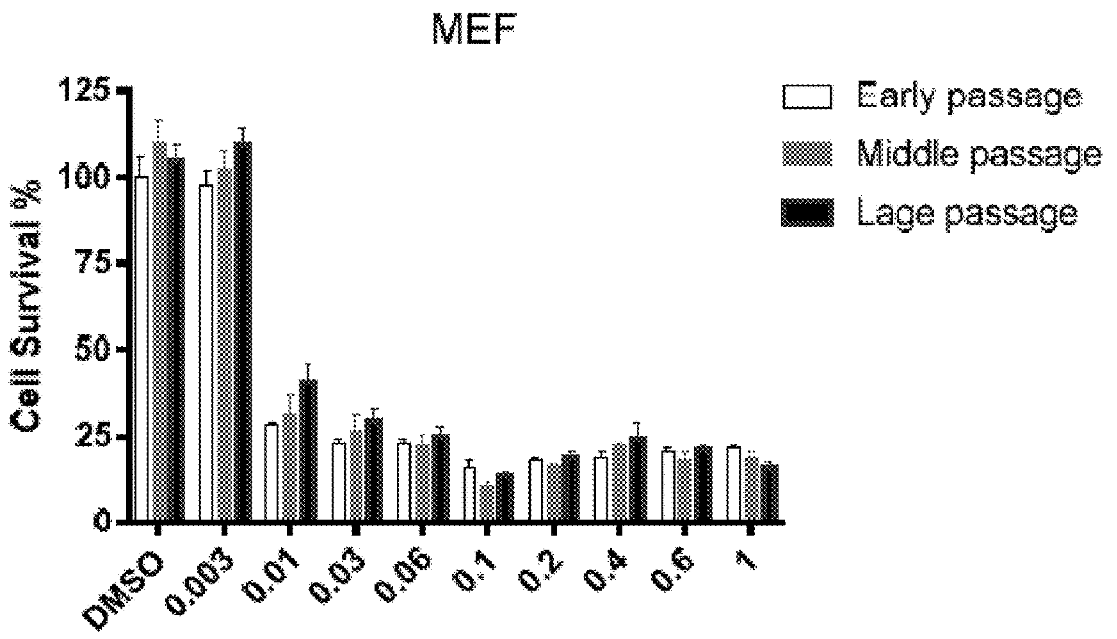
FIGS. 1C and D show the effect of gemcitabine on senescent and non-senescent cells (FIG. 1C) Quantification of viable cells in MEFs of different passages incubated with increasing doses of gemcitabine (n=3).
Figure 1D:
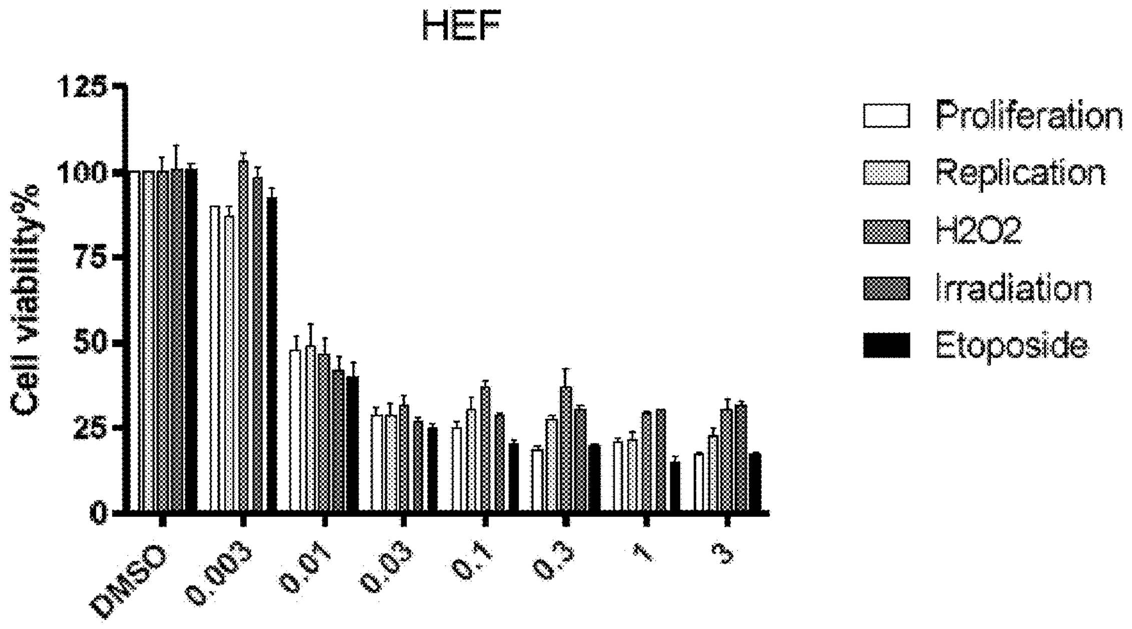
(FIG. 1D) Quantification of viable cells in non-senescent HEFs and senescent HEFs induced by different stressors incubated with increasing doses of gemcitabine (n=3).
Figure 1E:
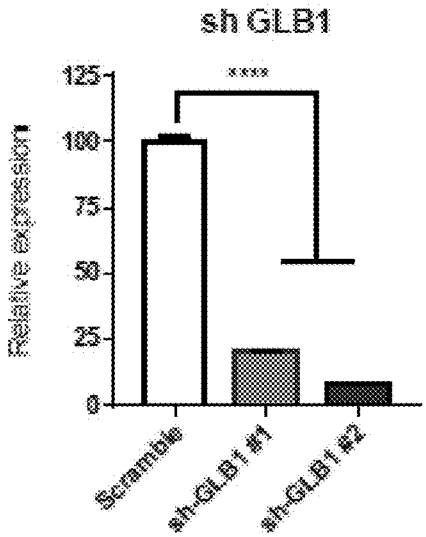
FIG. 1E shows RT-qPCR used to measure expression of GLB1 in the shControl and shGLB1-1 and -2 knockdown treatments (n=3), P<0.0001, unpaired t-tests.
Figure 1F:
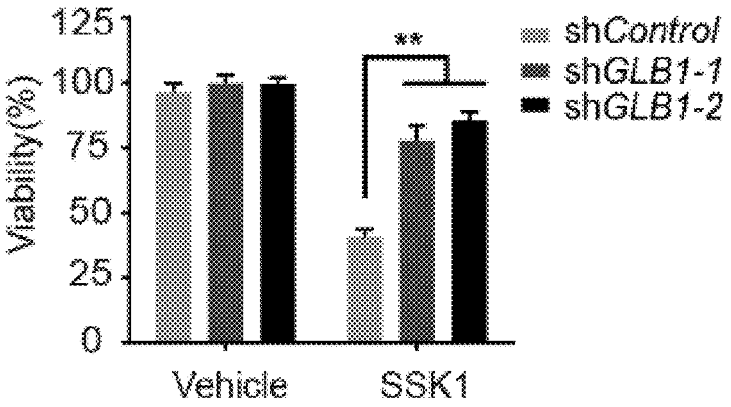
FIG. 1**F shows cell viability of GLB1 knockdown (shGLB1-1 and -2, n=4) or shControl (n=2) senescent cells treated with vehicle or SSK1 (0.5 μM).
Figure 2B:
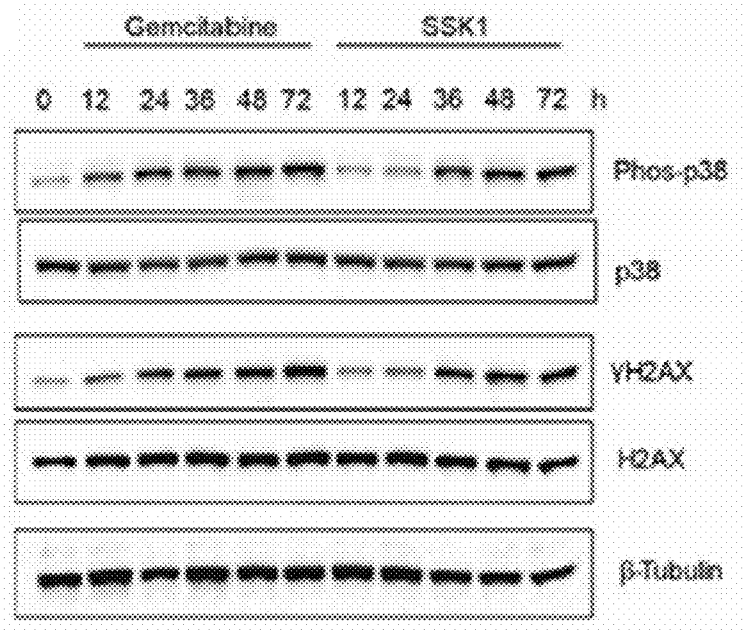
FIGS. 2B and 2C show the effect of SSK1 p38 MAPK activation in senescent cells.
Figure 2A:
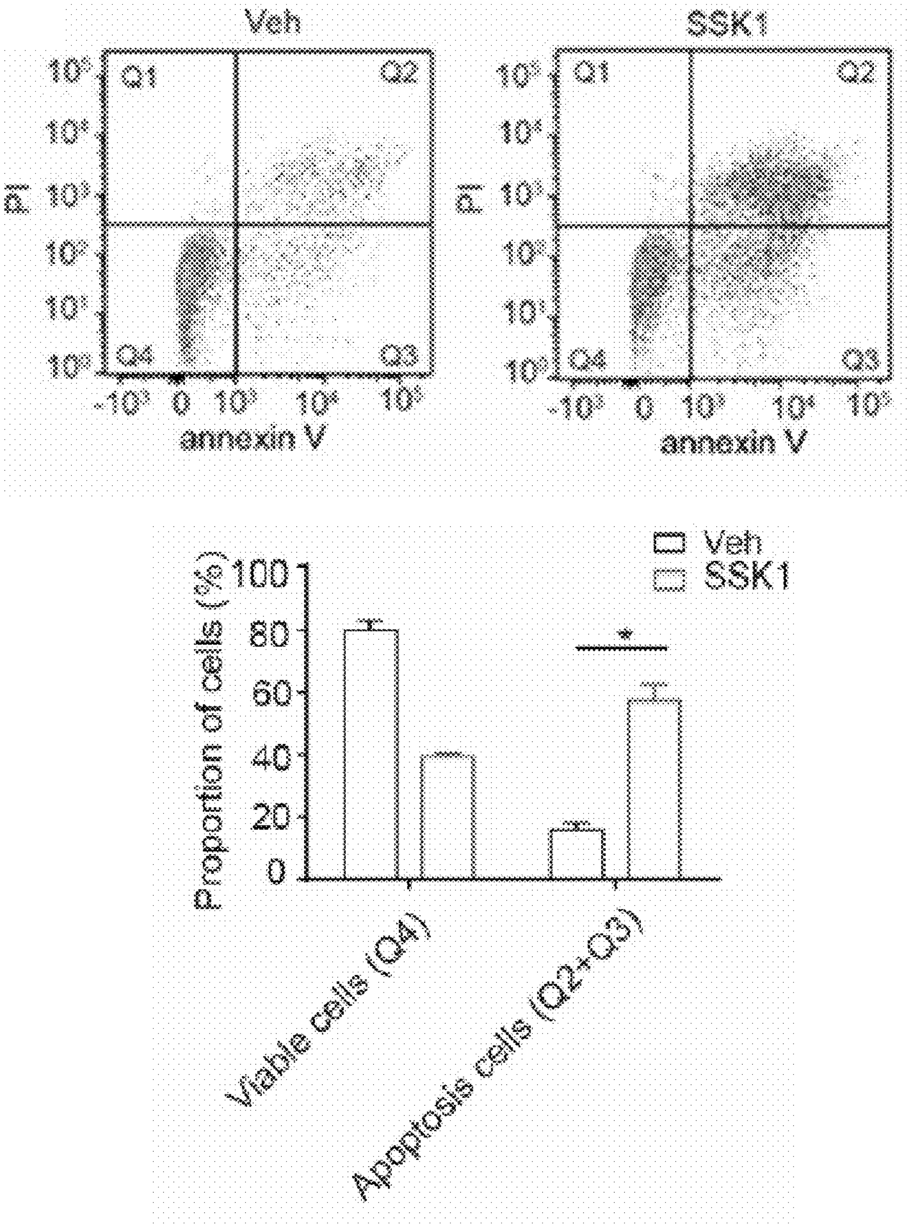
FIG. 2A shows the effect of SSK1 on senescent cells, driven by inducing apoptosis.
Figure 2C:
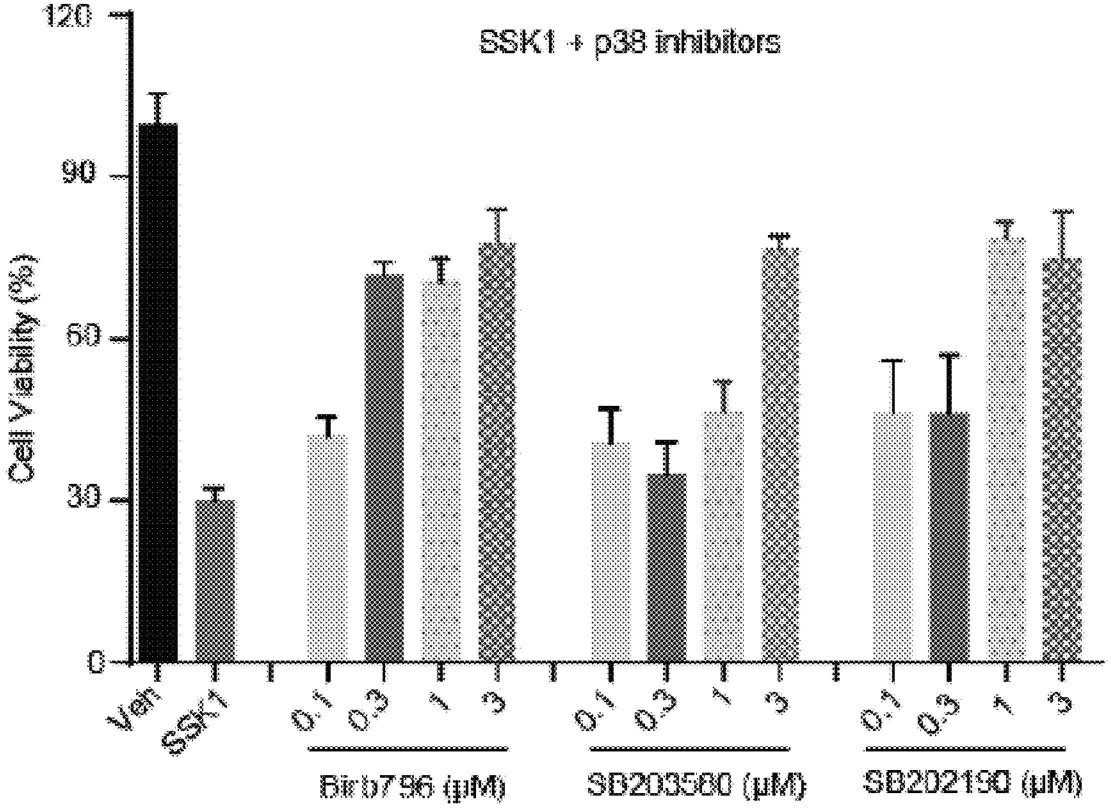

To test SSK1's ability to selectively kill senescent cells, primary mouse fibroblasts and their replication-induced senescent counterparts were treated with SSK1. These studies showed that SSK1 selectively and potently eliminated SA-β-gal-positive senescent cells over non-senescent cells with a wide therapeutic window, while gemcitabine killed both cell types (FIG. 2E, FIGS. 1C and 1D. To address the role of SA-β-gal activity in clearance of senescent cells by SSK1, RNA interference was used to decrease expression of GLB1, the gene encoding SA-β-gal (Lee et al., *Aging Cell* 5, 187-195 (2006)). Knockdown of GLB1 reduced SA-β-gal activity (FIG. 1E), and impaired the ability of SSK1 to kill SA-β-gal-positive senescent cells, suggesting that its specificity for senescent cells depended on SA-β-gal activity (FIG. 1F). As gemcitabine can induce cell death through activation of p38 MAPK (Habiro et al., *Biochem Biophys Res Commun* 316, 71-77 (2004); Koizumi et al., *Anticancer research* 25, 3347-3353 (2005)), the state of p38 MAPK was tested by Western blot in SSK1-treated senescent cells. After 36 hours of treatment, SSK1 activated p38 MAPK by phosphorylation and induced apoptosis in senescent cells (FIGS. 2A and 2B). The p38 MAPK inhibitors SB203580, Birb796, and SB202190 impaired SSK1's ability to specifically kill senescent cells (FIG. 2C). These results suggested that SKK1 was activated by SA-β-gal and selectively killed senescent cells through activation of p38 MAPK and induction of apoptosis.

Figure 2D:
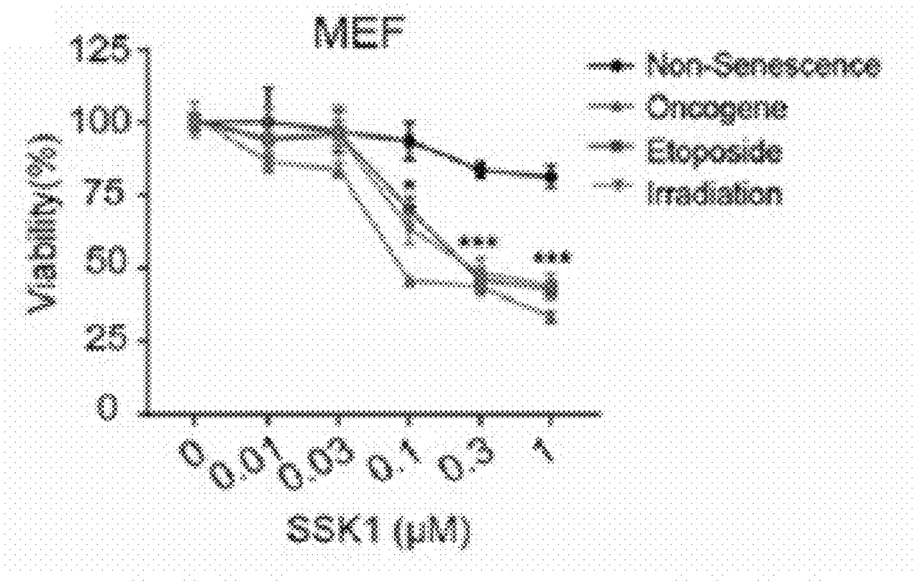
FIG. 2D Quantification of viable non-senescent and oncogene-induced (Kras GV12), small molecule-induced (etoposide, 5 μM), and irradiation-induced (10 Gy) senescent MEFs treated with increasing doses of SSK1 (n=3).
Figure 2E:
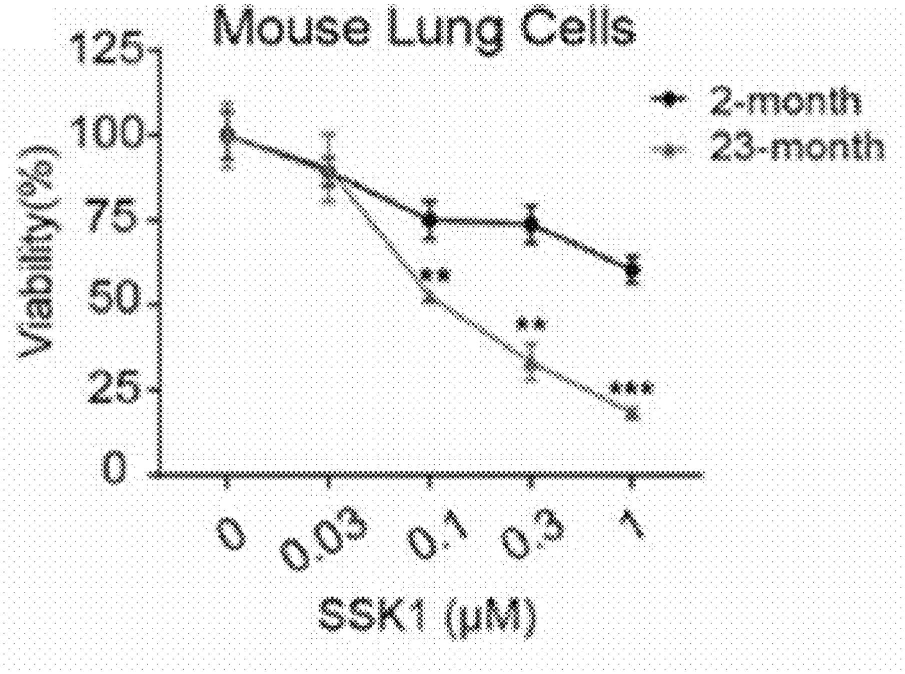
FIG. 2E Quantification of viable non-senescent mouse lung fibroblasts from 2-month-old mice and senescent lung fibroblasts from 23-month-old mice treated with increasing doses of SSK1 (n=4).
Figure 2F:
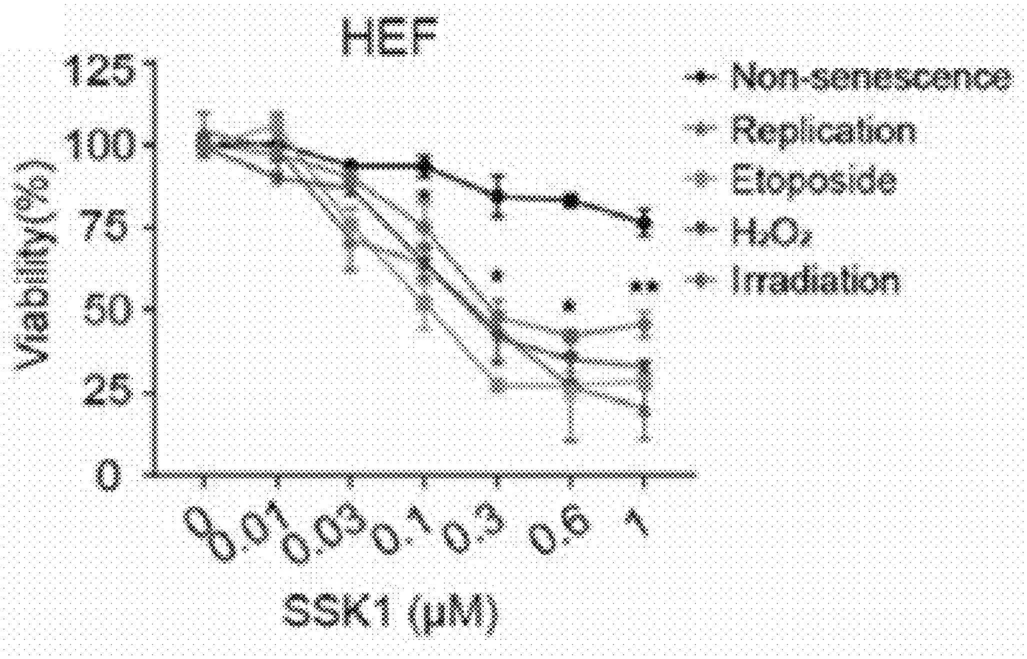
FIG. 2F Quantification of viable non-senescent and senescent human embryonic fibroblasts (HEFs) induced by replication, a small molecule (etoposide, 10 μM), or irradiation (10 Gy) after SSK1 treatment (n=3).
Figure 2G:
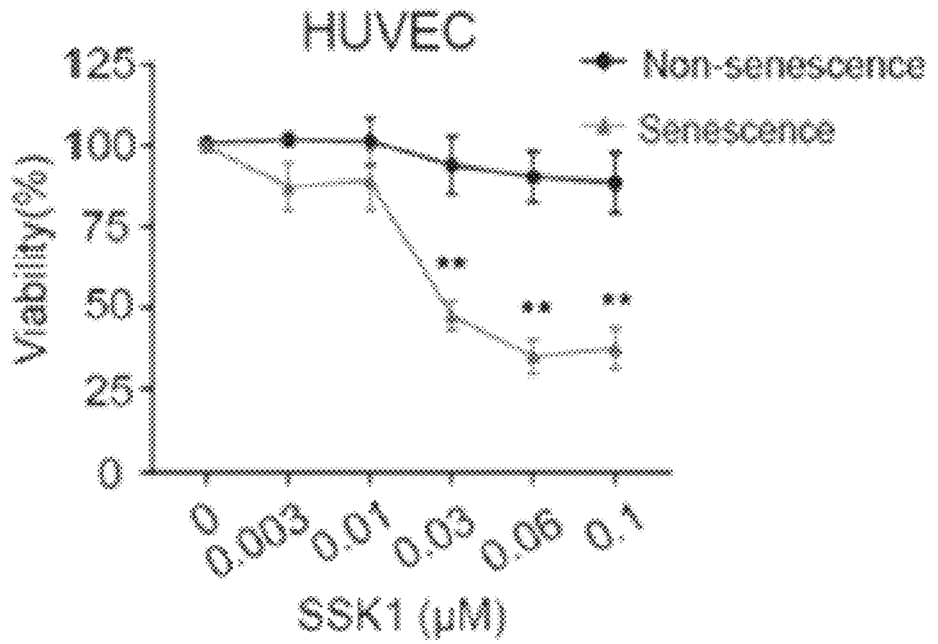
FIG. 2G Quantification of viability in non-senescent and replication-induced senescent human umbilical vein endothelial cells (HUVECs) incubated with increasing doses of SSK1 (n=4). Data are means±s.e.m, unpaired t-test for (FIG. 2E) and (FIG. 2 G), one-way annova test for (FIG. 2D) and (FIG. 2F), *P<0.05, P<0.01, *P<0.001, **P<0.0001.

The specificity of SSK1 for mouse and human senescent cells was further tested. First, senescent mouse fibroblasts induced by ionizing irradiation, oncogene overexpression, or genotoxic stress (etoposide treatment) were treated with SSK1. These senescent cells induced by various stimuli were selectively killed by SSK1, while non-senescent cells were largely unaffected (FIG. 2D). Second, senescent lung cells from 23-month-old mice were treated with SSK1 and the data showed that SSK1 specifically eliminated these senescent cells when compared to non-senescent lung cells from young (3 months) mice (FIG. 2E). Third, to address any difference in SSK1 efficacy between species, human senescent fibroblasts induced by different stimuli were treated with SSK1 (data not shown). These human senescent cells induced by different stresses were cleared by SSK1 when compared with their non-senescent counterparts. Quantitation of the percentage of cell viability in vehicle or SSKI-treated senescent cell populations showed a dose dependent decrease of senescent cells in response to SSKI treatment (FIG. 2F). Last, senescent human umbilical vein endothelial cells (HUVECs) were treated with SSK1 and the data showed that senescent HUVECs were selectively killed by SSK1 compared with non-senescent HUVECs (FIG. 2G and data not shown). Collectively, our results demonstrated that SSK1 selectively killed both murine and human senescent cells in a cell type- and senescent stimulus-independent manner.

Figure 2H:
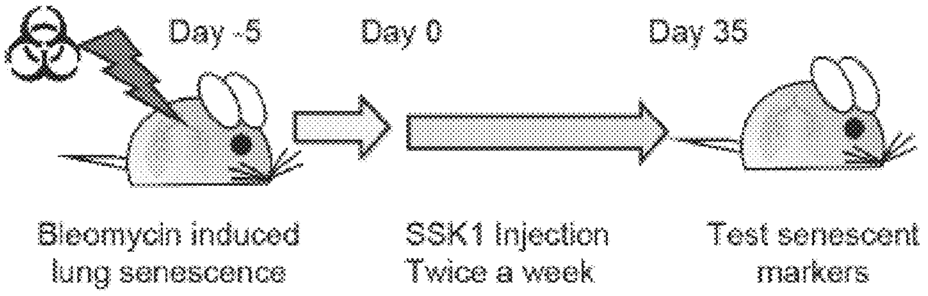
Figure 2I:
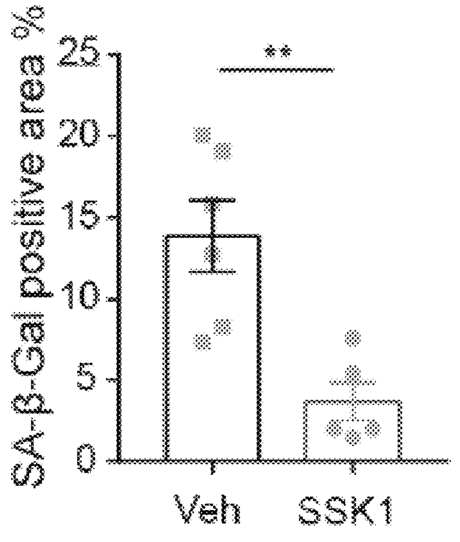

The effect of SSK1 on senescent cells was tested in vivo. Two independent in vivo senescent models were employed: stress-induced premature senescence and naturally occurring senescence in aged mice. For stress-induced senescence, DNA strand breakage and cellular senescence were induced in mouse lungs by intratracheal instillation of bleomycin as a model of idiopathic pulmonary fibrosis (Moeller, et al. *International Journal of Biochemistry & Cell Biology* 40, 362-382 (2008)). SSK1 or vehicle was administrated by intraperitoneal injection for five weeks after five days of bleomycin induction (FIG. 2H). The data showed that SSK1 selectively reduced SA-β-gal-positive cells in senescent lungs and decreased SA-β-gal-positive cells by 3.8-fold when compared with mice with vehicle-treated lung injury (data not shown and FIG. 2I). Immunohistochemistry and RT-qPCR analysis revealed that SSK1 also decreased p21-positive cells and other senescence-associated markers in bleomycin-injured lungs (data not shown and FIG. 2J). SSK1 treatment also attenuated lung fibrosis and decline in physical functions (FIG. 2J to L). Together, these results indicated that SSK1 eliminated SA-β-gal-positive senescent cells and alleviated lung injury symptoms in our bleomycin-induced mouse model.

Figure 3A:
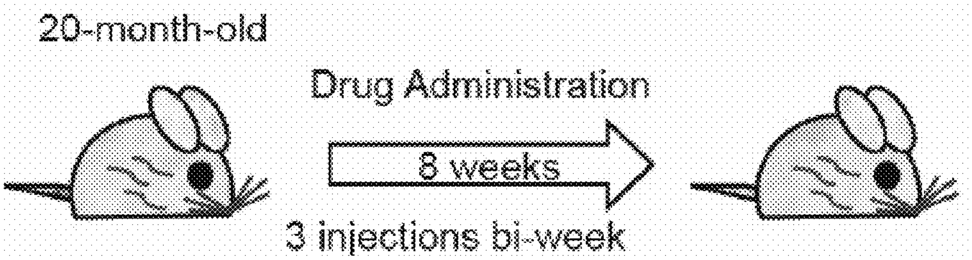
FIGS. 3A-J show studies on the effect of SSK1 on senescent cells and SASP in aged mice.
Figure 3B:
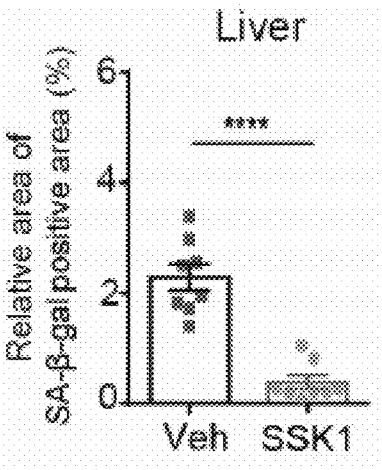
Figure 3C:
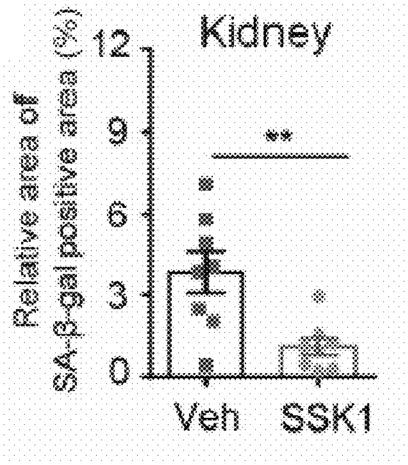
Figure 3D:
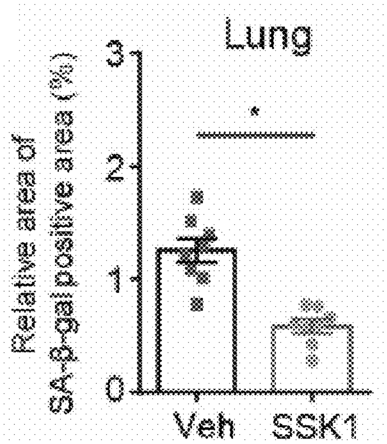
Figure 3E:
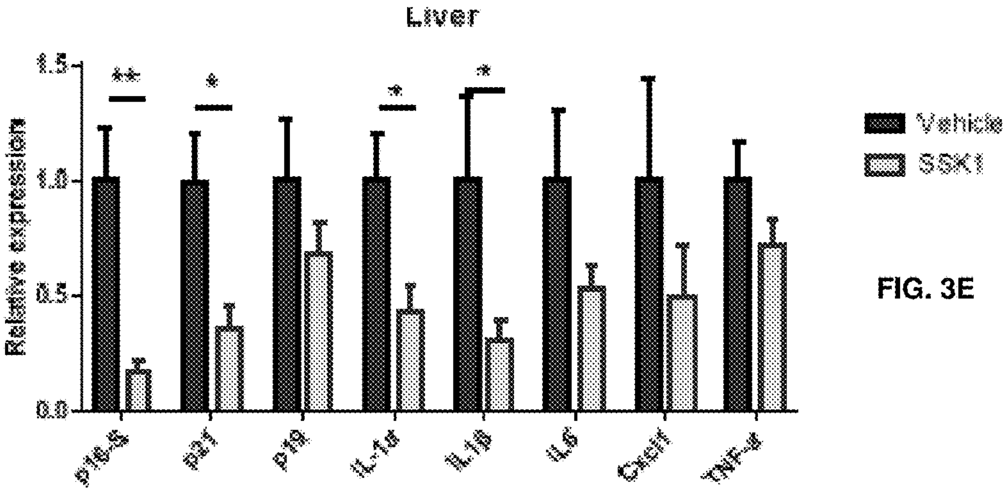
Figure 3F:
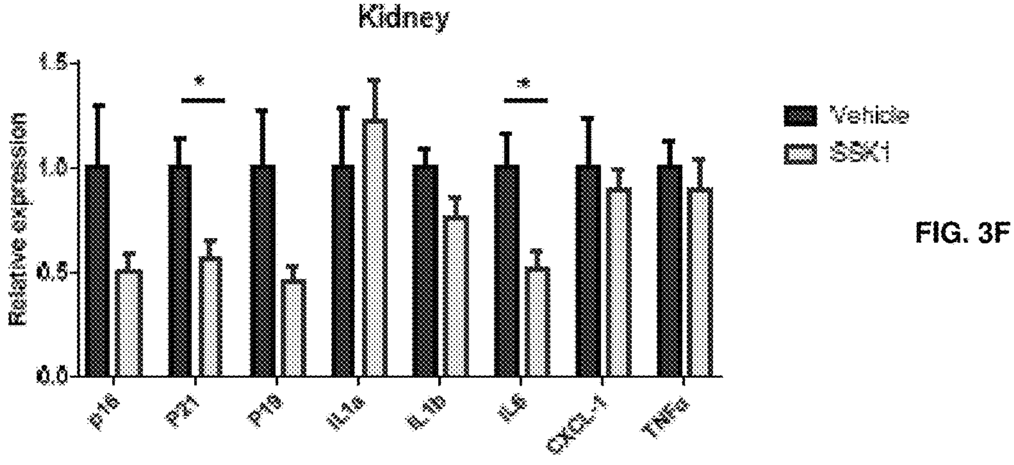
Figure 3G:
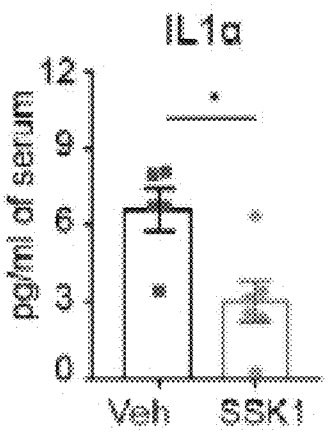
Figure 3H:
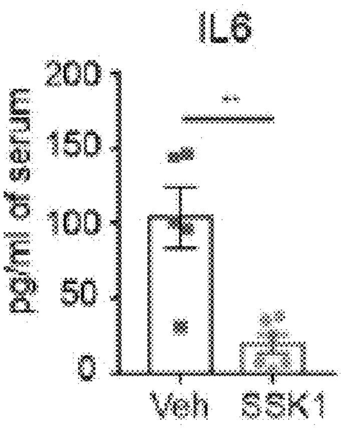
Figure 3I:
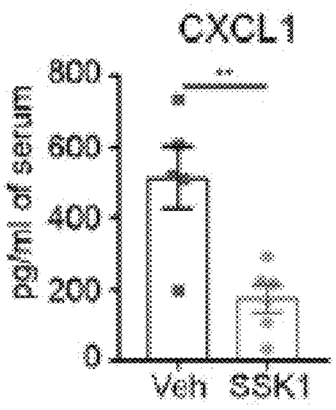
Figure 3J:
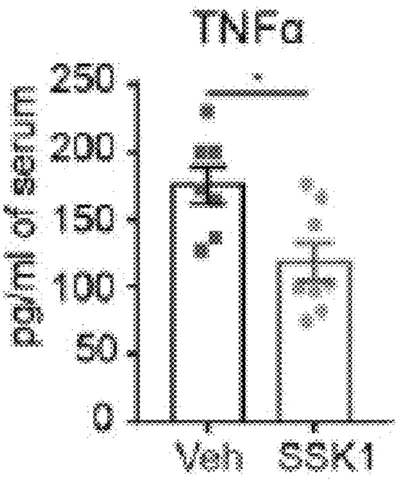

To further examine the effect of SSK1 on naturally occurring senescent cells of aged mice, 20-month-old C57BL/6 mice were with SSK1, vehicle, or gemcitabine intermittently for 8 weeks (FIG. 3A). SSK1 eliminated β-gal-positive senescent cells in aged liver, kidney, and lung tissues by 5.9-, 3.5- and 2-fold, respectively, when compared with vehicle-treated aged mice (FIG. 3B to D, and data not shown). RT-qPCR analysis revealed that SSK1 also decreased expression of other senescent markers, including the CDK inhibitors p16 (in liver) and p21 (in liver and kidney), in aged mice when compared with vehicle treatment (FIGS. 3E and F). Collectively, our new prodrug could reduce both stress-induced and naturally accumulated SA-β-gal-positive senescent cells in mice.

Figure 4F:
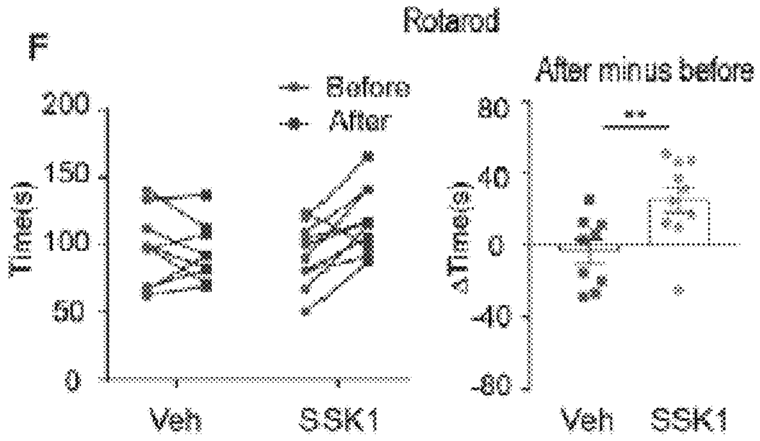
Figure 4G:
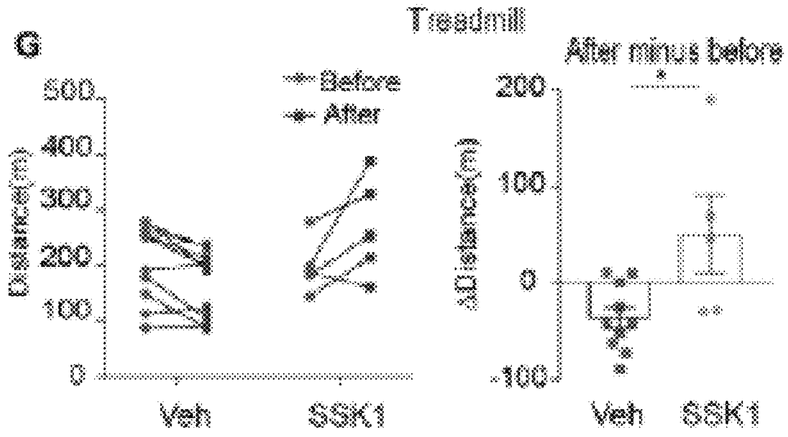
Figure 4H:
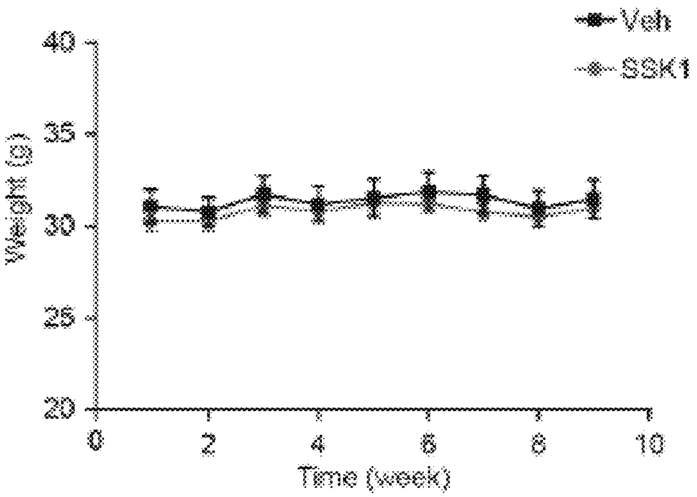
Figure 4I:
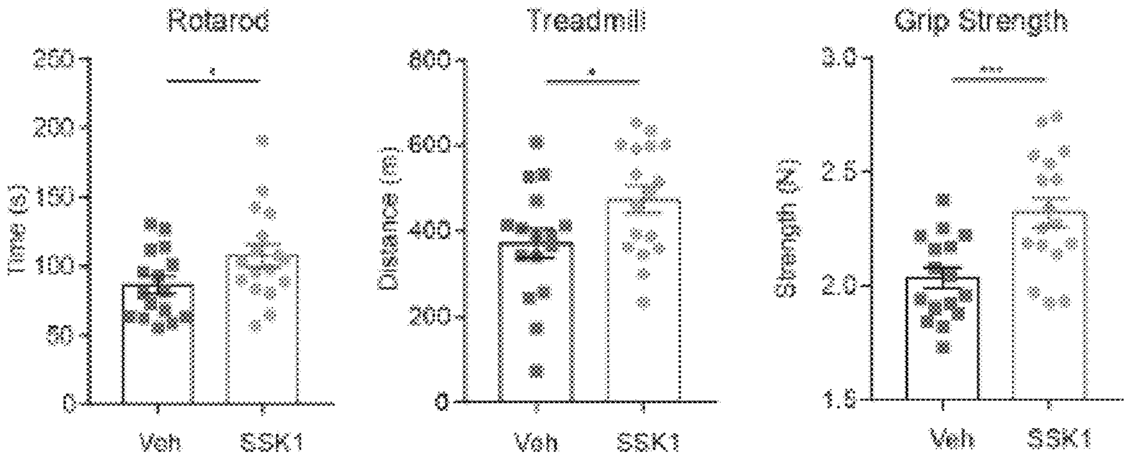

Senescent cells secrete a range of inflammatory cytokines, chemokines, proteinases, and other factors, collectively called SASP (4). SASP contributes to local and systemic low-grade inflammation during aging, age-related degenerative phenotypes, and impairment of physical function (5). We tested whether clearance of senescent cells by SSK1 could attenuate chronic, low-grade inflammation in aged mice. We found that SSK1 decreased several inflammatory factors, including IL1α and IL1β in aged liver and IL6 in aged kidneys (FIGS. 3E and F). Secreted protein levels in serum from aged mice were also measure and decreased secretion of the key SASP factors IL1α, IL6, CXCL1, and TNFα in serum from the SSK1-treated group was observed, when compared to the vehicle-treated group (FIG. 3G to J). These results suggested that our prodrug could eliminate senescent cells efficiently and alleviate SASP both in local niches and systemically in naturally aged mice. To further evaluate the beneficial effect of senescent cell clearance and SASP reduction by SSK1, we examined a series of physical functions of SSK1- or vehicle-treated old mice. Compared with vehicle, SSK1 treatment for 8 weeks significantly increased the maximal rotarod time (FIG. 4A), treadmill distance (FIG. 4B), grip strength (FIG. 4C), and rearing exploration times (FIG. 4D) as well as decreased the balance beam crossing time (FIG. 4E) in old female mice without significant effect on body weight (FIG. 4H). The same results were also observed in old male mice in rotarod, treadmill, and grip strength performance (FIG. 4I). Thus, SKK1 cleared senescent cells, decreased SASP, and improved physical function. Notably, in old mice after SSK1 treatment, rotarod and treadmill performance were improved over the initial state before treatment (FIGS. 4F and G), suggesting that clearance of SA-β-gal-positive senescent cells by SKK1 could potentially rejuvenate some age-related dysfunction.

Figure 4J:
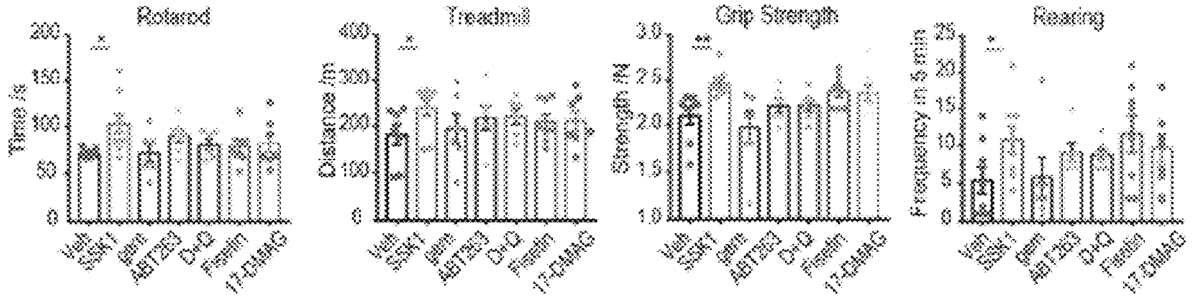

SSKI was next compared with other reported senolytic compounds in cultured senescent cells and aged mice. When compared with proliferative cells, ABT263 selectively killed hydroperoxide-induced senescent human fibroblasts but not replication-induced cells. In addition, irradiation- and etoposide-induced senescent cells were more sensitive to the combination of dasatinib and quercetin, while non-senescent and replication-induced senescent cells remained viable. We then treated aged mice with SSK1 and the known senolytic drugs, fisetin, 17-DMAG, ABT263, and the combination of dasatinib and quercetin, in order to compare their effects on aging-related phenotypes (Zhu et al., *Aging Cell* 14, 644-658 (2015); Chang et al., *Nat Med* 22, 78-83 (2016); Fuhrmann-Stroissnigg et al., *Nat Commun* 8, 422 (2017)). Treatment with SSK1 improved the rotarod, treadmill, and grip strength functions when compared to the other senolytic compounds (FIG. 4J). These results indicated that our prodrug targeting SA-β-gal represents an improved approach for clearance of different senescent cells and prevention of aging.

Figure 5A:
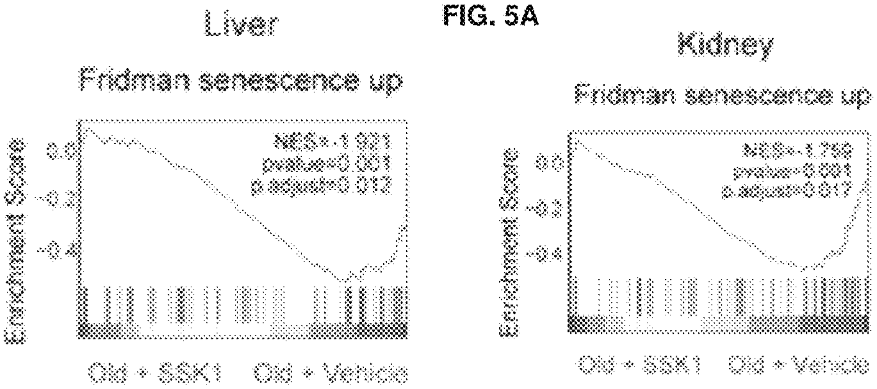
FIG. 5A shows the effect of SSK1 (0.5 mg/kg) treatment on the senescence associated GSEA gene set (Fridman senescence up) in the livers and in the kidneys from old mice compared with vehicle treatment.

Additionally, SSK1 treatment in aged mice could down-regulate the gene signature associated with senescence (FIG. 5A) by gene set enrichment analysis (GSEA) in both livers and kidneys. These results indicated that SSK1 reduced naturally accumulated senescent cells and decreased senescence markers in mice. GSEA analysis also showed that SSK1 down regulated genes associated with inflammatory response, TNFα signaling via NF-κB, IL6, JAK Stat3 signaling and complement trending toward the level of their young counterparts (FIG. 5C to F). Similar results were also shown by gene ontology (GO) enrichment analysis (FIG. 6D to G).

In addition to senescent cells, macrophages are also reported to cause age-associated chronic inflammation. Since the accumulated macrophages are tend to display senescence features such as high level of SA-β-gal and p16 expression, we also studied the effect of SSK1 on the macrophages. We performed immunofluorescence analysis of F4/80 positive macrophages, and found that these cells accumulated in livers with aging and SSK1 could delete macrophages infiltration (FIG. 6A, and data not shown), which could partially account for the decreased inflammatory cytokines in aged mice. The decline of macrophage accumulation was further confirmed by our RNA-seq data of livers analyzed by the xCell approach (FIG. 6B). Notably, these results were consistent with our earlier findings in the lung injury model, in which the reduction of β-gal positive macrophages was observed with the decrease of inflammatory factors in the lungs (FIG. 6C). Collectively, these results showed that SSK1 efficiently alleviated SASP both locally and systemically, which were probably due to elimination of accumulated senescent cells and macrophages in aged organisms.

Figure 5B:
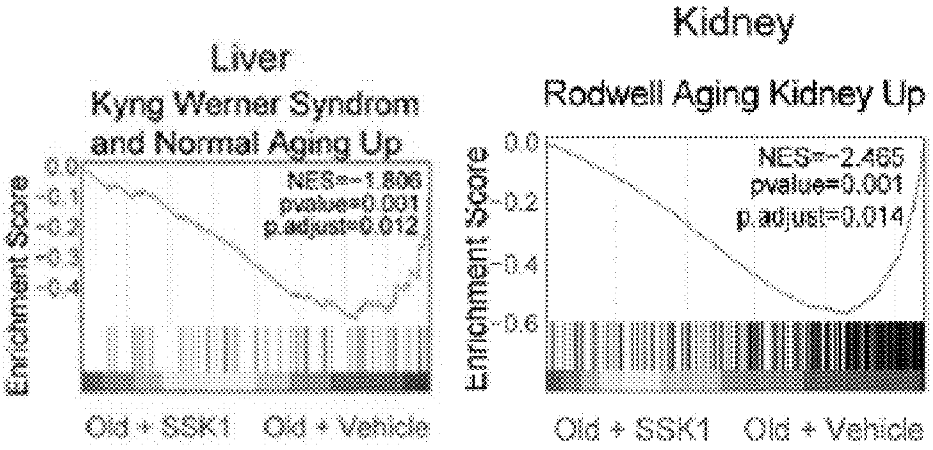
FIG. 5B shows the effect of SSK1 treatment on age-associated signatures in aged livers and kidneys. The data shows GSEA of a statistically significant gene set: Kyng Werner Syndyom and Normal Aging Up of livers downregulated in the old mice treated with SSK1 compared with vehicle; and GSEA of a statistically significant gene set: Rodwell Aging Kidney Up of kidneys downregulated in the old mice treated with SSK1 compared with vehicle.
Figure 5C:
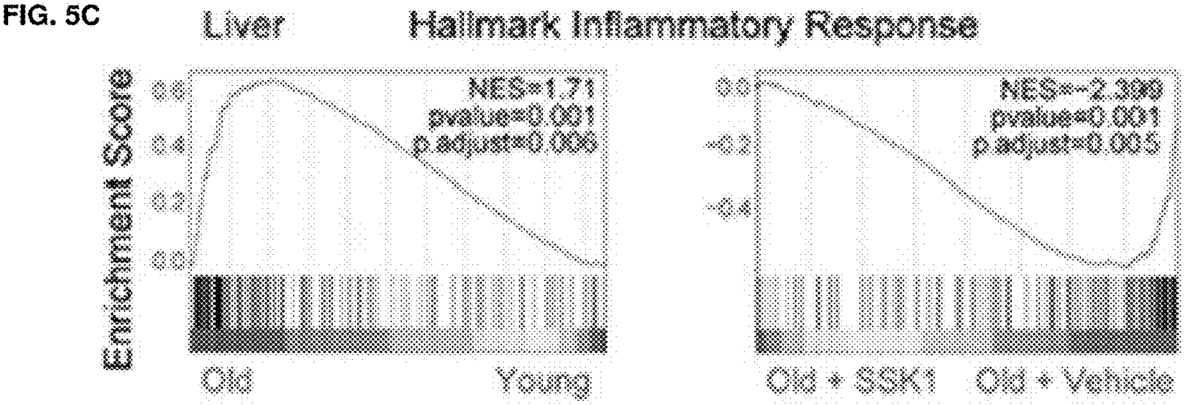
FIGS. 5C and 5D show GSEA of statistically significant gene sets in liver (FIG. 5C) and in kidney (FIG. 5D): Hallmark inflammatory response.
Figure 5D:
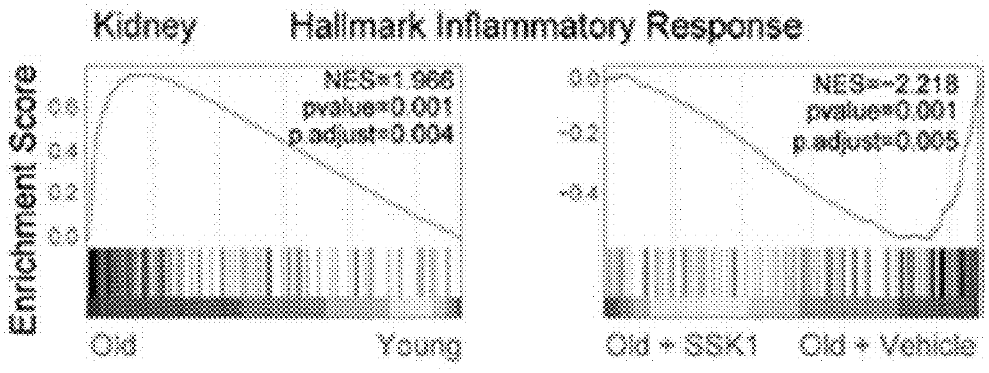
Figure 5E:
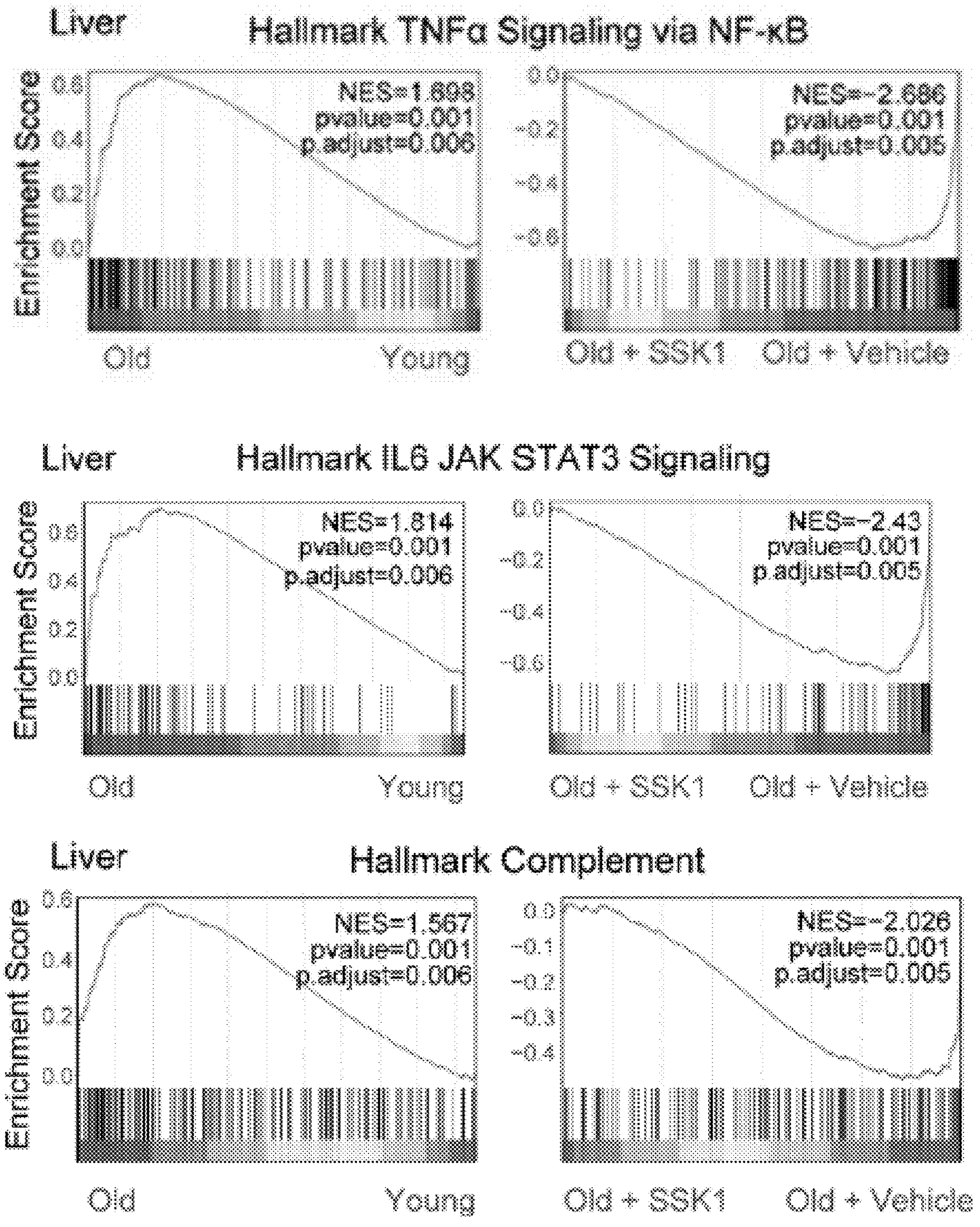
FIG. 5E shows GSEA of a statistically significant gene sets in liver: Hallmark inflammatory TNFα signaling via NF-κB, Hallmark IL6 Jak Stat3 signaling and Hallmark complement enriched in the livers from old mice compared with young mice, and downregulated in the old mice treated with SSK1 compared with vehicle.
Figure 5F:
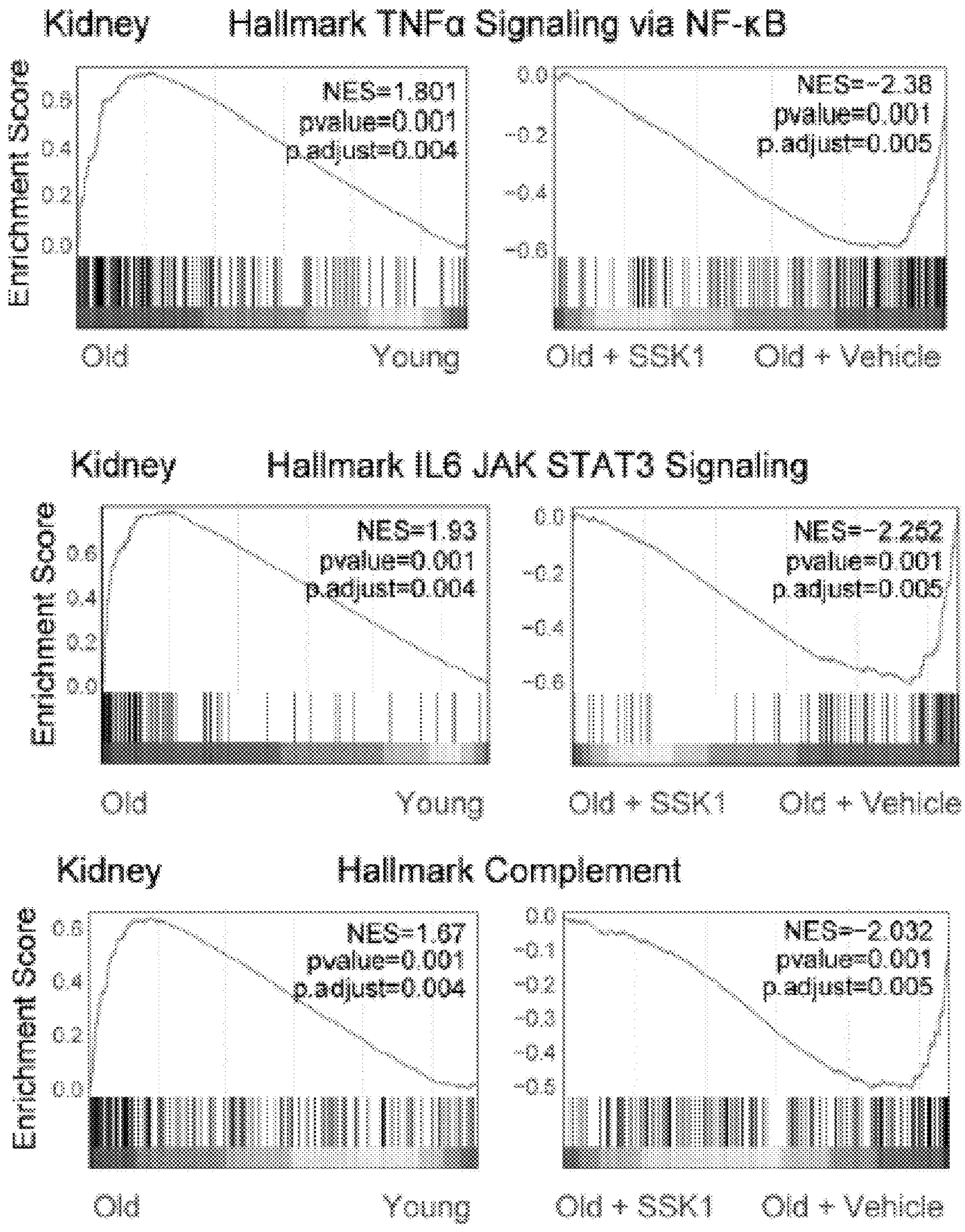
FIG. 5F shows GSEA of statistically significant gene sets in kidney. Hallmark inflammatory TNFα signaling via NF-κB, Hallmark IL6 Jak Stat3 signaling and Hallmark complement enriched in the livers from old mice compared with young mice, and downregulated in the old mice treated with SSK1 compared with vehicle.
Figure 6D:
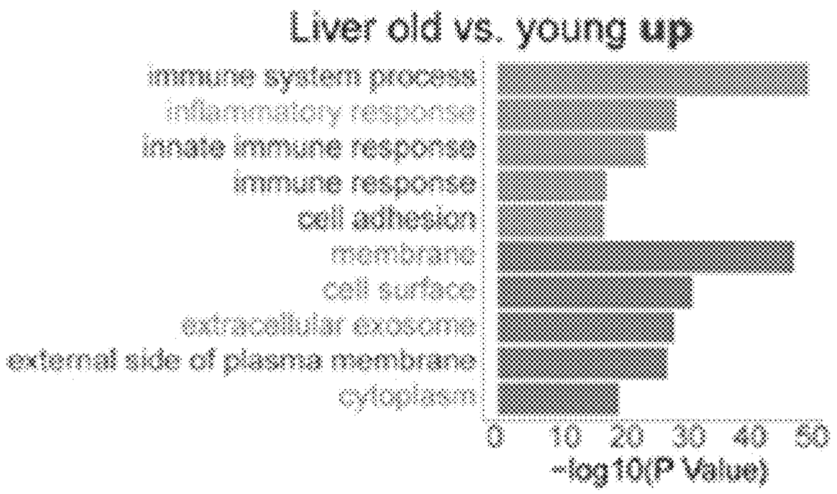
Figure 6E:
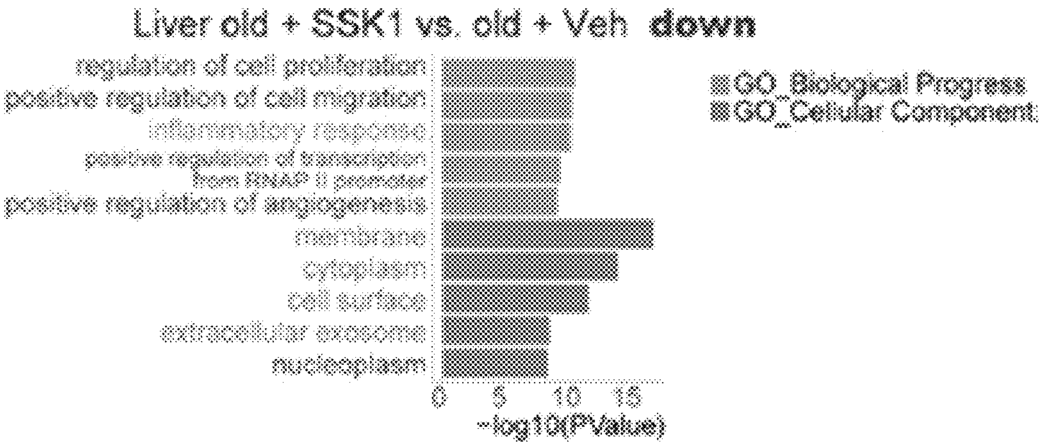
Figure 6F:
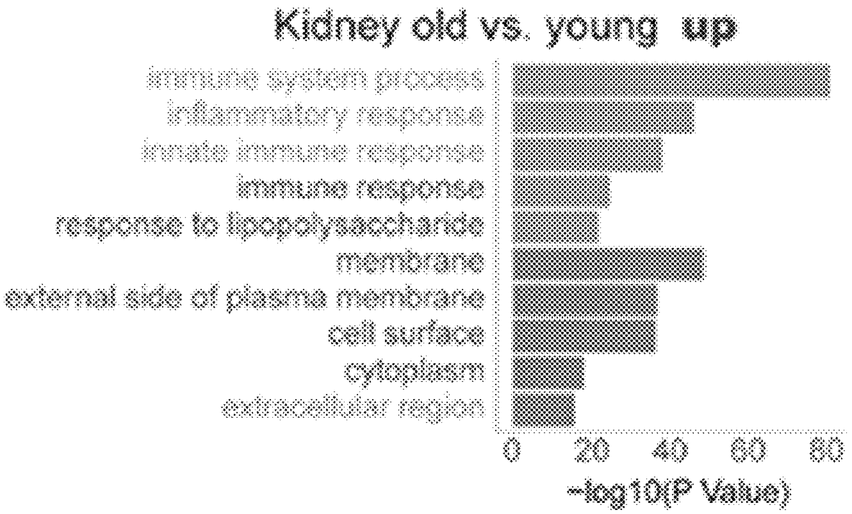

The effect of SSK1 on the age-associated signatures was also tested by the GSEA analysis. The treatment of SSK1 decreased the age-associated signature in aged livers and kidneys (FIG. 5B), suggesting a potential beneficial effect on the clearance of SA-β-gal positive senescent cells in aged tissues. We further performed GO analysis and found that some pathways which were closely related to liver function (oxidation-reduction process, metabolic process, fatty acid beta-oxidation and mitochondrion) were up-regulated in SSK1-treated aged livers (FIG. 6I). On the contrary, these GO pathways were down-regulated in aged livers compared with young livers (FIG. 6H). Additionally, we found that SSK1 could attenuate liver fibrosis as revealed by Masson fibrosis staining (data not shown and FIG. 6J). These findings suggested that the clearance of senescent cells by SSK1 was beneficial to alleviate the aging signature in aged mice.

Figure 7A:
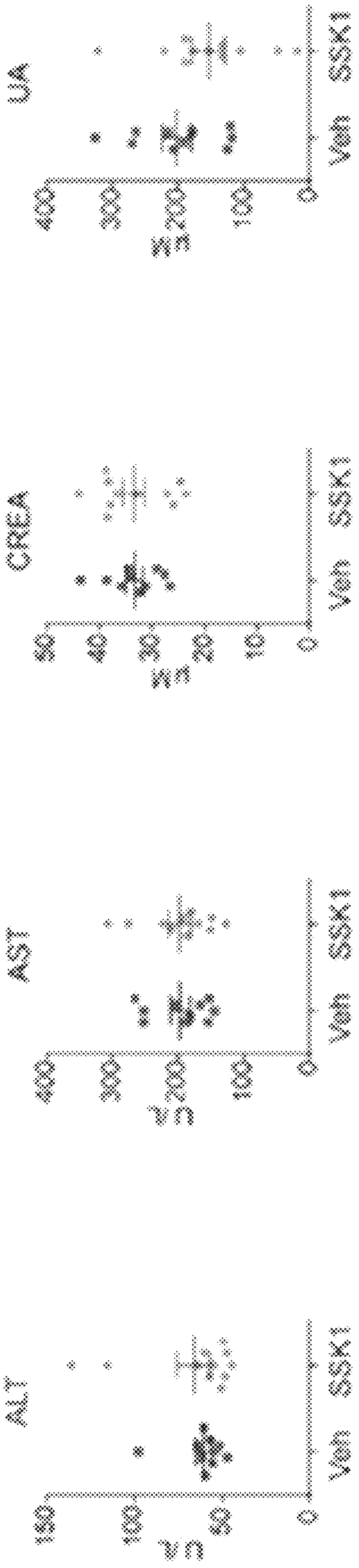
FIG. 7A is a serum biochemical test, which shows the level of Alanine transaminase (ALT), aspartate transaminase (AST), creatinine (CREA) and uric acid (UA) in old mice after vehicle, SSK1 (0.5 mg/kg) or gemcitabine (Gem, 0.5 mg/kg) treatment for 8 weeks.
Figure 7B:
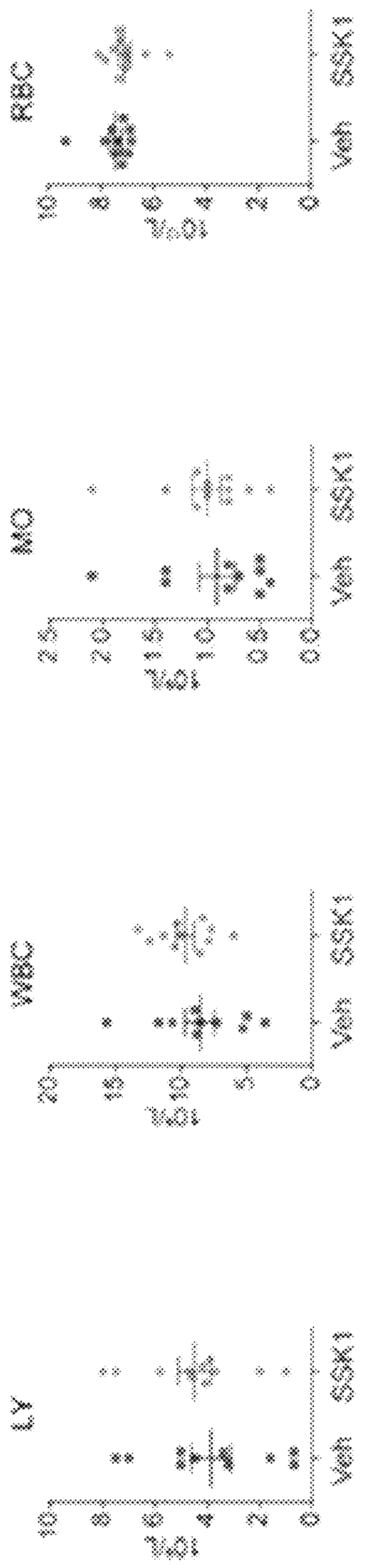
FIG. 7B shows routine analysis of blood, showing the number of granulocytes, white blood cells, monocytes and red blood cells of old mice after vehicle, SSK1 (0.5 mg/kg) or gemcitabine (Gem, 0.5 mg/kg) treatment for 8 weeks. (Vehicle-treated, n=10; SSK1-treated, n=9; gemcitabine-treated, n=11).
Figure 7C:
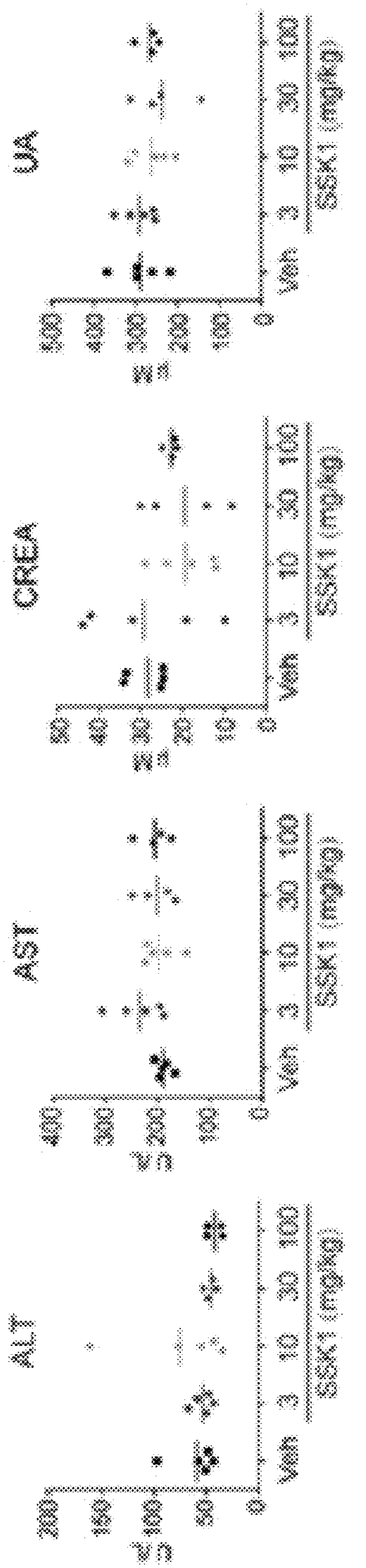
FIG. 7C shows serum biochemical test of mice treated with increasing dosed of SSK1. The level of Alanine transaminase (ALT), aspartate transaminase (AST), creatinine (CREA) and uric acid (UA) in old mice after vehicle and SSK1 (3, 10, 30, 60, 100 mg/kg) treatment for 5 weeks with 3 injections a week. (n=5, 5, 5, 4, 4, 4 for each group respectively).
Figure 7D:
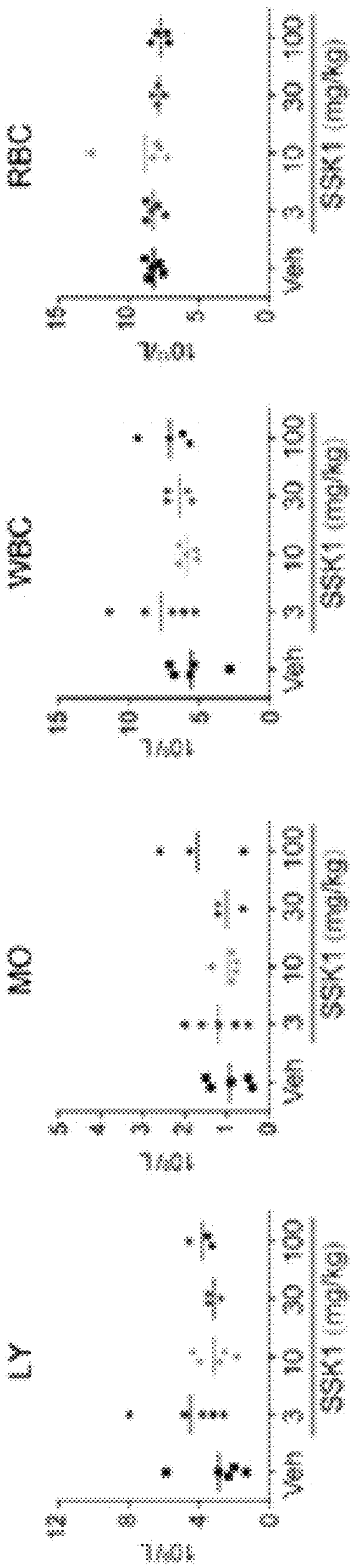
FIG. 7D shows routine analysis of blood of mice treated with increasing dosed of SSK1. The number of granulocytes, white blood cells, monocytes, and red blood cells of old mice after vehicle and SSK1 (3, 10, 30, 60, 100 mg/kg) treatment for 5 weeks with 3 injections a week. n=5, 5, 5, 4, 4, 4 for each group respectively. All data are means±s.e.m. Each data point represents an individual mouse, statistical significance was calculated using unpaired two-tailed t-test.

Additionally, the treatment of SSK showed no obvious system toxicity from the results of the serum biochemical test and routine blood analysis (FIGS. 7A and B). To study the toxicological effects of SSK1 in vivo, aged mice were treated with SSK1 at a high concentration (100 mg/kg) and high frequency. Serum biochemical test and routine blood analysis showed no obvious systemic toxicities in these mice (FIGS. 7C and D).

These studies demonstrated the prodrug design approach as demonstrated here to target SA-β-gal can improve selective elimination senescent cells in a species-, cell type- and senescence stimulus-independent manner. SSK1 cleared stress-induced and naturally occurring senescent cells, decreased SASP, and improved global physical function in aged mice. These findings indicate that prodrug design can improve the use SA-β-gal as a target for prodrug design and clearance of senescent cells both in vitro and in vivo. Effective clearance of SA-β-gal-positive senescent cells by SSK1 provides a prospective approach to delay aging. The demonstrated prodrug design strategy provides a foundation to generate new compounds that directly target senescence for anti-aging therapy.

An understanding of the toxicological effects of SSK1 in vivo is critical to clinical applications. Importantly, the data in this application shows that high concentration (100 mg/kg) and high frequency SSK1 treatment had no apparent systemic toxicities. This provides strong evidence for the in vivo safety of SSK1. This safety profile is further supported by comparison to Gemcitabine, an SSK1 effector and approved clinical drug. First, the effective in vivo dosage of SSK1 was approximately 60-fold lower than the clinical dosage of Gemcitabine (30 mg/kg) and indicating a greatly reduced risk of in vivo toxicity for SSK1. Second, Gemcitabine is a nucleoside analogue that potently affects rapidly dividing cells and the off-target effects of Gemcitabine could be shown in different proliferating cell types(Bocci et al., Eur J Pharmacol 498, 9-18(2004); Rettig et al., Int J Cancer 129, 832-838(2011)). SSK1, however, targets only β-gal positive cells. Notably, in addition to macrophages, the data above shows that the majority of non-senescent β-gal positive cells are rapidly dividing epithelial cells. As a result, the potential types of proliferating cells with SSK1 sensitivity are greatly narrowed relative to Gemcitabine. Even though small numbers of β-gal positive epithelial cells are targeted by SSK1 treatment, these cells have robust self-renewal ability (Humphreys et al., Cell Stem Cell 2, 284-291(2008)). Consistent with this self-renewal property, the present studies showed that epithelial tubular cells in the kidney with elevated β-gal activity had a high percentage of Ki67+ cells. Following SSK1 treatment, only a few cells of this tubular cell population was shown to be undergoing apoptosis, and this little impairment could be easily repaired by the rapid self-renew of tubular cells during SSK1 treatment. Moreover, the short duration of SSK1 treatment might avoid significant impairment in related tissues and further minimize its side effects. In summary, the data in this study demonstrates the superiority and safety of SSK1 strategy by targeting β-gal to selectively remove senescent cells of multiple cell types. These findings open a new avenue for the treatment of aging-associated diseases and a clinical opportunity for intervention into the aging process.

Example 2

Effective Treatment of SARS-CoV-2-Infected Rhesus Macaques by Attenuating Inflammation Severe acute respiratory syndrome coronavirus 2 (SARS-CoV-2) has caused a pandemic of coronavirus disease 2019 (COVID-19). The transformations from mild to severe life-threatening situations during SARS-CoV-2 infection can be fast (Huang et al., 2020; Wang et al., 2020). Approximately 15% of patients progressed to severe pneumonia, resulting in respiratory failure and high hospital mortality, especially in elderly patients (Grasselli et al., 2020; Yang et al., 2020). Accordingly, this situation has led to an urgent demand for effective therapeutic strategies for COVID-19. Most recently, the anti-viral drug remdesivir approved by the FDA has been reported to shorten the recovery time of COVID-19 in patients with mild symptoms. However, it showed limitations in treating severe or critical patients (Grein et al., 2020; Wang et al., 2020). In this regard, there is still a pressing demand to develop effective approaches to treat COVID-19 in severe or critical patients.

Hyperinflammation has emerged as a critical driver of COVID-19's disease severity based on clinical immunopathology. In the clinic, acute immune responses induced by SARS-CoV-2 infection, including intensive immune cell infiltration and elevated proinflammatory cytokine release, are associated with acute lung injury (ALI) and acute respiratory distress syndrome (ARDS) (Tay et al., 2020; Moore and June, 2020). Moreover, the critical roles of hyperinflammation in coronavirus-induced syndromes have been supported by studies of MERS or SARS (de Wit et al., 2016; Channappanavar and Perlman, 2017). Thus, there is a global imperative in developing drugs that can effectively treat hyperinflammation of COVID-19. Although several anti-inflammatory drugs have been used to treat COVID-19 patients, these drugs have significant limitations (Ritchie and Singanayagam, 2020). Drugs such as corticosteroids with extensive immunosuppression effects may delay the elimination of viruses and often have serious side effects (AUYEUNG et al., 2005; Russell et al., 2020). On the other hand, drugs targeting specific cytokine pathways, such as the anti-IL-6R monoclonal antibody, only show limited therapeutic benefits in a small population of patients (Luo et al., 2020), indicating that the "cytokine storm" may not be based solely on elevated IL-6 level (Zhang et al., 2020). In addition, anti-inflammatory treatment interfering with JAK/STAT3 pathways may dysregulate type 1 interferon-mediated antiviral innate immunity (Boor et al., 2017). Thus, new clinical treatments of COVID-19 are needed that can target the inflammatory characteristics of severe patients without interrupting antiviral activity.

Most recent studies of SARS-CoV-2 have identified macrophages to be pivotal for excessive inflammation in COVID-19. The infiltration of macrophages has been considered important for the production of large amounts of proinflammatory cytokines, including IL-1β, IL-6 and TNF-α (Giamarellos-Bourboulis et al., 2020; Merad and Martin, 2020). Necropsies also identified an intense infiltration of macrophages in the lung tissues of fetal COVID-19 patients, and similar observations were found in SARS-CoV-2-infected nonhuman primate models (Xie et al., 2020; Bao et al., 2020). Furthermore, single-cell RNA sequencing (scRNA-seq) showed a high proportion of macrophages over lymphocytes presenting in bronchoalveolar lavage fluid (BALF) of severe COVID-19 patients (Liao et al., 2020). Consistent with studies of SARS-CoV-2, infiltration and accumulation of macrophages in the lung were also found in other coronavirus diseases and influenza infections (Qi et al., 2019; Page et al., 2012). Depletion of macrophages protected mice from lethal SARS-CoV infection, highlighting the important roles of macrophages in coronavirus-induced symptoms (Channappanavar et al., 2016). Therefore, targeting macrophages to regulate hyperinflammation in SARS-CoV-2 infection could be an effective strategy to treat COVID-19 patients.

Recently, we developed the β-galactosidase-activated prodrug SSK1 that has the ability to effectively target macrophages. Furthermore, SSK1 treatment efficiently repaired lung injuries in an ALI animal model with a decreased level of proinflammatory cytokines, showing an anti-inflammatory effect (Cai et al., 2020). In this study, we investigated the therapeutic effects of SSK1 in treating SARS-CoV-2 infection using nonhuman primates, which efficiently recapitulated key pathological changes of COVID-19.

Here, we demonstrate that SSK1, a small molecule that reduces β-galactosidase-positive macrophages, effectively ameliorated pneumonia caused by SARS-CoV-2 infection in nonhuman primates. Importantly, SSK1 efficiently mitigated clinical symptoms and pathologically reduced pneumonia progression at both early and late stages of SARS-CoV-2 infection. Moreover, we found an anti-inflammatory effect with a reduction in macrophage infiltration in the lungs of SSK1-treated animals, which was accompanied by decreased levels of cytokines in the peripheral blood and lungs. Our results demonstrate the therapeutic benefit of SSK1 treatment in nonhuman primates to SARS-CoV-2 infection, leading to the development of effective treatments for COVID-19.

Ethics and Biosafety Statement

All animal experiments were performed in the animal biosafety level 4 (ABSL-4) facility of National Kunming High-level Biosafety Primate Research Center, Yunnan, China. Rhesus macaques were monitored at least twice daily throughout the experiment. Commercial monkey chow, treats and fruit were provided daily by trained personnel. All animal procedures were approved by the Institutional Animal Care and Use Committee of Institute of Medical Biology, Chinese Academy of Medical Science (Ethics number: DWSP202002 001).

Study Design

To evaluate the therapeutic effect of SSK1 on the recovery period of SARS-CoV-2 infection, we used nine rhesus macaques of three different ages as reported before (Lu et al., 2020). All the animals were inoculated with total 4.75 ml of $10^6$ pfu/ml SARS-CoV-2 intratracheally (4.00 ml), intranasally (0.50 ml) and on conjunctiva (0.25 ml). The nine rhesus macaques were divided into three groups according to the treatments, which included vehicle (DMSO), low dosage (0.5 mg/kg) and high dosage (2.0 mg/kg) of SSK1, respectively. Each group randomly selected one young, one adult and one old monkey. The final grouping is presented as following: the vehicle-treated group, RM1 (young), RM2 (adult) and RM3 (old); 0.5 mg/kg SSK1-treated group, RM4 (young), RM5 (adult) and RM6 (old); 2.0 mg/kg SSK1-treated group, RM7 (young), RM8 (adult) and RM9 (old). As the experimental schedule showed in FIG. 8A, we started the treatment on 22 dpi. For each group, vehicle (DMSO), low dosage SSK1 (0.5 mg/kg) and high dosage SSK1 (2.0 mg/kg) were administrated intravenously (i.v.) once a day from 22 to 28 dpi. Animals were anesthetized and clinical exams were performed daily. We recorded the body weight, anal temperature on each examination day and collected blood samples for hematology analysis as well as swabs form nasal, throat and rectal for virus quantitative detection. The monkeys were euthanized on 34, 35 and 36 dpi. We collected the bronchoalveolar lavage fluid (BALF) with 10 ml PBS (Gibco, Cat #21-040-CVC) and recorded the pathological changes of all organs. Tissue samples collected from all organs and the BALF were further analyzed.

To assess the efficacy of SSK1 in the early stage of SARS-CoV-2 infection, four adult rhesus macaques were randomly assigned to two groups, 2.0 mg/kg SSK1-treated group (M1 and M2) and vehicle-treated group (M3 and M4). These four monkeys were infected by inoculating with total 5.75 ml of $10^6$ pfu/ml SARS-CoV-2 intratracheally (4.00 ml), intranasally (0.50 ml), oral (1.00 ml) and on conjunctiva (0.25 ml). The monkeys were treated immediately with 2.0 mg/kg SSK1 (SSK1-M1, SSK1-M2) or vehicle solution (Vehicle-M3, Vehicle-M4) after SARS-CoV-2 inoculation once daily for 7 consecutive days. Clinical examinations were performed daily and we recorded body weight and anal temperature. Blood samples for hematological analysis and swabs drawn from the nose, throat and rectum were collected for quantitative virus detection. Chest X-ray was performed as indicated time point. Animals were euthanized and necropsied at the indicated time points after treatment. We collected the bronchoalveolar lavage fluid (BALF) with 10 ml PBS (Gibco, Cat #21-040-CVC) and recorded the pathological changes of all organs. Tissue samples collected from all organs and the BALF were further analyzed.

Drug Treatment 100 mg/ml SSK1 dissolved in DMSO (Life Science, Cat #1087C114) was mixed in 95% PBS (Gibco, Cat #21-040-CVC), 5% Tween-80 (BioFroxx, Cat #1716) and administrated intravenously (i.v.) at the dosage of 0.5 mg/kg or 2.0 mg/kg to monkeys at the indicated time point (the injection finished within 5-10 minutes). DMSO mixed in 95% PBS (Gibco, Cat #21-040-CVC), 5% Tween-80 (BioFroxx, Cat #1716) was intravenously (i.v.) injected as vehicle.

Virus Amplification and Identification

Viral stock of SARS-CoV-2 was obtained from the Center of Diseases Control, Guangdong Province China. Viruses were amplified on Vero-E6 cells and concentrated by ultrafilter system via 300 kDa module (Millipore). Amplified SARS-CoV-2 were confirmed via RT-PCR, sequencing and transmission electronic microscopy, and titrated via plaque assay ($10^6$ pfu/ml).

Cell Culture

Vero-E6 cells were well cultured in high-glucose DMEM (Gibco, Cat #11995500BT) supplemented with 10% fetal bovine serum (FBS, Gibco, Cat #10099-141C) and 1% penicillin-streptomycin (Solarbio, Cat #P1400) in a humidified incubator at 37° C. and 5% $CO_2$. Trypsin-EDTA (0.05%) phenol red (Gibco, Cat #25200) was used for cell dissociation.

Chest Radiograph

Before image taken, the monkey was anaesthetized with 10 mg/kg ketamine hydrochloride (Beikang, Cat #100761663). Then mobile digital medical X-ray photography system (MobileCooper, Browiner China) was used to take the chest X-ray image of the monkey as the indicated time point. To analyze the X-ray data, radiographs were evaluated by two experienced doctors blinded to the group assignment of the monkeys.

Hematology

The blood samples were collected from saphenous vein of hind limb of anaesthetized monkeys using 5 ml blood collection tube containing sodium citrate anti-coagulant for further analysis. For Complete Blood Count (CBC), Auto Hematology Analyzer (BC-5000 Vet, Mindray, China) was used. The white blood cells-related numbers and percentages of Neutrophil (Neu), Lymphocyte (Lym), Monocyte (Mon), Eosinophil (Eos), Basophil (Bas), and platelet-related items, platelet count (PLT), mean platelet volume (MPV), platelet distribution width (PDW), plateletcrit (PCT) were analyzed. For serum biochemical analysis, the blood was clotted for 30 min at 4° C. and centrifugated at 3,000×rpm for 15 min to obtain serum. The serum was used to analysis the alanine transaminase (ALT), aspartate transaminase (AST), alkaline phosphatase (ALP), uric acid (UA) and creatinine (CRE-E) by Chemistry Analyzer (Mindray, BS-350E).

Tissues Collection and Homogenate Supernatant Preparation

Half lung from each monkey was used for BALF collection and the other half was used for homogenate and histopathology examination. Besides, the following tissues were collected: trachea, bronchus, lung, submandibular gland, intestinal lymph node, hilar lymph node, spleen, stomach, duodenum, colon, rectum, liver, pancreas, kidney, heart, muscle, testis, bladder, penis, spinal cord, brain and cerebrospinal fluid. One gram of tissue was homogenized in 3 ml PBS. The homogenates were centrifuged at 3,000 rpm for 10 min and the supernatant was collected and used for analysis.

Broncheoalveolar Lavage Fluid (BALF) Collection

After dissection, 10 ml PBS (Gibco, Cat #21-040-CVC) containing 2% FBS (Gibco, Cat #10099-141C) was used to carefully wash the half lung of the monkey for 3 times. The fluids were collected with 10 cm dish and then was transferred to 15 ml centrifuge tube. The cells in the fluids were further collected by centrifugation at 500 g for 5 min and used for RNA sequencing.

Serum Cytokine and Chemokine Analysis

The serum and BALF samples were collected for analysis of cytokine and chemokine. Concentration of granulocyte colony-stimulating factor (G-CSF), granulocyte-macrophage colony-stimulating factor (GM-CSF), interferon (IFN)-γ, interleukin (IL)-1 receptor antagonist, IL-1β, IL-2, IL-4, IL-5, IL-6, IL-8, IL-10, IL-12/23 (p40), IL-13, IL-15, IL-17, IL-18, monocyte chemotactic protein (MCP)-1, macrophage inflammatory protein (MIP)-1α, MIP-1β, soluble CD40-ligand (sCD40L), transforming growth factor (TGF)-α, tumor necrosis factor (TNF)-α, vascular endothelial growth factor (VEGF) were determined using the Non-Human Primate Cytokine MILLIPLEX map 23-plex kit (Millipore, Cat #PRCYTOMAG-40K) according to the manufacturer's instructions.

Quantitative PCR

RNA extraction and quantitative real-time reverse transcription-polymerase chain reaction (qRT-PCR) were performed on nasal/throat/anal swab, blood and necropsied tissue samples collected from infected monkeys. The virus RNA was extracted from inactivated samples using Trizol LS Reagent (Invitrogen, Cat #10296010) according to the Direct-zol™ RNA MiniPrep protocol (ZYMO RESEARCH CORP, US). 50 μl of DNase/RNase-Free Water was used to elute RNA. Real time RT-PCR was used to quantify viral genome in samples using TaqMan Fast Virus 1-Step Master Mix (ThermoFisher, Cat #4444434) and purified viral RNA of SARS-CoV-2 as a standard curve, performed on CFX384 Touch Real-Time PCR Detection System (Bio-Rad, US). Conditions for RT-PCR were used as follows: 25° C. for 2 min, 50° C. for 15 min, 95° C. for 2 min, then 40 cycles at 95° C. 5 sec and 58° C. 31 sec. Primers and probe, specific for NP gene was synthesized according to sequences reported by Chinese Center for Disease Control and Prevention (CDC).

```
Target-2-F:
                                        (SEQ ID NO: 30)
GGGGAACTTCTCCTGCTAGAAT,

Target-2-R:
                                        (SEQ ID NO: 31)
CAGACATTTTGCTCTCAAGCTG,

Target-2-P:
                                        (SEQ ID NO: 32)
5'-FAM-TTGCTGCTGCTTGACAGATT-TAMRA-3'
```

In each run, standard dilutions of counted RNA standards were run in parallel, to calculate copy numbers in the samples.

Histopathology and Immunohistochemistry

Autopsies of the rhesus macaques were performed according to a standard protocol. After the dissection, the major organs were grossly examined. The lung tissues were harvested, fixed in 10% neutral-buffered formalin solution, embedded in paraffin and 2 μm tissue sections were prepared. For Hematoxylin & Eosin (H&E) staining, slides were stained with Hematoxylin (Leica, Cat #3801591) and Eosin (Leica, Cat #3801594) (H&E) prior to microscopic pathologic analysis. Histopathological analysis of tissue slides was performed by pathologists blinded to the group assignment of the animals. Alcian blue-periodic acid-Schiff (AB-PAS) staining was performed by the AB-PAS staining kit (Servicebio, Cat #G1049). To perform immunohistochemistry staining of macrophage, the anti-CD68 primary antibody (abcam, Cat #ab213098) was used. For quantitative statistics of macrophage change, the corresponding second antibody used is HRP conjugated Goat Anti-Mouse IgG (H+L) (Servicebio, Cat #GB23301). The whole slide images were collected using Pannoramic DESK (3D HISTECH) and analyzed with Caseviewer C.V 2.3 and Image Pro plus 6.0.

Statistical Analysis

For statistical analysis, P values were calculated by t-test (when comparing only two groups) or one-way ANOVA (when comparing more than two groups) using GraphPad Prism 8. with default parameters. Error bars represent SEM and P<0.05 was considered statistically significant (ns, not significant, *P<0.05, P<0.01, *P<0.001, ****P<0.0001).

Key Resources

| REAGENT or RESOURCE | SOURCE | IDENTIFIER |
|---|---|---|
| Antibodies | | |
| Mouse Anti-CD68 antibody | abcam | Cat# ab213098 |
| HRP conjugated Goat Anti-Mouse IgG (H + L) | Servicebio | Cat# GB23301 |
| Chemicals, Peptides, and Recombinant Proteins | | |
| Tween-80 | BioFroxx | Cat# 1716 |
| phosphate buffered saline (PBS) | Gibco | Cat# 21-040-CVC |
| Trizol LS Reagent | Invitrogen | Cat# 10296010 |
| Paraformaldehyde | DingGuo | Cat# AR-0211 |
| Trypsin-EDTA (0.05%), phenol red | Gibco | Cat# 25200 |
| Penicillin-streptomycin | Solarbio | Cat# P1400 |
| Fetal Bovine Serum | Gibco | Cat# 10099-141C |
| DMEM, high glucose | Gibco | Cat# 11995500BT |
| Ketamine hydrochloride | Beikang | Cat# 100761663 |
| Hematoxylin | Leica | Cat# 3801591 |
| Eosin | Leica | Cat# 3801594 |
| DMSO | Life Science | Cat# 1087C114 |
| Critical Commercial Assays | | |
| Non-Human Primate Cytokine MILLIPLEX map 23-plex kit | Millipore | Cat# PRCYTOMAG-40K |
| TaqMan Fast Virus 1-Step Master Mix | ThermoFisher | Cat# 4444434 |
| Direct-zol RNA MiniPrep Kit | Zymo Research | Cat# R2050 |
| AB-PAS staining kit | Servicebio | Cat#G1049 |
| Deposited Data | | |
| RNA-seq data | This paper | GEO: GSE |
| Experimental Models: Cell Lines | | |
| Vero-E6 cell | This paper | N/A |
| Experimental Models: Organisms/Strains | | |
| Monkey: | Rhesus macaques | N/A |
| Oligonucleotides | | |
| Target-2-F | Lu et al., 2020 | N/A |
| Target-2-R | Lu et al., 2020 | N/A |
| Target-2-P | Lu et al., | N/A |
| Software | | |
| Image Pro plus 6.0 | Media Cybernetics | http://imagepro.biz/index.php |
| Caseviewer C.V 2.3 | 3D HISTECH | https://www.3dhistech.com/caseviewer |
| Bio-Rad CFX Connect Real-Time System | Bio-Rad | http://www.bio-rad.com/en-us/product/cfx-connect-real-time-pcr-detection-system |
| GraphPad Prism 8 | GraphPad Software | https://www.graphpad.com |

Figure 8A:
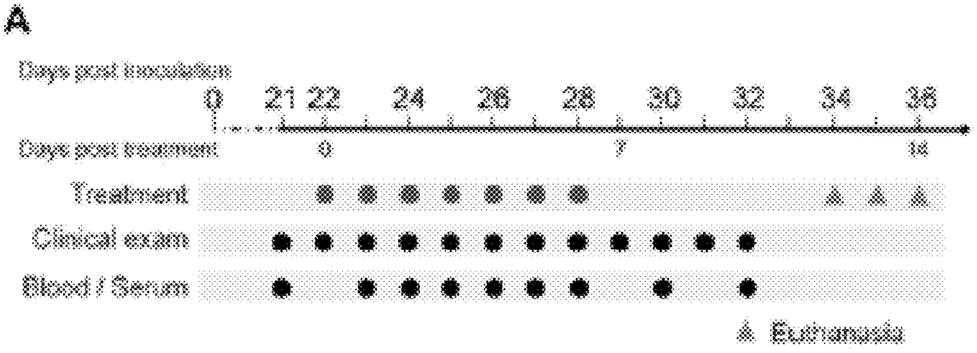
FIG. 8. SSK1 Effectively Repairs COVID-19 Pneumonia at the Late Stage of SARS-CoV-2 Infection (A) Scheme of the experimental design of late-stage SSK1 intervention. Black dot, measurement of clinical signs and blood sample at the indicated time points. Red dot, treatment. Brown triangle, sample collections following euthanasia. (B) Body weight changes of SARS-CoV-2-infected monkeys with vehicle, low dosage (0.5 mg/kg) or high dosage (2.0 mg/kg) of SSK1 between 22 and 32 dpi. (C) Necropsy images of lungs show that SSK1 treatment reduced the lesions of lungs from SARS-CoV-2-infected monkeys. Left, vehicle treatment; middle, 0.5 mg/kg; right, SSK1 treatment, 2.0 mg/kg. White circle, lung lesions. (D) H&E staining images show that SSK1 treatment improved the pneumonia of monkeys that were infected with SARS-CoV-2. Top, from left to right, representative H&E images of lungs of monkeys treated with vehicle, 0.5 mg/kg or 2.0 mg/kg SSK1; bottom, high magnification images of the boxed area in the top line. Arrow, hemorrhage. Asterisk, edema. Scale bars, top: 200 μm; bottom: 50 μm. See also FIG. 12.

Results:

SSK1 Effectively Improved COVID-19 Pneumonia at the Late Stage of SARS-CoV-2 Infection Because delayed lung recovery from SARS-CoV-2-induced pneumonia has been found in patients and nonhuman primate models (Wen et al., 2020; Munster et al., 2020), we first studied the therapeutic effects of SSK1 at the late stage of SARS-CoV-2 infection (FIG. 8A). We tested late intervention by SSK1 using our previously established SARS-CoV-2-infected rhesus macaque models, in which the virus was almost cleared from 14 days post inoculation (dpi) (Lu et al., 2020). Nine rhesus macaques were divided into three groups: Vehicle (RM1-RM3), 0.5 mg/kg SSK1 (RM4-RM6) and 2.0 mg/kg SSK1 (RM7-RM9), each group contains one young, one adult, and one elderly monkey (Table 4). Treatment was started from 22 dpi by intravenous injection for 7 consecutive days, and clinical sign data were collected for further analysis (FIG. 8A). Animals were euthanized for pathological analysis 5 days after the treatments stopped.

Figure 8B:
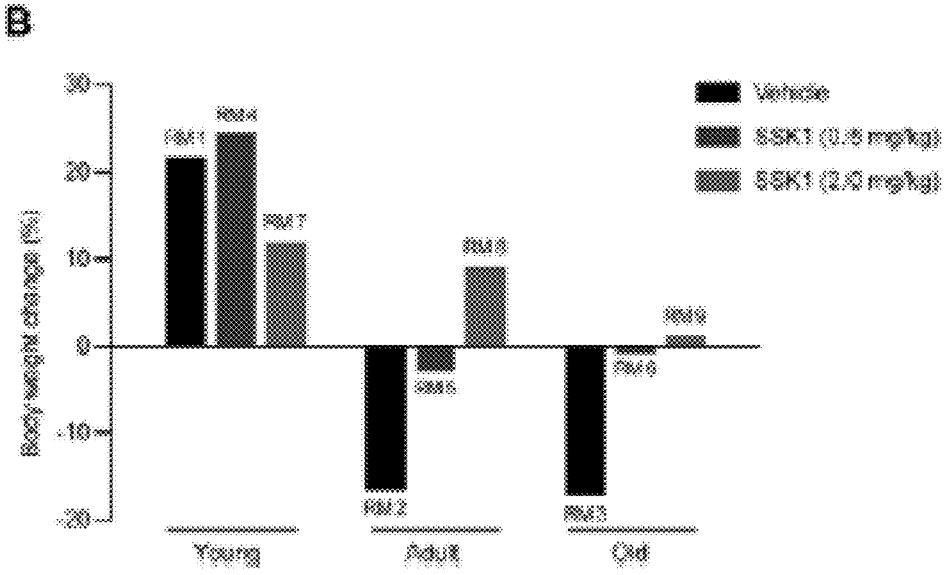
Figure 8C:
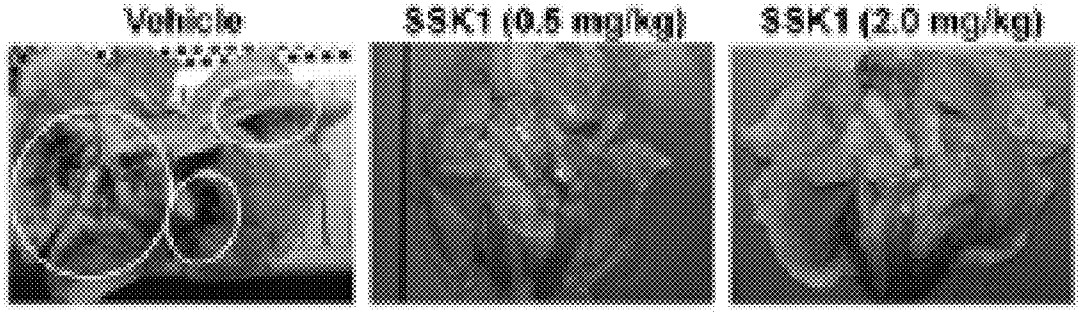

We monitored the clinical signs throughout the entire experiment and found that SSK1 treatment effectively prevented body weight loss, whereas vehicle-treated adult and old monkeys showed obvious weight loss up to 17% (FIG. 8B). The body weight of young monkeys kept increasing from 22 dpi, which was possibly because they were still at the developmental stage (FIG. 8B). We further analyzed lung injuries in the animals, and severe bright red lesions in the lungs were observed grossly in two of three vehicle-treated rhesus macaques (FIG. 8C; Table 4), suggesting continuous pneumonia at the very late stage of the infection. Importantly, among all six SSK1-treated monkeys, we only found one exhibiting new lung lesions (FIG. 8C; Table 4). Next, we investigated the therapeutic effects of SSK1 at the histopathological level. In the vehicle-treated group, hematoxylin and eosin (H&E) staining of lung sections showed a variable degree of thickened alveolar septum, edema and hemorrhage. This diseased phenotype was greatly improved in the SSK1-treated group (FIG. 1D and S1; Table 4). The severity of histologic lesions was measured based on predetermined histology assessment criteria. Pulmonary histology assessment further showed a reduction in histologic lesions in SSK1-treated animals (Table 4). Collectively, these results suggested that SSK1 improved pulmonary recovery from pneumonia of SARS-CoV-2 infection at late stage.

Figure 9B:
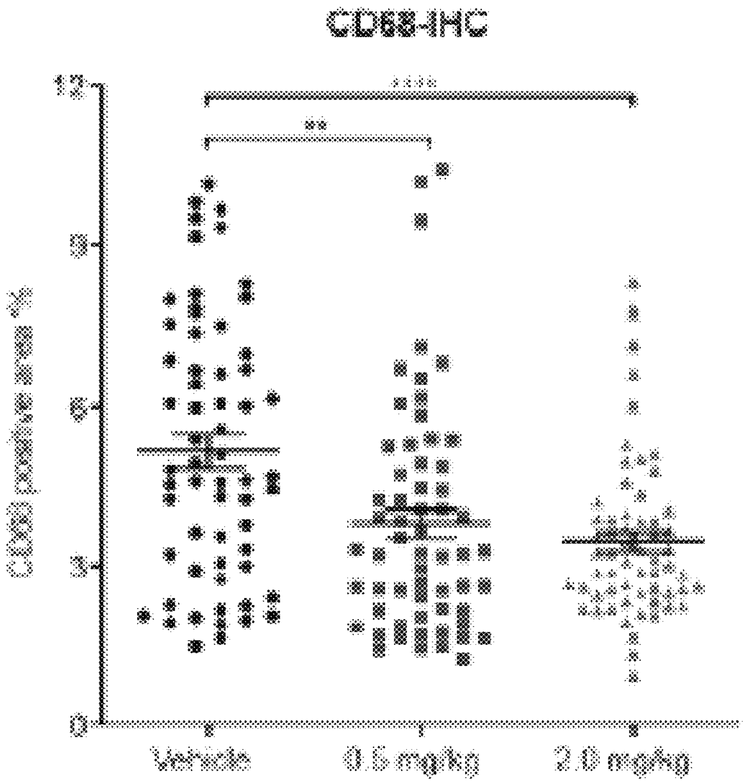
FIG. 9. SSK1 Decreased Macrophage Infiltration and Reduced Inflammation during Pulmonary Recovery. (A) Immunohistochemistry (IHC) analysis for CD68 in lung tissues collected from SARS-CoV-2-infected monkeys treated with vehicle, 0.5 mg/kg or 2.0 mg/kg SSK1. Top, low magnification images; bottom, high magnification images of the boxed area in the top line. Scale bar, top: 100 μm; bottom: 25 μm. (B) Quantification of the immunohistochemistry staining of CD68-positive cells in lung tissues after treatment. Analyzed in 20 random fields (0.75 mm2) per animal, 3 animals per group. Each data point represents an independent field of view in the IHC slides. Data was analyzed with one-way ANOVA, all error bars represent SEM, P<0.01, **P<0.0001. (C) Concentration change of inflammatory cytokines in serum samples from old monkeys between 21 and 28 dpi. (D) Concentration measurement for IL-18 in serum samples from SARS-CoV-2 infected monkeys before and after SSK1 treatment (2.0 mg/kg). Arrow, starting point of administration.

SSK1 Decreased Macrophage Infiltration and Reduced Inflammation During Pulmonary Recovery Next, we characterized the infiltration of macrophages by immunohistochemistry staining of the macrophage marker CD68. A large number of CD68-positive cells were found in the alveolar interstitium and a few within alveoli in vehicle-treated monkeys, suggesting the infiltration of macrophages after infection (FIG. 9A). SSK1 treatment significantly reduced macrophage infiltration, especially at high dosages, in the elderly group (FIG. 9B), which is consistent with our previous findings that SSK1 reduced macrophages in the natural aged mouse model (Cai et al., 2020).

Figure 9D:
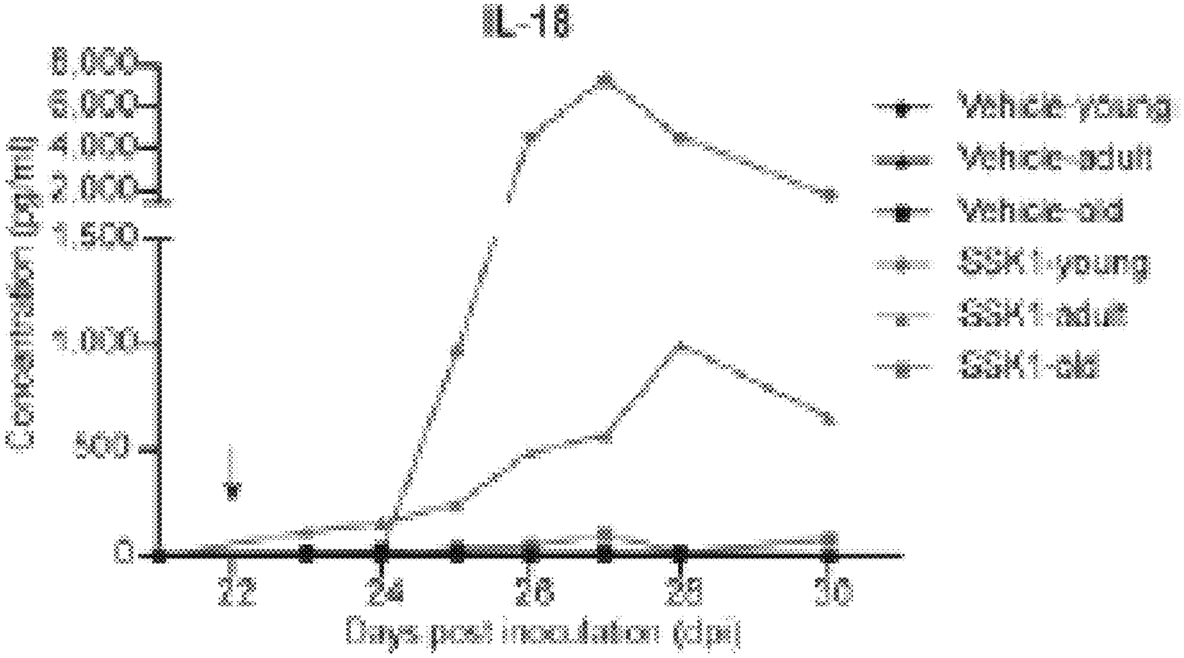
Figure 9C:
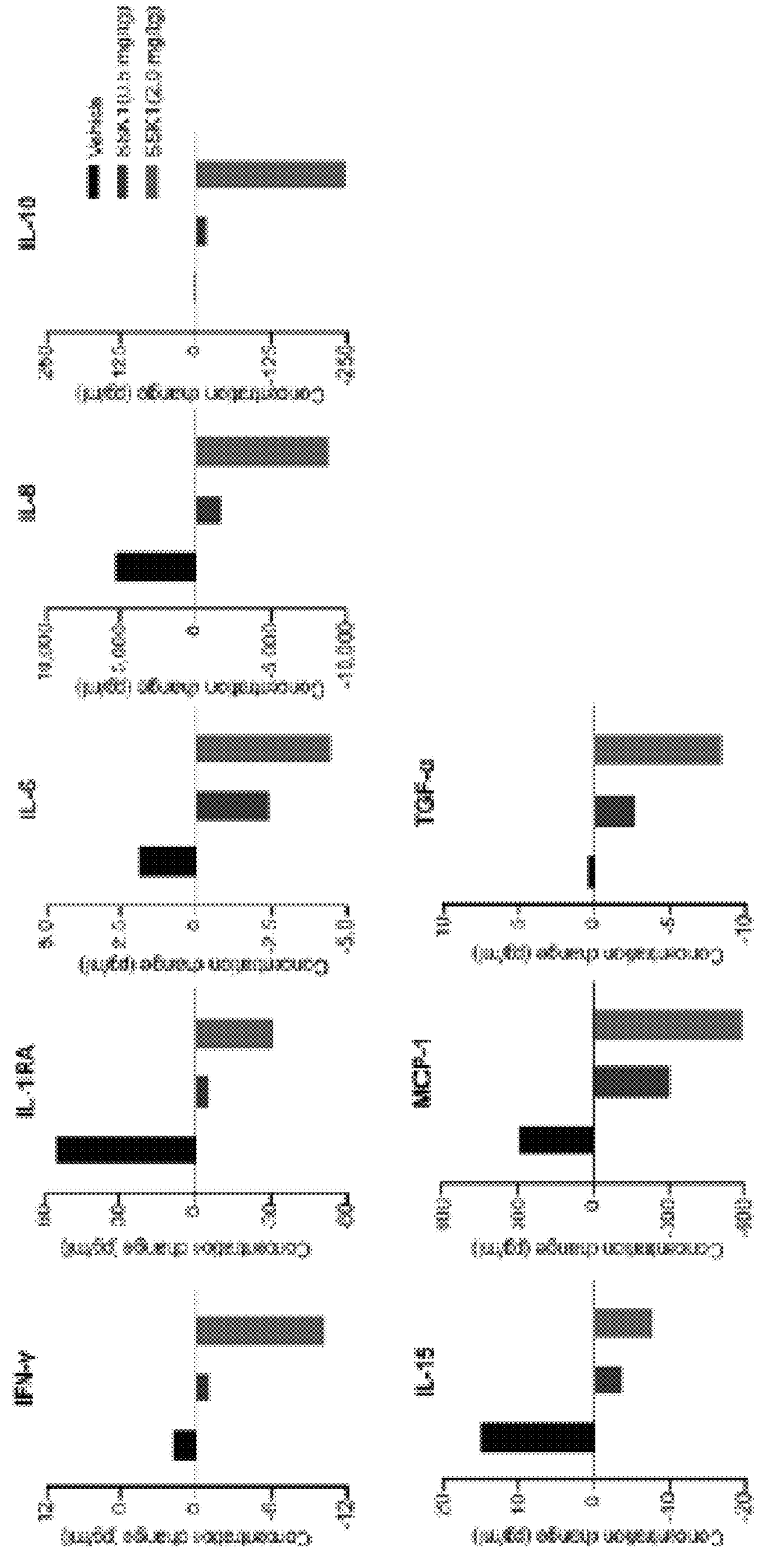

To investigate the serum levels of various inflammatory cytokines that have been thought to play a key role in the progression of severe COVID-19 pneumonia, we compared the concentrations of cytokines in blood samples before (21 dpi) and after (28 dpi) SSK1 treatment. For the SSK1-treated old monkeys, inflammatory cytokines in blood, including IL-6, IL-8, IL-10, IL-15, TGF-α and MCP1, were reduced at 28 dpi compared with 21 dpi, especially at the high dosage (2 mg/kg), suggesting attenuation of inflammation. In contrast, these cytokines were increased in vehicle-treated monkeys (FIG. 9C). Interestingly, in all high-dosage SSK1-treated monkeys, we found an increased level of IL-18, which is a protective cytokine in viral infection and has been found to be upregulated in COVID-19 patients during the period of rehabilitation (FIG. 9D) (Wen et al., 2020; Dinarello et al., 2013; Golonka et al., 2020). Collectively, our results suggested that SSK1 effectively regulated inflammatory cytokines in coordinating lung recovery in SARS-CoV-2-infected monkeys.

SSK1 Reduces Clinical Signs and Inflammatory Damages to the Lungs in the Early Stage of SARS-CoV-2 Infection Because SSK1 showed beneficial effects in treating symptoms induced by SARS-CoV-2 infection at late stage, we asked whether an early intervention by SSK1 could affect SARS-COV-2 elimination or alleviate infection-induced symptoms in the presence of the virus. To this end, four monkeys were randomly assigned to two groups of two animals. All animals were infected with SARS-CoV-2, followed by treatments with 2 mg/kg SSK1 (M1, M2) or vehicle (M3, M4) from 0 dpi. Administration was performed daily for 7 consecutive days, and animals were euthanized and necropsied after treatment was completed (FIG. 10A).

Figure 10C:
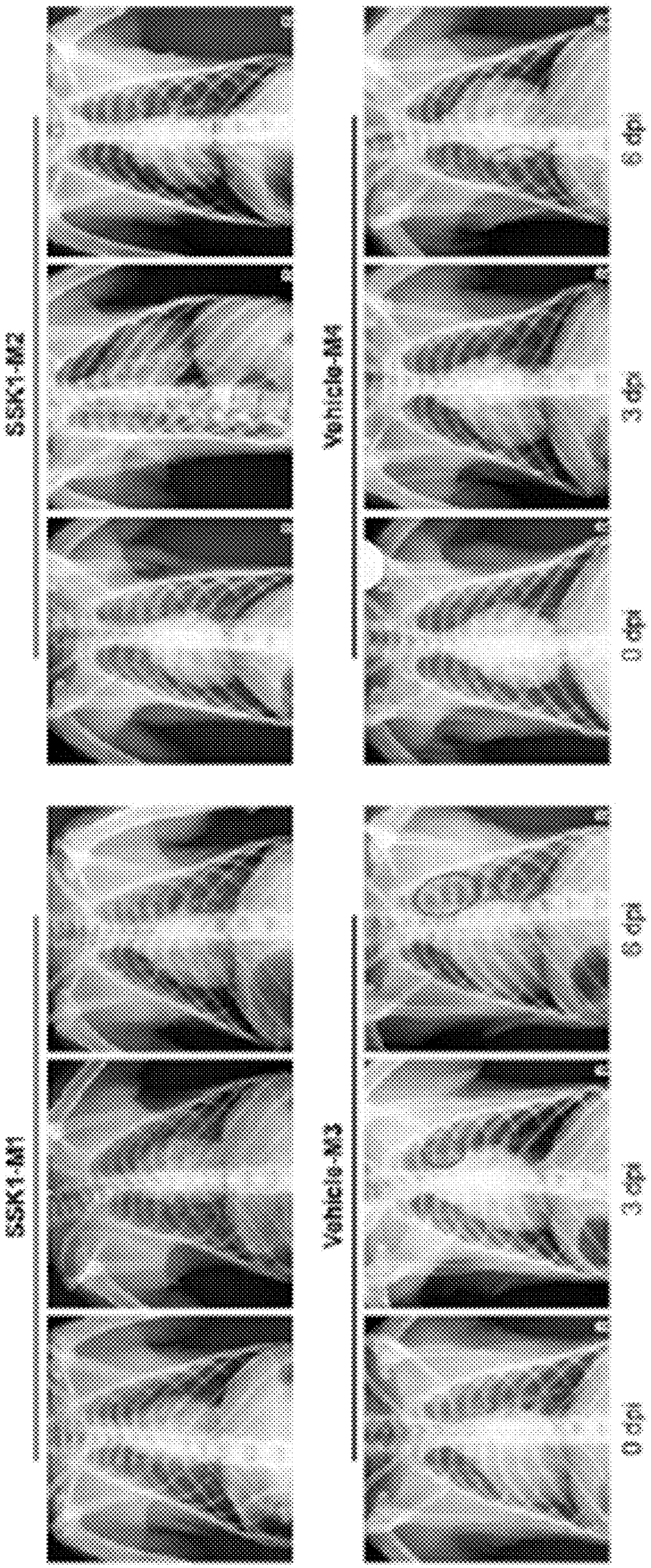
Figure 13D:
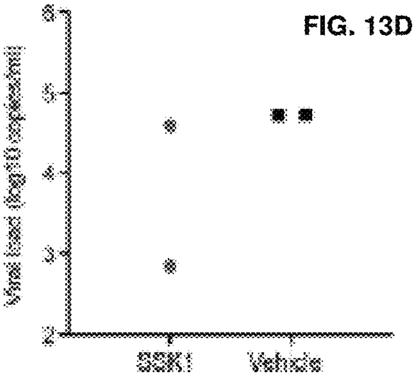
Figure 13A:
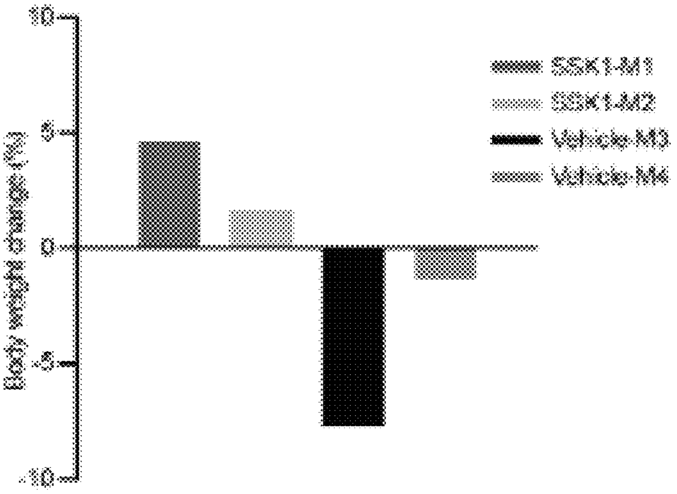
Figure 13A:
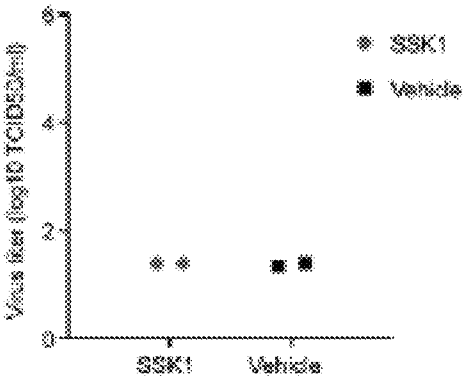
Figure 13C:
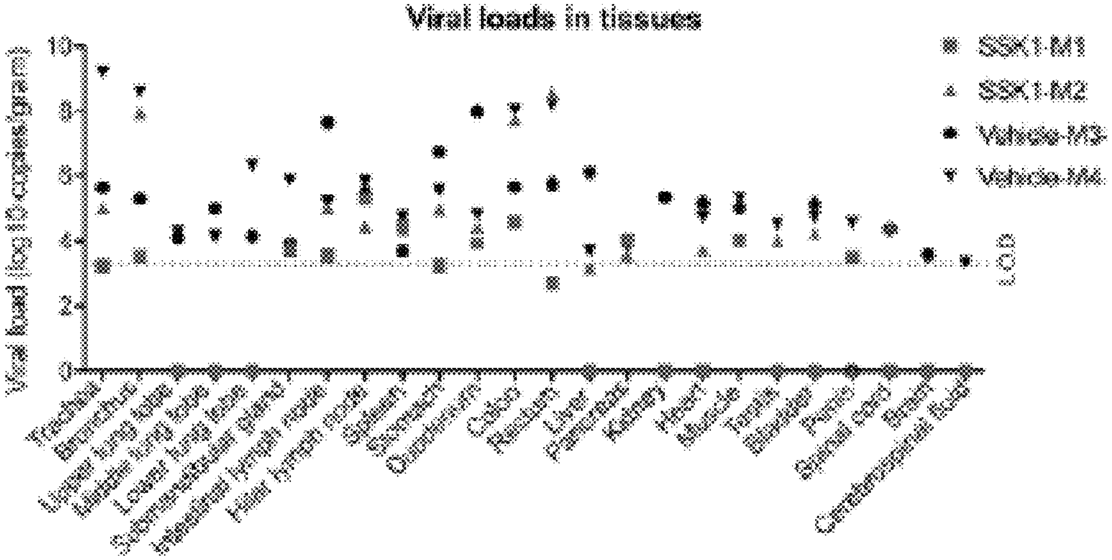
Figure 13B:
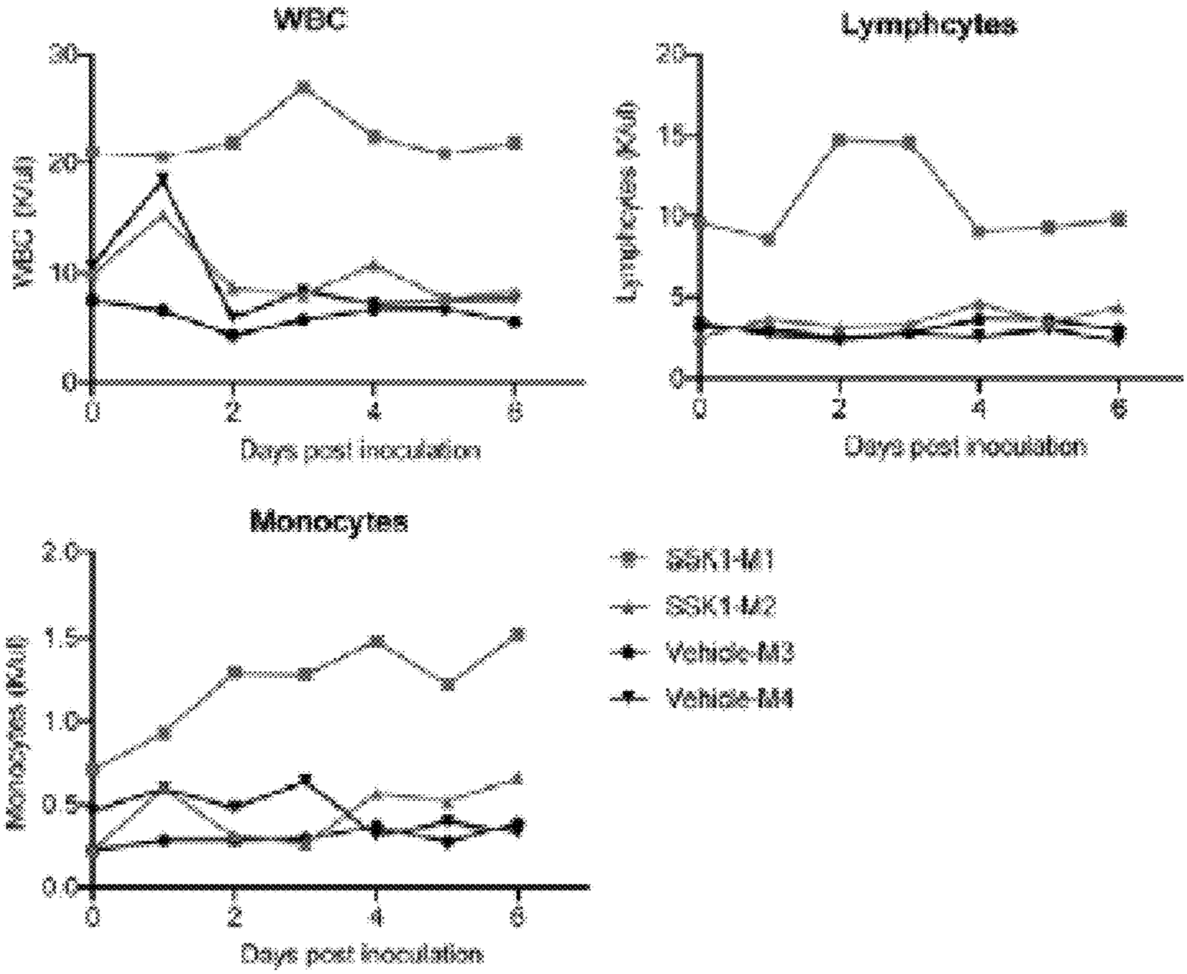

To investigate the effects of SSK1 treatment during SARS-CoV-2 infection at early stage, we performed clinical examinations daily. Significant elevation of body temperature was observed in the vehicle-treated group (even up to 40.0° C.), whereas it was relatively stable in the SSK1-treated group (FIG. 10B). We also observed weight loss in the vehicle-treated animals, but the weight of the SSK1-treated group remained constant (FIG. 13A). To further analyze the symptoms of pneumonia, dorsal-ventral chest X-ray (CXR) tests were performed, which showed progression of pulmonary infiltrates in the vehicle-treated animals from 3 dpi to 6 dpi, suggesting the aggravated pneumonia (FIG. 10C). In contrast, no progression was found at 6 dpi compared to 3 dpi in the SSK1-treated groups. Notably, M2 showed no signs of pneumonia on X-ray throughout the experiment (FIG. 10C). Ground-glass opacification appeared in the lungs of M1 at 3 dpi, which may be due to the abnormal basal immune status (FIG. 13B). Collectively, these results suggested a beneficial effect of SSK1 in the improvement of clinical symptoms of COVID-19.

To explore the influence of SSK1 on virus clearance, we detected the virus load in swabs (nose, throat, anal) and blood samples. We found no delay but even faster reduction in virus shedding in the SSK1-treated group (FIG. 10D). In addition, the viral load in the respiratory tract tissues and multiple organs of the SSK1 group was grossly lower than that of the vehicle-treated group (FIG. 14C), suggesting no interruption on the antiviral response by early SSK1 intervention.

Figure 11A:
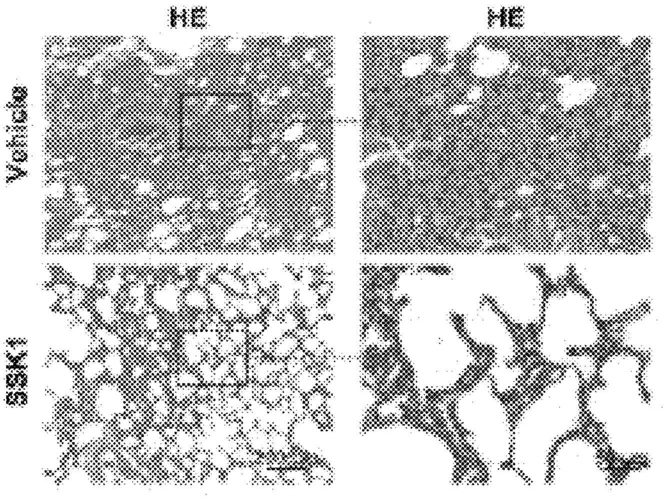
Figure 11B:
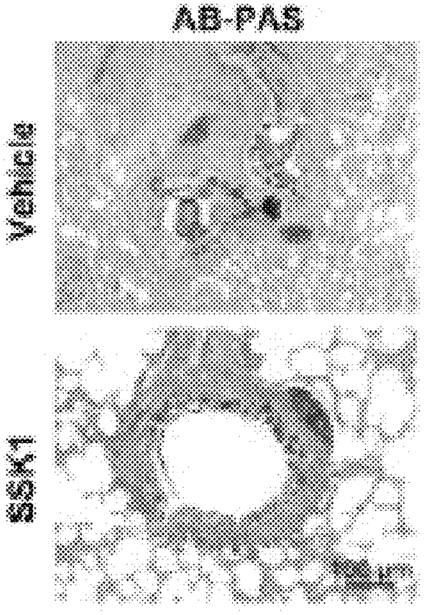
Figure 11D:
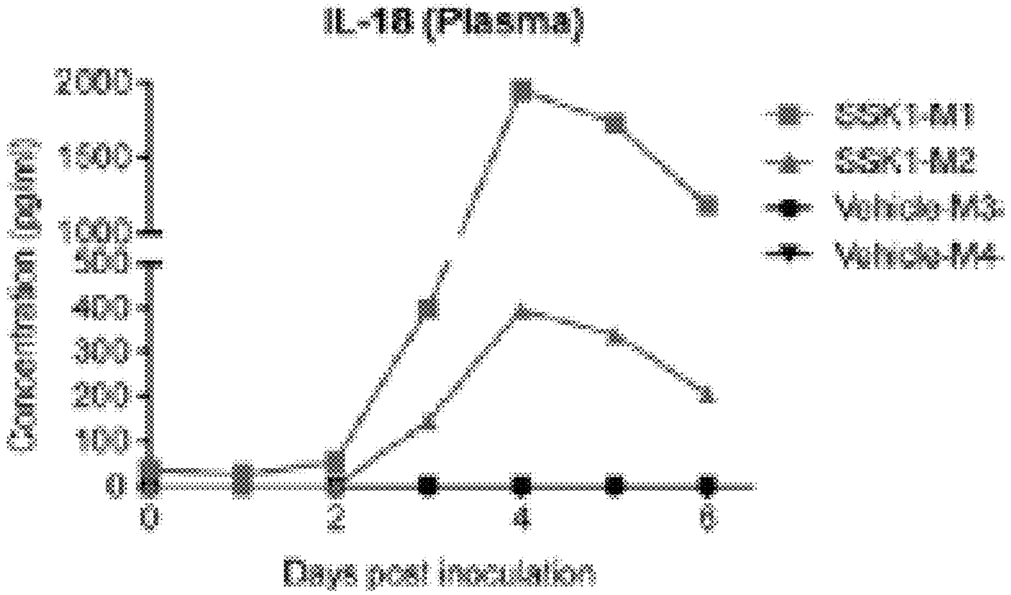

Next, we performed necropsy in all four animals after treatment. There were red punctate lesions in the vehicle-treated monkeys (FIG. 14A). No obvious lung lesions were found in SSK1-treated M2, which was consistent with the radiographs. Some brown punctate lesions were observed in the lungs of M1 (FIG. 14A), which may be related to the abnormal inflammation characteristics at baseline (FIG. 13C). In addition to the lung, we also found large necrotic lesions in the livers of the animals in the vehicle-treated group, consistent with the clinical observation (Lei et al., 2020), but not in the SSK1-treated group (FIG. 14B). Histopathology analysis showed severe lesions in the control animals; alveolar cavities were filled with abundant exudation, fragments and inflammatory cells, accompanied by serious edema, which indicated diffuse interstitial pneumonia. In contrast, in the SSK1-treated group, we only observed minimally thickened alveolar septum and focal edema (FIG. 4A and S3C), and M1 also had local pulmonary hemorrhages (FIG. 14D). Alcian blue-periodic acid-Schiff (AB-PAS) staining showed that SSK1 treatment recovered the airway narrowing and extensive mucinous secretions. (FIG. 11B).

Figure 11C:
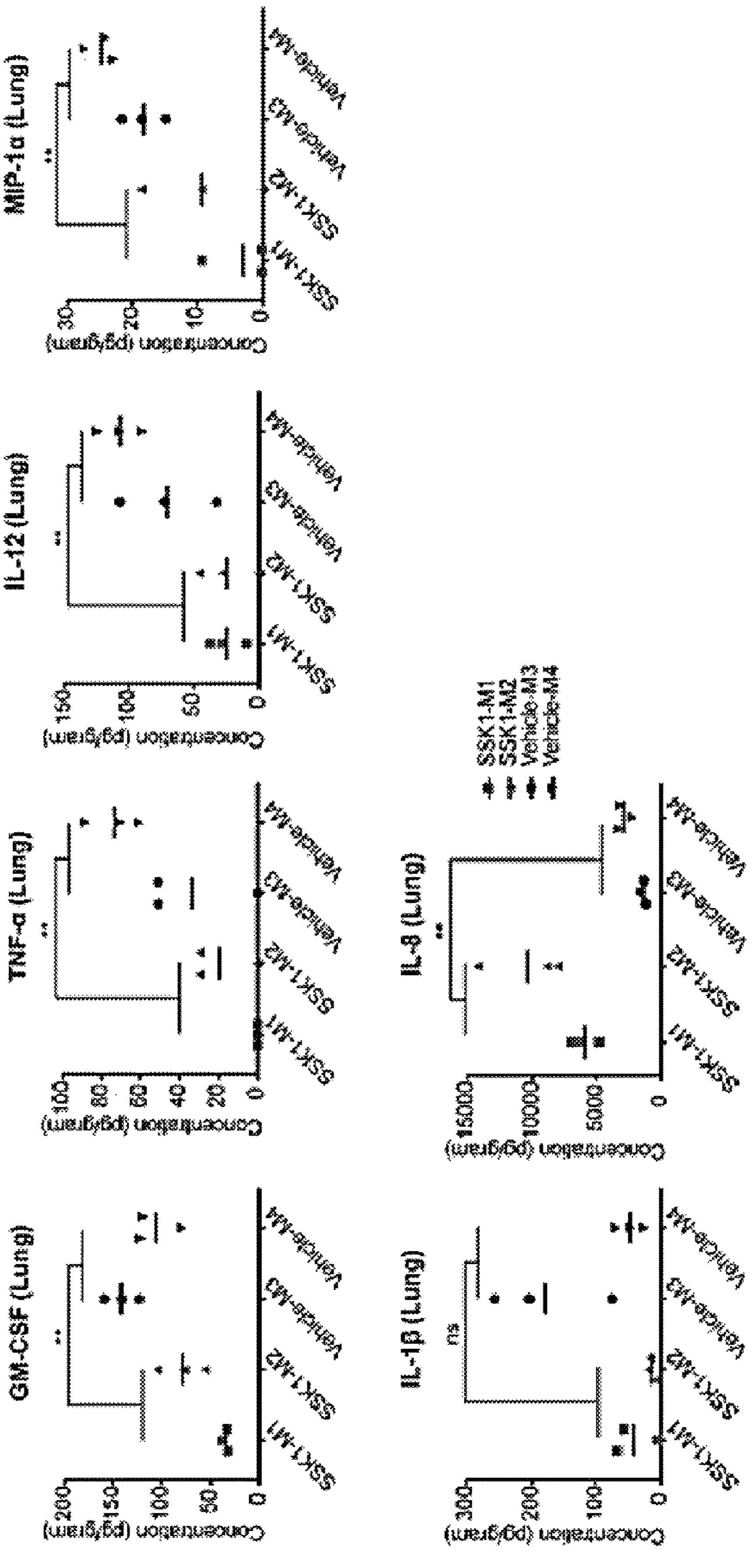

We next measured the changes in the levels of cytokines in serum and lung tissues. The concentrations of inflammatory cytokines, including GM-CSF, IL-1β, IL-12, MIP-1A, and TNF-α, were lower in the lung tissues of SSK1-treated animals, suggesting reduced inflammation in the infected lungs (FIG. 11C). Particularly, the level of IL-18 in the SSK1-treated group increased significantly (FIG. 11D), which was consistent with our observations in late-stage treatment (FIG. 9D). Collectively, our results suggested that early treatment with SSK1 reduced inflammation and ameliorated the pulmonary pathology of SARS-CoV-2 infection.

We tested the ability of SSK2 to selectively kill senescent cell in vitro and found that SSK2 can efficiently and selectively kill β-galactosidase positive senescent human embryonic fibroblasts (HEFs) in a dose-dependent manner (FIG. 15A, B).

Senescent cell accumulation plays a causative role in the development of osteoarthritis (OA) and selectively elimination of senescent cell could be an effective treatment strategy for OA patients (Jeon O, Kim C, Laberge R M, et al. Local clearance of senescent cells attenuates the development of post-traumatic osteoarthritis and creates a pro-regenerative environment[J]. Nature Medicine, 2017, 23(6): 775-781). Therefore, we tested the ability of SSK2 to kill OA chondrocytes and found that SSK2 can efficiently eliminate primary human chondrocytes isolated from Osteoarthritis patient (FIG. 16A, B and FIG. 17).

Discussion

In this study, we demonstrated that the small molecule SSK1 effectively treated COVID-19 pneumonia by managing macrophage infiltration to attenuate inflammation. Improved clinical symptoms, more stable body temperature, less body weight loss and better chest X-ray performance were observed in SSK1-treated animals. Consistent with the findings during autopsy, SSK1-treated animals had essentially normal pulmonary tissue with fewer and less severe lung and liver lesions on histopathology examination. In addition, reductions in macrophage accumulation and proinflammatory cytokine release were also observed in SSK1-treated animals. These results suggest the promising therapeutic potential of SSK1 in treating pneumonia and hyperinflammation in SARS-CoV-2 infection.

One major finding was that SSK1 showed efficient therapeutic efficacy in elderly monkeys infected with SARS-CoV-2. Body weight loss, elevation of multiple inflammatory cytokines and macrophage infiltration in the aged infection group were significantly reduced by SSK1 treatment (FIGS. 1 and 2). The reduction of inflammatory factors by SSK1 treatment was also observed in aged mice in our previous study (Cai et al., 2020). The anti-inflammatory effects of SSK1 in aged individuals are of great importance in treating COVID-19 because this disease has higher mortality in senior populations who also have basal chronic inflammation (Zhou et al., 2020). Previous studies showed that physiological lung aging leads to immunosenescence of innate and adaptive immune responses, thereby resulting in higher basic levels of cytokines and inflammatory cell infiltration in the lung (Cho and Stout-Delgado, 2020). Therefore, SSK1 may have a better therapeutic effect for the elderly population which has a higher rate of severe COVID-19.

SSK1 is the first anti-inflammatory treatment that has been studied for COVID-19 using nonhuman primate models. SSK1 showed the benefits of anti-inflammation without affecting antiviral effects (FIG. 3D and S3C), and SSK1 treatment also led to a reduction in macrophage infiltration in the lung (FIGS. 2A and 2B). In addition to their important roles in regulating inflammation, macrophages have also been shown to play a key role in antibody-dependent enhancement (ADE) and complement-mediated thrombosis (Yip et al., 2014; Risitano et al., 2020). After SARS-CoV-2 infection, increased IgG responses and the number of antibodies were found in severe patients, suggesting the possibility of ADE as a potential mechanism of COVID-19 severity (Zhao et al., 2020; Zhang et al., 2020). In support of the importance of ADE in coronavirus-induced diseases, ADE was also found in SARS-CoV infections (Jaume et al., 2011; Liu et al., 2019), by which the complex of antibodies and SARS-CoV can enter macrophages through Fcγ receptors (FcγR), resulting in a strong proinflammatory response and an aggravation of pneumonia. Therefore, our strategy indicates an applicative potential in the development of antibody-based therapies and vaccines. On the other hand, the complement system has been found to be overactivated in the lungs of COVID-19 patients with aggravated lung injuries (Magro et al., 2020), and previous studies noted that coronavirus infection, such as SARS-CoV, can activate complement C3, leading to an overactivated immune response through macrophages and neutrophils and contributing to thrombotic microangiopathies (Gralinski et al., 2018). Accordingly, transiently targeting macrophages by SSK1 may also have beneficial effects in reducing complement-associated inflammation and thrombosis during SARS-CoV-2 infection.

In summary, our work demonstrates a novel strategy to control inflammation by targeting macrophages in COVID-19. Importantly, we did not observe any adverse effects in our treated monkeys, and our previous work also demonstrates its safety in vivo, which collectively indicates the practical value of SSK1 for clinical translations. It would be promising to combine our anti-inflammatory small molecule compound with anti-viral drugs to achieve the best clinical outcome in COVID-19 patients.

TABLE 4

Clinical and pathological observations in rhesus macaques infected with SARS-CoV-2 and treated with SSK1 or vehicle at late stage

| Treatment | Vehicle-DMSO | | | SSK1-0.5 mg/kg | | | SSK1-2.0 mg/kg | | |
|---|---|---|---|---|---|---|---|---|---|
| Animal | RM1 | RM2 | RM3 | RM4 | RM5 | RM6 | RM7 | RM8 | RM9 |
| Age | Young 1-year | Adult 5-year | Old 15-year | Young 1-year | Adult 5-year | Old 17-year | Young 1-year | Adult 5-year | Old 18-year |
| Body weight change (32 dpi vs 22 dpi %) | +22.22 | −17.24 | −17.72 | +25.00 | −3.45 | −1.25 | +12.50 | +9.68 | +1.82 |
| Necropsy | Obvious bright red lesions in lung | No visible lesion in lung | Obvious bright red lesions in lung | A very small lesion in lung | Slight lesion in lung | No visible lesion in lung | No visible lesion in lung | No visible lesion in lung | A dark obsolete lesion in lung |

TABLE 4-continued

Clinical and pathological observations in rhesus macaques infected with SARS-CoV-2 and treated with SSK1 or vehicle at late stage

| Treatment | Vehicle-DMSO | | | SSK1-0.5 mg/kg | | | SSK1-2.0 mg/kg | | |
|---|---|---|---|---|---|---|---|---|---|
| Pathological evaluation by H&E staining | | | | | | | | | |
| Inflammatory cell infiltration | ++ | ++ | ++ | ++ | + | + | + | + | + |
| Hemorrhage | ++ | + | ++ | + | − | − | − | − | − |
| Thickened alveolar septum | ++ | +++ | ++ | + | + | + | + | + | + |
| Edema | ++ | ++ | ++ | + | + | + | + | + | + |

TABLE 5

Clinical and pathological observations in adult rhesus macaques infected with SARS-CoV-2 treated with SSKI at early stage

| Treatment | SSK1-2.0 mg/kg | | Vehicle-DMSO | |
|---|---|---|---|---|
| Animal | M1 | M2 | M3 | M4 |
| Age (adult) | 5-year | 5-year | 5-year | 5-year |
| Clinical observation | | | | |
| Increased respiration | − | − | + | − |
| Body weight change (%) | +4.62 | +1.64 | −7.69 | −1.33 |
| Increased temperature | light | light | higher | higher |
| X-ray progression | − | − | + | + |
| Necropsy (lung) | Deep brown punctate lesions | No visible lesions | Red punctate lesions | Red punctate lesions |

TABLE 5-continued

Clinical and pathological observations in adult rhesus macaques infected with SARS-CoV-2 treated with SSKI at early stage

| Treatment | SSK1-2.0 mg/kg | | Vehicle-DMSO | |
|---|---|---|---|---|
| Necropsy (liver) | No visible lesions | No visible lesions | Gross liver lesions | Gross liver lesions |
| Pathological evaluation by H&E staining | | | | |
| Inflammatory cell infiltration | + | + | + | ++ |
| Hemorrhage | + | − | + | + |
| Thickened alveolar septum | + | + | ++ | +++ |
| Edema | − | + | ++ | ++ |

TABLE 6

Clinical and pathological observations in adult rhesus macaques infected with SARS-CoV-2 treated with SSKI at early stage

| | | | Before treatment | After treatment | | | | | |
|---|---|---|---|---|---|---|---|---|---|
| | Treatment | Animal | 21 dpi | 23 dpi | 24 dpi | 25 dpi | 26 dpi | 27 dpi | 28 dpi | 30 dpi |
| AST (U/L) | Vehicle | RM1 | 52 | 52 | 30 | 33 | 36 | 43 | 53 | 39 |
| | | RM2 | 29 | 30 | 25 | 32 | 35 | 34 | 29 | 30 |
| | | RM3 | 31 | 29 | 32 | 35 | 34 | 42 | 27 | 25 |
| | 0.5 mg/kg | RM4 | 91 | 69 | 50 | 39 | 40 | 37 | 22 | 38 |
| | | RM5 | 24 | 19 | 20 | 18 | 18 | 23 | 17 | 18 |
| | | RM6 | 74 | 44 | 35 | 40 | 31 | 46 | 28 | 28 |
| | 2.0 mg/kg | RM7 | 61 | 56 | 38 | 32 | 59 | 56 | 44 | 46 |
| | | RM8 | 33 | 19 | 30 | 22 | n.d. | 28 | 24 | 26 |
| | | RM9 | 28 | 27 | 32 | 27 | 28 | 35 | 28 | 30 |
| ALT (U/L) | Vehicle | RM1 | 21 | 39 | 29 | 25 | 26 | 29 | 28 | 26 |
| | | RM2 | 20 | 21 | 20 | 23 | 28 | 24 | 21 | 26 |
| | | RM3 | 13 | 16 | 14 | 17 | 19 | 21 | 17 | 18 |
| | 0.5 mg/kg | RM4 | 26 | 44 | 46 | 39 | 31 | 33 | 19 | 28 |
| | | RM5 | 32 | 31 | 31 | 27 | 30 | 35 | 33 | 36 |
| | | RM6 | 74 | 65 | 50 | 46 | 39 | 47 | 34 | 41 |
| | 2.0 mg/kg | RM7 | 32 | 37 | 39 | 29 | 37 | 35 | 34 | 32 |
| | | RM8 | 76 | 46 | 50 | 36 | n.d. | 35 | 34 | 33 |
| | | RM9 | 28 | 26 | 37 | 29 | 27 | 27 | 26 | 41 |
| UA (μmol/L) | Vehicle | RM1 | 2 | 3 | 3 | 4 | 4 | 5 | 3 | 3 |
| | | RM2 | 5 | 2 | 7 | 2 | 3 | 3 | 2 | 3 |
| | | RM3 | 3 | 2 | 7 | 2 | 5 | 2 | 3 | 2 |
| | 0.5 mg/kg | RM4 | 8 | 4 | 4 | 4 | 1 | 6 | 3 | 6 |
| | | RM5 | 5 | 4 | 7 | 3 | 5 | 3 | 2 | 2 |
| | | RM6 | 9 | 1 | 2 | 3 | 1 | 4 | 1 | 4 |
| | 2.0 mg/kg | RM7 | 5 | 2 | 4 | 6 | 5 | 8 | 6 | 3 |
| | | RM8 | 13 | 4 | 3 | 2 | n.d. | 5 | 3 | 6 |
| | | RM9 | 10 | 0 | 2 | 5 | 6 | 3 | 1 | 5 |
| CRE-E (μmol/L) | Vehicle | RM1 | 30 | 31 | 29 | 30 | 32 | 32 | 34 | 31 |
| | | RM2 | 70 | 56 | 52 | 58 | 64 | 61 | 74 | 72 |
| | | RM3 | 69 | 61 | 57 | 61 | 65 | 66 | 81 | 73 |
| | 0.5 mg/kg | RM4 | 28 | 34 | 30 | 30 | 25 | 27 | 32 | 30 |
| | | RM5 | 55 | 41 | 38 | 31 | 40 | 38 | 48 | 41 |
| | | RM6 | 49 | 37 | 38 | 40 | 41 | 46 | 51 | 50 |

TABLE 6-continued

Clinical and pathological observations in adult rhesus macaques infected with SARS-CoV-2 treated with SSKI at early stage

| | | | Before treatment | After treatment | | | | | | |
|---|---|---|---|---|---|---|---|---|---|---|
| | Treatment | Animal | 21 dpi | 23 dpi | 24 dpi | 25 dpi | 26 dpi | 27 dpi | 28 dpi | 30 dpi |
| | 2.0 mg/kg | RM7 | 33 | 30 | 32 | 30 | 31 | 29 | 35 | 34 |
| | | RM8 | 55 | 45 | 50 | 42 | n.d. | 48 | 57 | 55 |
| | | RM9 | 58 | 46 | 57 | 50 | 52 | 54 | 63 | 50 |
| ALP (U/L) | Vehicle | RM1 | 1398 | 1522 | 1229 | 1281 | 1360 | 1312 | 1283 | 1395 |
| | | RM2 | 152 | 128 | 116 | 141 | 171 | 154 | 124 | 173 |
| | | RM3 | 102 | 96 | 83 | 92 | 94 | 108 | 82 | 107 |
| | 0.5 mg/kg | RM4 | 822 | 857 | 778 | 789 | 595 | 663 | 432 | 728 |
| | | RM5 | 124 | 94 | 86 | 66 | 74 | 75 | 67 | 89 |
| | | RM6 | 100 | 101 | 101 | 107 | 97 | 112 | 85 | 111 |
| | 2.0 mg/kg | RM7 | 685 | 101 | 101 | 107 | 97 | 112 | 85 | 111 |
| | | RM8 | 427 | 280 | 365 | 269 | n.d. | 321 | 292 | 397 |
| | | RM9 | 233 | 192 | 250 | 203 | 212 | 226 | 188 | 192 |

REFERENCES

AUYEUNG, T., LEE, J., LAI, W., CHOI, C., LEE, H., LEE, J., LI, P., LOK, K., NG, Y., and WONG, W. (2005). The use of corticosteroid as treatment in SARS was associated with adverse outcomes: a retrospective cohort study. J INFECTION 51, 98-102.

Boor, P., de Ruiter, P. E., Asmawidjaja, P. S., Lubberts, E., van der Laan, L., and Kwekkeboom, J. (2017). JAK-inhibitor tofacitinib suppresses interferon alfa production by plasmacytoid dendritic cells and inhibits arthrogenic and antiviral effects of interferon alfa. TRANSL RES 188, 67-79.

Cai, Y., Zhou, H., Zhu, Y., Sun, Q., Ji, Y., Xue, A., Wang, Y., Chen, W., Yu, X., and Wang, L., et al. (2020). Elimination of senescent cells by beta-galactosidase-targeted prodrug attenuates inflammation and restores physical function in aged mice. CELL RES.

Channappanavar, R., Fehr, A. R., Vijay, R., Mack, M., Zhao, J., Meyerholz, D. K., and Perlman, S. (2016). Dysregulated Type I Interferon and Inflammatory Monocyte-Macrophage Responses Cause Lethal Pneumonia in SARS-CoV-Infected Mice. CELL HOST MICROBE 19, 181-193.

Channappanavar, R., and Perlman, S. (2017). Pathogenic human coronavirus infections: causes and consequences of cytokine storm and immunopathology. SEMIN IMMUNOPATHOL 39, 529-539.

Cho, S. J., and Stout-Delgado, H. W. (2020). Aging and Lung Disease. ANNU REV PHYSIOL 82, 433-459.

de Wit, E., van Doremalen, N., Falzarano, D., and Munster, V. J. (2016). SARS and MERS: recent insights into emerging coronaviruses. NAT REV MICROBIOL 14, 523-534.

Dinarello, C. A., Novick, D., Kim, S., and Kaplanski, G. (2013). Interleukin-18 and IL-18 Binding Protein. FRONT IMMUNOL 4.

Giamarellos-Bourboulis, E. J., Netea, M. G., Rovina, N., Akinosoglou, K., Antoniadou, A., Antonakos, N., Damoraki, G., Gkavogianni, T., Adami, M., and Katsaounou, P., et al. (2020). Complex Immune Dysregulation in COVID-19 Patients with Severe Respiratory Failure. CELL HOST MICROBE.

Golonka, R. M., Saha, P., Yeoh, B. S., Chattopadhyay, S., Gewirtz, A. T., Joe, B., and Vijay-Kumar, M. (2020). Harnessing innate immunity to eliminate SARS-CoV-2 and ameliorate COVID-19 disease. PHYSIOL GENOMICS 52, 217-221.

Gralinski, L. E., Sheahan, T. P., Morrison, T. E., Menachery, V. D., Jensen, K., Leist, S. R., Whitmore, A., Heise, M. T., and Baric, R. S. (2018). Complement Activation Contributes to Severe Acute Respiratory Syndrome Coronavirus Pathogenesis. MBIO 9.

Grasselli, G., Zangrillo, A., Zanella, A., Antonelli, M., Cabrini, L., Castelli, A., Cereda, D., Coluccello, A., Foti, G., and Fumagalli, R., et al. (2020). Baseline Characteristics and Outcomes of 1591 Patients Infected With SARS-CoV-2 Admitted to ICUs of the Lombardy Region, Italy. JAMA 323, 1574.

Grein, J., Ohmagari, N., Shin, D., Diaz, G., Asperges, E., Castagna, A., Feldt, T., Green, G., Green, M. L., and Lescure, F., et al. (2020). Compassionate Use of Remdesivir for Patients with Severe Covid-19. The New England journal of medicine.

Huang, C., Wang, Y., Li, X., Ren, L., Zhao, J., Hu, Y., Zhang, L., Fan, G., Xu, J., and Gu, X., et al. (2020). Clinical features of patients infected with 2019 novel coronavirus in Wuhan, China. The Lancet 395, 497-506.

Jaume, M., Yip, M. S., Cheung, C. Y., Leung, H. L., Li, P. H., Kien, F., Dutry, I., Callendret, B., Escriou, N., and Altmeyer, R., et al. (2011). Anti-severe acute respiratory syndrome coronavirus spike antibodies trigger infection of human immune cells via a pH- and cysteine protease-independent FcgammaR pathway. J VIROL 85, 10582-10597.

Lei, F., Liu, Y. M., Zhou, F., Qin, J. J., Zhang, P., Zhu, L., Zhang, X. J., Cai, J., Lin, L., and Ouyang, S., et al. (2020). Longitudinal association between markers of liver injury and mortality in COVID-19 in China. HEPATOLOGY.

Liao, M., Liu, Y., Yuan, J., Wen, Y., Xu, G., Zhao, J., Cheng, L., Li, J., Wang, X., and Wang, F., et al. (2020). Single-cell landscape of bronchoalveolar immune cells in patients with COVID-19. NAT MED.

Liu, L., Wei, Q., Lin, Q., Fang, J., Wang, H., Kwok, H., Tang, H., Nishiura, K., Peng, J., and Tan, Z., et al. (2019). Anti-spike IgG causes severe acute lung injury by skewing macrophage responses during acute SARS-CoV infection. JCI insight 4.

Luo, P., Liu, Y., Qiu, L., Liu, X., Liu, D., and Li, J. (2020). Tocilizumab treatment in COVID-19: A single center experience. J MED VIROL.

Magro, C., Mulvey, J. J., Berlin, D., Nuovo, G., Salvatore, S., Harp, J., Baxter-Stoltzfus, A., and Laurence, J. (2020). Complement associated microvascular injury and thrombosis in the pathogenesis of severe COVID-19 infection: a report of five cases. TRANSL RES.

Merad, M., and Martin, J. C. (2020). Pathological inflammation in patients with COVID-19: a key role for monocytes and macrophages. NAT REV IMMUNOL.

Moore, J. B., and June, C. H. (2020). Cytokine release syndrome in severe COVID-19. SCIENCE 368, 473-474.

Munster, V. J., Feldmann, F., Williamson, B. N., van Doremalen, N., Perez-Perez, L., Schulz, J., Meade-White, K., Okumura, A., Callison, J., and Brumbaugh, B., et al. (2020). Respiratory disease in rhesus macaques inoculated with SARS-CoV-2. NATURE.

Page, C., Goicochea, L., Matthews, K., Zhang, Y., Klover, P., Holtzman, M. J., Hennighausen, L., and Frieman, M. (2012). Induction of alternatively activated macrophages enhances pathogenesis during severe acute respiratory syndrome coronavirus infection. J VIROL 86, 13334-13349.

Qi, F., Liu, M., Li, F., Lv, Q., Wang, G., Gong, S., Wang, S., Xu, Y., Bao, L., and Qin, C. (2019). Interleukin-37 Ameliorates Influenza Pneumonia by Attenuating Macrophage Cytokine Production in a MAPK-Dependent Manner. FRONT MICROBIOL 10.

Risitano, A. M., Mastellos, D. C., Huber-Lang, M., Yancopoulou, D., Garlanda, C., Ciceri, F., and Lambris, J. D. (2020). Complement as a target in COVID-19? Nature reviews. Immunology.

Ritchie, A. I., and Singanayagam, A. (2020). Immunosuppression for hyperinflammation in COVID-19: a double-edged sword? LANCET 395, 1111.

Russell, C. D., Millar, J. E., and Baillie, J. K. (2020). Clinical evidence does not support corticosteroid treatment for 2019-nCoV lung injury. The Lancet 395, 473-475.

Tay, M. Z., Poh, C. M., Rénia, L., MacAry, P. A., and Ng, L. F. P. (2020). The trinity of COVID-19: immunity, inflammation and intervention. Nature reviews. Immunology.

Wang, D., Hu, B., Hu, C., Zhu, F., Liu, X., Zhang, J., Wang, B., Xiang, H., Cheng, Z., and Xiong, Y., et al. (2020). Clinical Characteristics of 138 Hospitalized Patients With 2019 Novel Coronavirus-Infected Pneumonia in Wuhan, China. JAMA 323, 1061.

Wang, Y., Zhang, D., Du, G., Du, R., Zhao, J., Jin, Y., Fu, S., Gao, L., Cheng, Z., and Lu, Q., et al. (2020). Remdesivir in adults with severe COVID-19: a randomised, double-blind, placebo-controlled, multicentre trial. The Lancet.

Wen, W., Su, W., Tang, H., Le, W., Zhang, X., Zheng, Y., Liu, X., Xie, L., Li, J., and Ye, J., et al. (2020). Immune cell profiling of COVID-19 patients in the recovery stage by single-cell sequencing. CELL DISCOV 6.

Yang, X., Yu, Y., Xu, J., Shu, H., Xia, J., Liu, H., Wu, Y., Zhang, L., Yu, Z., and Fang, M., et al. (2020). Clinical course and outcomes of critically ill patients with SARS-CoV-2 pneumonia in Wuhan, China: a single-centered, retrospective, observational study. The Lancet Respiratory Medicine 8, 475-481.

Yip, M. S., Leung, N. H., Cheung, C. Y., Li, P. H., Lee, H. H., Daeron, M., Peiris, J. S., Bruzzone, R., and Jaume, M. (2014). Antibody-dependent infection of human macrophages by severe acute respiratory syndrome coronavirus. VIROL J 11, 82.

Zhang, Y., Zhong, Y., Pan, L., and Dong, J. (2020). Treat 2019 novel coronavirus (COVID-19) with IL-6 inhibitor: Are we already that far? Drug Discoveries & Therapeutics 14, 100-102.

Zhao, J., Yuan, Q., Wang, H., Liu, W., Liao, X., Su, Y., Wang, X., Yuan, J., Li, T., and Li, J., et al. (2020). Antibody responses to SARS-CoV-2 in patients of novel coronavirus disease 2019. CLIN INFECT DIS.

Zhou, F., Yu, T., Du R, Fan, G., Liu, Y., Liu, Z., Xiang, J., Wang, Y., Song, B., and Gu, X., et al. (2020). Clinical course and risk factors for mortality of adult inpatients with COVID-19 in Wuhan, China: a retrospective cohort study. LANCET 395, 1054-1062.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An agent the agent comprising:

(i)

Formula II

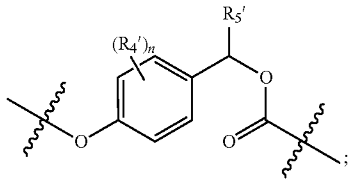

;

(ii)

Formula III

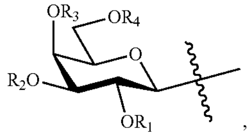

, and (iii) a cytotoxic moiety, wherein the cytotoxic moiety is gemcitabine, (a) wherein $R_1$, $R_2$, $R_3$, and $R_4$ are independently H, $R_5C(O)$—, $R_6OC(O)$—, $R_7R_8NC(O)$—, or $R_9PO_3^-$—, such that —$OR_x$ is independently an ester, a carbonate, a carbamate, or a phosphodiester group, respectively, where x is 1, 2, 3, or 4, wherein $R_5$, $R_6$, $R_7$, $R_8$, and $R_9$ are independently hydrogen, substituted alkyl, unsubstituted alkyl, substituted aryl, unsubstituted aryl, substituted heteroaryl, unsubstituted heteroaryl, substituted $C_3$-$C_{10}$ cyclyl, unsubstituted $C_3$-$C_{10}$ cyclyl, substituted $C_3$-$C_{10}$ heterocyclyl, unsubstituted $C_3$-$C_{10}$ heterocyclyl;

(b) wherein each $R_4'$ is independently nitro, cyano, amino, hydroxy, thiol, halogen, alkoxy, alkylamino, dialkylamino, substituted alkoxy, carboxyl, carbonyl, substituted carbonyl, amido, sulfonyl, sulfonic acid, phosphoryl, phosphonyl, phosphonyl, hydrogen, alkyl, substituted alkyl $R_4'$ is —$NO_2$ or hydrogen;

(c) wherein $R_5'$ is hydrogen, nitro, cyano, isocyano, amino, hydroxy (—OH), thiol, halogen (e.g. F, Cl, I, Br), alkoxy, alkylamino, dialkylamino, substituted alkoxy, carboxyl, carbonyl, substituted carbonyl, amido, sulfonyl, sulfonic acid, phosphoryl, phosphonyl, phosphonyl, hydrogen, alkyl, substituted alkyl, and n is an integer between 0 and 4, inclusive.

2. The agent of claim 1 having the structure (Formula III)-(Formula II)-D:

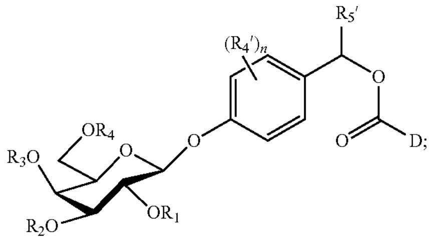

wherein D comprises a cytotoxic agent, wherein the cytotoxic moiety is gemcitabine.

3. The agent of claim 1, wherein at least one $R_4$' is nitro, cyano, amino, hydroxy, thiol, halogen, alkoxy, alkylamino, dialkylamino, substituted alkoxy, carboxyl, carbonyl, substituted carbonyl, amido, sulfonyl, sulfonic acid, phosphoryl, phosphonyl, hydrogen, or phosphonyl.

4. The agent of claim 1, wherein at least one $R_4$' is nitro, cyano, isocyano, amino, hydroxy, thiol, hydrogen, or halogen.

5. The agent of claim 1, wherein $R_4$' is —$NO_2$ or hydrogen.

6. The agent of claim 1, wherein Formula II has the structure:

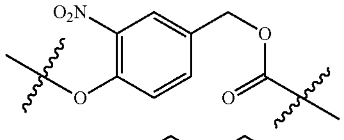

or

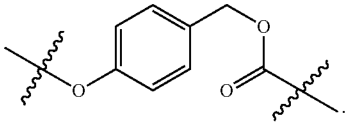

7. The agent of claim 1, wherein $R_1$, $R_2$, $R_3$, and $R_4$ are independently H, $R_5C(O)$—, or $R_6OC(O)$—, $R_7R_8NC(O)$—.

8. The agent of claim 1, wherein $R_1$, $R_2$, $R_3$, and $R_4$ are independently $R_5C(O)$—.

9. The agent of claim 1, wherein $R_5$, $R_6$, $R_7$, $R_8$, and $R_9$ are independently hydrogen, substituted $C_1$-$C_5$ alkyl, unsubstituted $C_1$-$C_5$ alkyl, substituted $C_6$-$C_{10}$ aryl, unsubstituted $C_6$-$C_{10}$ aryl, substituted $C_6$-$C_{10}$ heteroaryl, unsubstituted $C_6$-$C_{10}$ heteroaryl, substituted $C_3$-$C_{10}$ cyclyl, unsubstituted $C_3$-$C_{10}$ cyclyl, or substituted $C_3$-$C_{10}$ heterocyclyl, unsubstituted $C_3$-$C_{10}$ heterocyclyl.

10. The agent of claim 1, wherein $R_5$, $R_6$, $R_7$, $R_8$, and $R_9$ are independently hydrogen, substituted $C_1$-$C_3$ alkyl, unsubstituted $C_1$-$C_3$ alkyl, substituted $C_6$ aryl, unsubstituted $C_6$ aryl, substituted $C_6$ heteroaryl, unsubstituted $C_6$ heteroaryl, substituted $C_6$ cyclyl, unsubstituted $C_6$ cyclyl, or substituted $C_6$ heterocyclyl, unsubstituted $C_6$ heterocyclyl.

11. The agent of claim 1, wherein $R_5$ is independently substituted $C_1$-$C_3$ alkyl or unsubstituted $C_1$-$C_3$ alkyl.

12. The agent of claim 1, wherein Formula III has the structure:

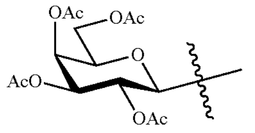

or

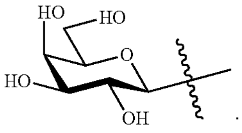

13. The agent of claim 1, wherein the agent comprises any one of the following structures:

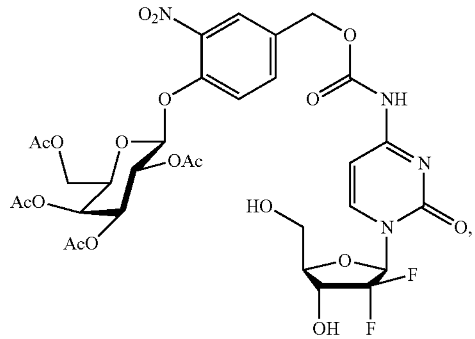

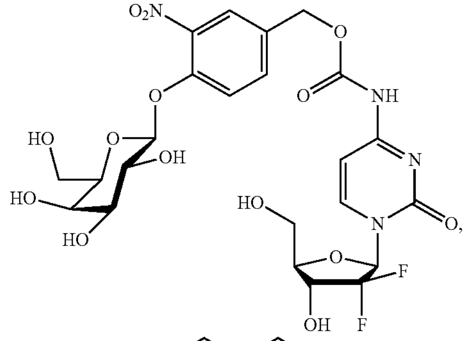

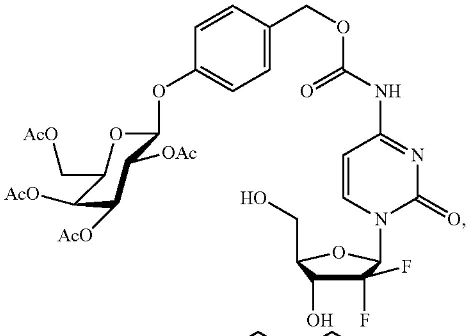

and

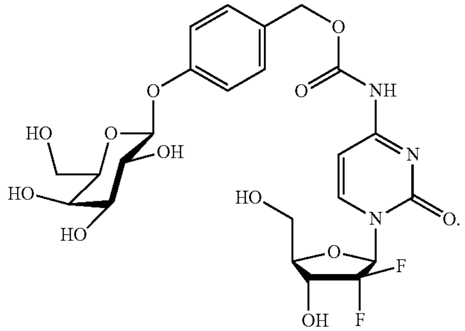

14. A composition comprising the agent of claim 1, in an effective amount to kill one or more senescent cells or ameliorating one or more symptoms associated with an inflammatory disorder.

15. The composition of claim 14, wherein the agent selectively kills one or more senescent cells over non-senescent cells, as determined in a cell culture assay.

16. The composition of claim 14 comprising a pharmaceutically acceptable carrier.

17. A method of selectively killing one or more senescent cells or ameliorating one or more symptoms associated with an inflammatory disorder in a subject, said method comprising administering to the subject a therapeutically effective amount of the composition of claim 14.

18. The method of claim 17, wherein the subject has a senescence-associated disease or disorder or an inflammatory disease or disorder.

19. The method of claim 17, wherein the senescence-associated disease or disorder is a metabolic disease, an inflammatory disease or disorder, a pulmonary disease or disorder, a neurological disease or disorder, a proliferative disorder, a renal disorder or disease, an eye disease or disorder, or a dermatological disorder or disease.

20. The method of claim 17, wherein the senescence-associated disease or disorder is selected from:

(i) an inflammatory or autoimmune disease or disorder selected from osteoarthritis, osteoporosis, oral mucositis, inflammatory bowel disease, kyphosis and herniated intervertebral disc;

(ii) a neurological disease or disorder selected from Alzheimer's disease, Parkinson's disease, Huntington's disease, dementia, mild cognitive impairment, macular degeneration and motor neuron dysfunction;

(iii) a metabolic disease selected from diabetes, diabetic ulcer, metabolic syndrome and obesity;

(iv) a pulmonary disease selected from pulmonary fibrosis, chronic obstructive pulmonary disease, asthma, cystic fibrosis, emphysema, bronchiectasis and age-related loss of pulmonary function;

(v) an eye disease or disorder selected from macular degeneration, glaucoma, cataracts, presbyopia and vision loss;

(vi) an age-related disorder selected from renal disease, renal failure, frailty, hearing loss, muscle fatigue, skin conditions, skin wound healing, liver fibrosis, pancreatic fibrosis, oral submucosa fibrosis and sarcopenia; and (vii) a dermatological disease or disorder selected from eczema, psoriasis, hyperpigmentation, nevi, rashes, atopic dermatitis, urticaria, diseases and disorders related to photosensitivity or photoaging, rhytides, pruritis, dysesthesia, eczematous eruptions, eosinophilic dermatosis, reactive neutrophilic dermatosis, pemphigus, pemphigoid, immunobullous dermatosis, fibrohistocytic proliferations of skin, cutaneous lymphomas and cutaneous lupus.

21. The method of claim 20, wherein the subject is diagnosed with cancer.

22. The method of claim 21, wherein the agent (i) reduces or cancer cells that have been pushed to senescence;

(ii) reduces one or more side effects produced by senescent cells, wherein said side effects comprise inflammation, promotion of cancer growth and promotion of metastasis;

(iii) reduces one or more side effects of chemotherapy; or (iv) reduces one or more side effects or radiotherapy.

23. The method of claim 17, wherein the composition comprises an agent having the structure (Formula III)-(Formula II)-D:

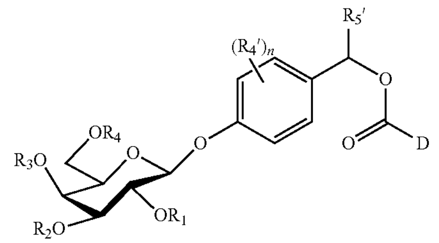

wherein D is cleaved following in vivo delivery.

24. The method of claim 17, wherein the composition comprises any of the following structures:

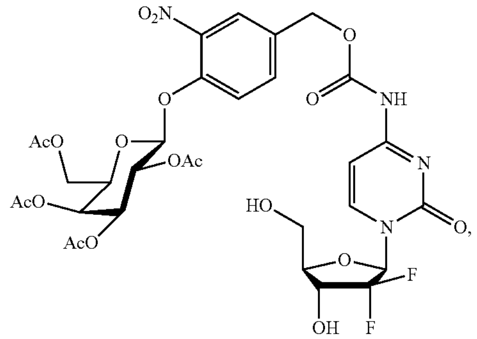

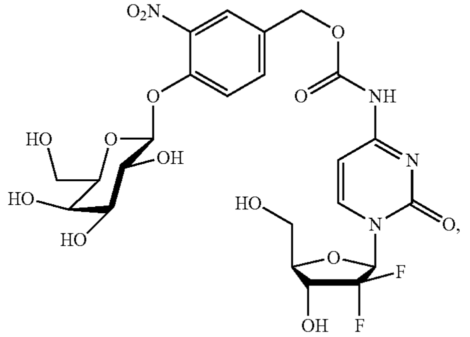

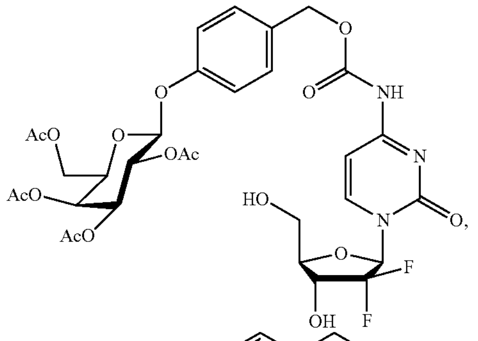

and

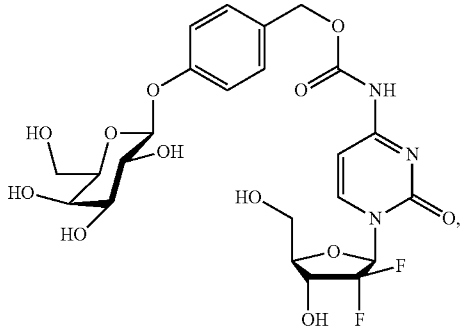

wherein a structure:

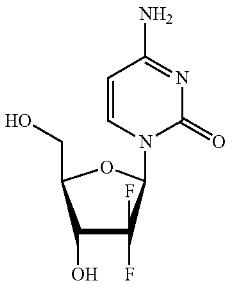

is obtained following in vivo administration, in an effective amount to kill one or more senescent cells.

25. The method of claim 17, wherein the subject has a viral infection.

26. The method of claim 25, wherein the viral infection is a coronavirus infection selection from the group consisting of coronavirus, Severe Acute Respiratory Syndrome (SARS) coronaviruses (CoV), SARS-COV-2 (which causes COVID-19 (Coronavirus Disease 2019)), and Middle East respiratory syndrome (MERS)-CoV.

27. The method of claim 26, wherein the subject has a SARS-CoV-2 infection and has been diagnosed with Coronavirus Disease 2019.

* * * * *